(12) United States Patent
Ahrens et al.

(10) Patent No.: US 8,263,043 B2
(45) Date of Patent: *Sep. 11, 2012

(54) CELLULAR LABELING AND QUANTIFICATION FOR NUCLEAR MAGNETIC RESONANCE TECHNIQUES

(75) Inventors: Eric T. Ahrens, Pittsburgh, PA (US); Mangala Srinivas, Singapore (SG)

(73) Assignee: Carnegie Mellon University, Pittsburgh, PA (US)

( * ) Notice: Subject to any disclaimer, the term of this patent is extended or adjusted under 35 U.S.C. 154(b) by 1309 days.

This patent is subject to a terminal disclaimer.

(21) Appl. No.: 11/787,521

(22) Filed: Apr. 16, 2007

(65) Prior Publication Data

US 2007/0253910 A1 Nov. 1, 2007

Related U.S. Application Data

(60) Provisional application No. 60/792,003, filed on Apr. 14, 2006.

(51) Int. Cl.
*A61B 5/055* (2006.01)
*A61B 5/00* (2006.01)

(52) U.S. Cl. ........... 424/9.34; 424/9.5; 424/9.6; 424/9.8

(58) Field of Classification Search .................. 424/9.3, 424/9.6–9.8, 489; 514/450, 832
See application file for complete search history.

(56) References Cited

U.S. PATENT DOCUMENTS

| | | | |
|---|---|---|---|
| 4,094,911 A | 6/1978 | Zollinger et al. | |
| 4,558,279 A | 12/1985 | Ackerman et al. | |
| 4,570,004 A | 2/1986 | Lagow et al. | |
| 4,714,680 A | 12/1987 | Civin | |
| 4,783,401 A | 11/1988 | Horan et al. | |
| 4,838,274 A | 6/1989 | Schweighardt et al. | |
| 4,935,223 A | 6/1990 | Phillips | |
| 4,990,283 A | 2/1991 | Visca et al. | |
| 4,996,041 A | 2/1991 | Arai et al. | |
| 5,061,620 A | 10/1991 | Tsukamoto et al. | |
| 5,114,703 A | 5/1992 | Wolf et al. | |
| 5,196,348 A * | 3/1993 | Schweighardt et al. | 436/173 |
| 5,330,681 A | 7/1994 | Brunetta et al. | |
| 5,397,562 A | 3/1995 | Mason et al. | |
| 5,437,994 A | 8/1995 | Emerson et al. | |
| 5,460,800 A * | 10/1995 | Walters | 424/9.6 |
| 5,486,359 A | 1/1996 | Caplan et al. | |
| 5,539,059 A | 7/1996 | Bierschenk et al. | |
| 5,589,376 A | 12/1996 | Anderson et al. | |
| 5,643,741 A | 7/1997 | Tsukamoto et al. | |
| 5,690,907 A | 11/1997 | Lanza et al. | |
| 5,716,827 A | 2/1998 | Tsukamoto et al. | |
| 5,750,397 A | 5/1998 | Tsukamoto et al. | |
| 5,753,506 A | 5/1998 | Johe | |
| 5,763,197 A | 6/1998 | Tsukamoto et al. | |
| 5,766,948 A | 6/1998 | Gage et al. | |
| 5,785,950 A | 7/1998 | Kaufman et al. | |
| 5,824,489 A | 10/1998 | Anderson et al. | |
| 5,827,735 A | 10/1998 | Young et al. | |
| 5,843,780 A | 12/1998 | Thomson | |
| 5,851,832 A | 12/1998 | Weiss et al. | |
| 5,914,108 A | 6/1999 | Tsukamoto et al. | |
| 5,925,567 A | 7/1999 | Kraus et al. | |
| 5,942,225 A | 8/1999 | Bruder et al. | |
| 5,958,371 A | 9/1999 | Lanza et al. | |
| 5,972,703 A | 10/1999 | Long et al. | |
| 6,040,180 A | 3/2000 | Johe | |
| 6,090,622 A | 7/2000 | Gearhart et al. | |
| 6,171,610 B1 | 1/2001 | Vacanti et al. | |
| 6,190,910 B1 | 2/2001 | Kusakabe et al. | |
| 6,200,806 B1 | 3/2001 | Thomson | |
| 6,245,566 B1 | 6/2001 | Gearhart et al. | |
| 6,331,406 B1 | 12/2001 | Gearhart et al. | |
| 6,361,996 B1 | 3/2002 | Rao et al. | |
| 6,468,794 B1 | 10/2002 | Uchida et al. | |
| 6,511,967 B1 | 1/2003 | Weissleder et al. | |
| 7,357,937 B2 | 4/2008 | Hsu et al. | |
| 7,514,074 B2 | 4/2009 | Pittinger et al. | |
| 2002/0016002 A1 | 2/2002 | Toma et al. | |
| 2002/0045259 A1 | 4/2002 | Lim et al. | |
| 2002/0068045 A1 | 6/2002 | Reubinoff et al. | |
| 2002/0123143 A1 | 9/2002 | Toma et al. | |
| 2002/0192688 A1 | 12/2002 | Yang et al. | |
| 2003/0003574 A1 | 1/2003 | Toma et al. | |
| 2004/0109824 A1 * | 6/2004 | Hinds et al. | 424/9.32 |
| 2005/0008572 A1 * | 1/2005 | Prokop et al. | 424/9.6 |
| 2005/0079131 A1 | 4/2005 | Lanza et al. | |

(Continued)

FOREIGN PATENT DOCUMENTS

DE 2 242 191 4/1972

(Continued)

OTHER PUBLICATIONS

Charles H. Cunningham et al. Positive Contrast Magnetic Resonacne Imaging of Cells Labeled with Magnetic Nanoparticles, Magnetic Resonance in Medicine 53, 999-1005, 2005.*

Barnett et al., Radiopaque Alginate Microcapsules for X-ray Visualization and Immunoprotection of Cellular Therapeutics, Mol. Pharm. 3(5):531-538 (2006).

Ablamunits et al., Acceleration of autoimmune diabetes by cyclophosphamide is associated with an enhanced IFN-gamma secretion pathway, J. Autoimmun. 13(4):383-392 (1999).

Ahrens and Dubowitz, Peripheral somatosensory fMRI in mouse at 11.7T, NMR Biomed., 14:318-324 (2001).

Ahrens et al., Receptor-mediated endocytosis of iron-oxide particles provides efficient labeling of dendritic cells for in vivo MR imaging, Mag. Reson. Med. 49:1006-1013 (2003).

(Continued)

*Primary Examiner* — Michael G Hartley
*Assistant Examiner* — Jagadishwar Samala
(74) *Attorney, Agent, or Firm* — Ropes & Gray LLP

(57) ABSTRACT

The disclosure provides, in part, a method for quantifying cell numbers in vivo. The disclosure comprises a method of quantifying labeled cells by nuclear magnetic resonance techniques and a computer method for the same.

33 Claims, 19 Drawing Sheets

(5 of 19 Drawing Sheet(s) Filed in Color)

U.S. PATENT DOCUMENTS

| | | | |
|---|---|---|---|
| 2005/0244384 A1 | 11/2005 | Law | |
| 2006/0040389 A1 | 2/2006 | Murry et al. | |
| 2006/0239919 A1* | 10/2006 | Wickline et al. | 424/9.3 |
| 2007/0253910 A1 | 11/2007 | Ahrens et al. | |
| 2007/0258886 A1 | 11/2007 | Ahrens et al. | |
| 2009/0263329 A1* | 10/2009 | Wickline et al. | 424/9.37 |

FOREIGN PATENT DOCUMENTS

| | | |
|---|---|---|
| DE | 42 03 254 | 5/1996 |
| EP | 0 307 863 | 7/1991 |
| EP | 0 307 087 | 6/1994 |
| EP | 1 728 788 | 12/2006 |
| WO | WO91/14664 | 10/1991 |
| WO | WO94/18954 | 9/1994 |
| WO | WO-94/21303 | 9/1994 |
| WO | WO96/41647 | 12/1996 |
| WO | WO97/40679 | 11/1997 |
| WO | WO-98/20907 | 5/1998 |
| WO | WO-00/02654 | 1/2000 |
| WO | WO-00/53795 | 9/2000 |
| WO | WO-2005/072780 | 8/2005 |
| WO | WO2006/096499 | 9/2006 |
| WO | WO 2007/100715 | 9/2007 |
| WO | WO2008/119790 | 10/2008 |
| WO | WO 2008/144028 | 11/2008 |
| WO | WO2009/009105 | 1/2009 |

OTHER PUBLICATIONS

Ahrens et al., A model for MRI contrast enhancement using $T_1$ agents, Proc. Natl. Acad. Sci. USA, 95:8443-8448 (1998).

Ahrens et al., In vivo imaging platform for tracking immunotherapeutic cells, Nat. Biotechnol. 23(8):983-987 (2005).

Allen et al., Cellular delivery of MRI contrast agents, Chem. Bio. 11(3):301-307 (2004).

Anderson et al., Magnetic resonance imaging of labeled T-cells in a mouse model of multiple sclerosis, Ann. Neurol. 55(5):654-659 (2004).

Arbab et al., Efficient magnetic cell labeling with protamine sulfate complexed to ferumoxides for cellular MRI, Blood 15:104(4):1217-23 (2004).

Billotey et al., T-cell homing to the pancreas in autoimmune mouse models of diabetes: in vivo MR imaging, Radiology 236(2):579-587 (2005).

Bulte et al., Preparation of magnetically labeled cells for cell tracking by magnetic resonance imaging. Method Enzymol. 386:275-299 (2004).

Cantor and Haskins, Effector function of diabetogenic CD4 Th1 T cell clones: a central role for TNF-alpha, J. Immunol. 175(11):7738-7745 (2005).

Cheng et al., Characterization of aqueous dispersions of Fe(3)O(4) nanoparticles and their biomedical applications, Biomaterials 26(7):729-738 (2005).

Dardzinski and Sotak, Rapid tissue oxygen tension mapping using 19F inversion-recovery echo-planar imaging of perfluoro-15-crown-5-ether, Magn. Reson. Med. 32(1):88-97 (1994).

Derossi et al, The Third Helix of the Antennapedia Homeodomain Translocates through Biological Membranes, J. Biol. Chem. 269(14):10444-10450 (1994).

Derossi et al., Cell Internalization of the Third Helix of the Antennapedia Homeodomain Is Receptor-Independent, J. Biol. Chem. 271(30):18188-18193 (1996).

Dodd et al., Normal T-cell response and in vivo magnetic resonance imaging of T cells loaded with HIV transactivator-peptide-derived superparamagnetic nanoparticles, J. Immun. Meth. 256(1-2):89-105 (2001).

Dousset et al., In vivo macrophage activity imaging in the central nervous system detected by magnetic resonance, Mag. Res. Med. 41(2):329-333 (1999).

Duong and Kim, In vivo MR measurements of regional arterial and venous blood volume fractions in intact rat brain, Mag. Res. Med. 43(3):393-402 (2000).

Eidelberg et al., 19F NMR imaging of blood oxygenation in the brain, Mag. Res. Med. 6(3):344-52 (1988).

Elster et al., Dyke Award. Europium-DTPA: a gadolinium analogue traceable by fluorescence microscopy, Am. J. Neuroradiol. 10(6):1137-1144 (1989).

Evgenov et al., In vivo imaging of immune rejection in transplanted pancreatic islets, Diabetes 55(9):2419-2428 (2006).

Evgenov et al., In vivo imaging of islet transplantation, Nat. Med. 12(1):144-148 (2006).

Fabien et al., Pancreatic lymph nodes are early targets of T cells during adoptive transfer of diabetes in NOD mice, J. Autoimmun. 8(3):323-334 (1995).

Feili-Hariri, M. et al., Immunotherapy of NOD mice with bone marrow-derived dendritic cells, Diabetes, 48:2300-2308 (1999).

Fishman et al., Oxygen-sensitive 19F NMR imaging of the vascular system in vivo, Magn. Reson. Imaging 5(4):279-285 (1987).

Floris et al., Blood-brain barrier permeability and monocyte infiltration in experimental allergic encephalomyelitis: a quantitative MRI study, Brain. 127(Pt 3):616-27 (2004).

Forstrom et al., 18F-FDG Labelling of Human Leukocytes, Nucl. Med. Comm. 21(7):691-694 (2000).

Frankel et al., Cellular uptake of the tat protein from human immunodeficiency virus, Cell, 55:1189-1193 (1989).

Friedrich and Soriano, Promoter traps in embryonic stem cells: a genetic screen to identify and mutate developmental genes in mice, Genes & Dev. 5:1513-1523 (1991).

Girolomoni et al., Establishment of a Cell-Line with Features of Early Dendritic Cell Precursors from Fetal Mouse Skin, Eur. J. Imm. 25(8):2163-2169 (1995).

Granot et al., Labeling fibroblasts with biotin-BSA-GdDTPA-FAM for tracking of tumor-associated stroma by fluorescence and MR imaging, Magn, Reson. Med. 54(4):789-797 (2005).

Green et al., Autonomous functional domains of chemically synthesize human immunodeficiency virus tat trans-activator protein, Cell, 55:1179-1188 (1988).

Gritti et al., Multipotent neural stem cells reside into the rostral extension and olfactory bulb of adult rodents, The Journal of Neuroscience, 22(2):437-445 (2002).

Gudbjartsson and Patz, The Rician distribution of noisy MRI data, Magn. Reson. Med. 34(6):910-914 (1995).

Hoehn et al., Monitoring of implanted stem cell migration in vivo: A highly resolved in vivo magnetic resonance imaging investigation of experimental stroke in rat, Proc. Natl. Acad. Sci. USA 99(25):16267-16272 (2002).

Josephson et al., High-efficiency intracellular magnetic labeling with novel superparamagnetic-tat peptide conjugates, Bioconjugate Chem. 10(2):186-191 (1999).

Kanno et al., Macrophage accumulation associated with rat cardiac allograft rejection detected by magnetic resonance imaging with ultrasmall superparamagnetic iron oxide particles, Circulation 104(8):934-938 (2001).

Kimura et al., Neurite outgrowth of PC12 cells is suppressed by wortmannin, a specific inhibitor of phosphatidylinositol 3-kinase, J. Biol. Chem. 269:18961-18967 (1994).

Kircher et al., In vivo high resolution three-dimensional imaging of antigen-specific cytotoxic T-lymphocyte trafficking to tumors, Cancer Res. 63(20):6838-6846 (2003).

Krause et al., Multi-organ multi-lineage engraftment by a single bone marrow-derived stem cell, Cell 105:369-377 (2001).

Kuppuswamy et al., Multiple functional domains of Tat, the trans-activator of HIV-1, defined by mutational analysis, Nucl. Acids Res. 17:3551-3561 (1989).

Lagasse et al., Purified hematopoietic stem cells can differentiate into hepatocytes in vivo, Nat. Med. 6(11):1229-1234 (2000).

Lanza et al., 1H/19F magnetic resonance molecular imaging with perfluorocarbon nanoparticles, In: Ahrens ET, editor. In vivo cellular and molecular imaging, Curr. Top. Dev. Biol. 70:58-78 (2005).

Leiter et al., The nonobese diabetic (NOD) mouse, Am. J. Pathol. 128(2):380-383 (1987).

Lewin et al., Tat peptide-derivatized magnetic nanoparticles allow in vivo tracking and recovery of progenitor cells., Nat. Biotechnol. 18(4):410-414 (2000).

Lutz et al., Measurement of oxygen tensions in the abdominal cavity and in the skeletal muscle using 19F-MRI of neat PFC droplets, Adv. Exp. Med. Biol. 428:569-572 (1997).

Mason, Non-invasive physiology: $^{19}$F NMR of perfluorocarbons, Art. Cells, Blood Subs., and Immob. Biotech. 22(4):1141-1153 (1994).
McGoron et al., Perfluorocarbon distribution to liver, lung and spleen of emulsions of perfluorotributylamine (FTBA) in pigs and rats and perfluorooctyl bromide (PFOB) in rats and dogs by F-19 NMR-spectroscopy, Artificial Cells Blood Substitutes and Immobilization Biotechnology 22(4):1243-1250 (1994).
Means et al., Chemical modifications of proteins: history and applications, Bioconj. Chem. 1:2-12 (1990).
Meyer et al., Measurement of vascular volume in experimental rat tumors by 19F magnetic resonance imaging, Invest. Radiol. 28(8):710-719 (1993).
Miller et al., Imaging the single cell dynamics of CD4+ T cell activation by dendritic cells in lymph nodes, J. Exp. Med. 200(7):847-856 (2004).
Miyazaki et al., Predominance of lymphocytes-T in pancreatic-islets and spleen of pre-diabetic non-obese diabetic (NOD) mice—a longitudinal-study, Clin. Exp. Immunol. 60(3):622-630 (1985).
Modo et al., Mapping transplanted stem cell migration after a stroke: a serial, in vivo magnetic resonance imaging study, Neuroimage 21(1):311-317 (2004).
Moore et al., Tracking the recruitment of diabetogenic CD8+ T-cells to the pancreas in real time, Diabetes 53(6):1459-1466 (2004).
Moore et al., Uptake of dextran-coated monocrystalline iron oxides in tumor cells and macrophages, J. Mag. Reson. Imaging 7(6): 1140-1145 (1997).
Morawski et al., Quantitative magnetic resonance immunohistochemistry with ligand-targeted F-19 nanoparticles, Magn. Reson. Med. 52(6):1255-1262 (2004).
Noth et al., In vivo measurement of partial oxygen pressure in large vessels and in the reticuloendothelial system using fast 19F-MRI, Magn. Reson. Med. 34(5):738-745 (1995).
Noth et al., Perfluoro-15-crown-5-ether labelled macrophages in adoptive transfer experimental allergic encephalomyelitis, Artificial Cells Blood Substitutes and Immobilization Biotechnology 25(3): 243-254 (1997).
Pakala et al., T helper 2 (Th2) Tcells induce acute pancreatitis and diabetes in immune-compromised nonobese diabetic (NOD) mice, J. Exp. Med. 186(2):299-306 (1997).
Pelchen-Matthews et al., Phorbol ester-induced downregulation of CD4 is a multistep process involving dissociation from p56lck, increased assocation with clathrin-coated pits, and altered endosomal sorting, J. Exp. Med. 178(4):1209-1222 (1993).
Perez et al., Antennapedia homeobox as a signal for the cellular internalization and nuclear addressing of a small exogenous peptide, J. Cell Sci. 102:717-722 (1992).
Phillips et al., MAdCAM-1 is needed for diabetes development mediated by the T cell clone, BDC-2.5, Immunology 116(4):525-531(2005).
Phillips et al., Nondepleting anti-CD4 has an immediate action on diabetogenic effector-cells, halting their destruction of pancreatic beta cells, J. Immunol. 165(4):1949-1955 (2000).
Pintaske et al., A preparation technique for quantitative investigation of SPIO-containing solutions and SPIO-labelled cells by MRI, Biomed. Tech. 50(6):174-180 (2005) (English Abstract).
Pittenger et al., Multilineage potential of adult human mesenchymal stem cells, Science, 284:143-147 (1999).
Pluchino et al., Injection of adult neurospheres induces recovery in a chronic model of multiple sclerosis, Nature 422(6933): 688-694 (2003).
Qiu et al., Null mutation of Dlx-2 results in abnormal morphogenesis of proximal first and second branchial arch derivatives and abnormal differentiation in the forebrain, Genes & Dev. 9:2523-2538 (1995).
Ribeiro et al., In vivo dynamics of T cell activation, proliferation, and death in HIV-1 infection: why are CD4+ but not CD8+ T cells depleted? Proc. Natl. Acad. Sci. USA 99(24):15572-15577 (2002).
Rodriguez et al., In vitro characterization of an Fe(8) cluster as potential MRI contrast agent, NMR Biomed. 18(5):300-307 (2005).
Ruben et al., Structural and functional characterization of human immunodeficiency virus tat protein, J. Vir. 63:1-8 (1989).
Sanchez et al., Highly Concentrated 1,2-bis (perfluoroalkyl) iodoethene emulsions for use as contrast agents for diagnosis, J. Fluor. Chem. 73(2):259-264 (1995).

Schneider et al., In vivo microscopic evaluation of the microvascular behavior of FITC-labeled macromolecular MR contrast agents in the hamster skinfold chamber, Invest. Radiol. 35(9):564-570 (2000).
Schoepf et al., Intracellular magnetic labeling of lymphocytes for in vivo trafficking studies, Biotechniques 24(4): 642-651 (1998).
Schulze et al., Cellular uptake and trafficking of a prototypical magnetic iron oxide label in vitro, Invest. Radiol. 30(10):604-10 (1995).
Shapiro et al., In vivo detection of single cells by MRI, Magn. Reson. Med. 55(2):242-249 (2006).
Turvey et al., Noninvasive imaging of pancreatic inflammation and its reversal in type 1 diabetes, J. Clin. Invest. 115(9):2454-2461 (2005).
Venanzi et al., Structural properties and photophysical behavior of conformationally constrained hexapeptides functionalized with a new fluorescent analog of tryptophan and a nitroxide radical quencher, Biopolymers 75(2):128-139 (2004).
Weissleder et al., Magnetically labeled cells can be detected by MR imaging. J. Mag. Res. Imag. 7(1): 258-263 (1997).
Wilson et al., Measurement of preretinal oxygen-tension in the vitrectomized human eye using F-19 magnetic resonance spectroscopy, Arch. Ophthalmol-Chic. 110(8):1098-1100 (1992)
Wu et al., In situ labeling of immune cells with iron oxide particles: An approach to detect organ rejection by cellular MRI, Proc. Natl. Acad. Sci. USA 103(6):1852-1857 (2006).
Xia et al., Tumour oxygen dynamics measured simultaneously by near-infrared spectroscopy and F-19 magnetic resonance imaging in rats, Phys. Med. Biol. 51(1):45-60 (2006).
Ye et al., In vivo detection of acute rat renal allograft rejection by MRI with USPTO particles. Kid. Intl. 61(3):1124-1135 (2002).
Yeh et al., Intracellular labeling of T-cells with superparamagnetic contrast agents, Magn. Reson. Med. 30(5):617-625 (1993).
Yeh et al., In-vivo dynamic MRI tracking of rat T-cells labeled with superparamagnetic iron-oxide particles, Magn. Reson. Med. 33:200-208 (1995).
You et al., Detection and characterization of T cells specific for BDC2.5 T cell-stimulating peptides, J. Immunol. 170(8):4011-4020 (2003).
Zhao et al., Human bone marrow stem cells exhibit neural phenotypes and ameliorate neurological deficits after grafting into the ischemic brain of rats, Exp. Neur. 174:11-20 (2002).
Crowder, Kathryn et al. "Unique perflourocarbon nanobeacons improve stem/progenitor cell tracking with MRI" FASEB Journal, vol. 20, No. 4, part 1. Mar. 2006, pp. A633, Abstract.
Helmer et al. "On the correlation between the water diffusion coefficient and oxygen tension in RIF-1 tumors" NMR in Biomedicine, v. 11, No. 3, May 1998, pp. 120-130.
Kraitchman et al., "In vivo magnetic resonance imaging of mesenchymal stem cells in myocardial infarction," Circulation v. 107, No. 18, May 2003, pp. 2290-2293.
Kravtzoff et al., "GD-DOTA Loaded into red blood cells. A new magnetic resonance imaging contrast agents for vascular system," Advances in Experimental MEdicine and Biology. v. 326, Jan. 1992, pp. 347-326.
Morawski et al., "Targeted Nanoparticles for Quantitative Imaging of Sparse Molecular Epitopes with MRK" Magnetic Resonance in Medicine, v. 51, No. 3, Mar. 2004, pp. 480-486.
Neubauer et al., "Endothelial stem cell detection in vivo with unique perflourocarbon nanoparticle labels using fluorine (F-19) MNRI at 1.5 T" Circulation, v. 114, No. 18, Suppl. S, Oct. 2006, p. 251, Abstract.
Srinivas et al., "Fluorine-19 MRI for visualization and quantification of cell migration in a diabetes model," Magnetic Resonance in Medicine, v. 58, No. 4, Oct. 2007, pp. 725-734.
Basse-Lusebrink et al., Multi-color $^{19}$F CSI: Simultaneous detection of differently labeled cells in vivo, Abstract #806, Proc. Int. Soc. Mag. Reson. 17 (2009).
Caruthers et al., In vitro demonstration using 19F magnetic resonance to augment moleculr imaging with paramagnetic perfluorocabon nanoparticles at 1.5 Tesla, Invest. Radiology 41(3):305-313, 2006.
Fan et al., MRI of perfluorocarbon emulsion kinetics in rodent mammary tumours, Phys. Med. & Biol. 51:211-200 (2006).

Flögel et al., In vivo monitoring of inflammation after cardiac and cerebral ischemia by fluorine magnetic resonance imaging, Circulation 118:140-148 (2008).

Hitchens et al., Comparison of iron-oxide- and perfluorocarbon-based cellular contrast agents for detecting immune cell infiltration in models of organ transplant rejection, Abstract #931, Proc. Int. Soc. Mag. Reson. 17 (2009).

Janjic et al., Self-delivering nanoemulsions for dual fluorine-19 MRI and fluorescence detection, J. Amer. Chem. Soc. 130:2832-2841 (2008).

Jiang et al., The Design and Synthesis of Highly Branched and Spherically Symmetric Fluorinated Oils and Amphiles, Tetrahedron 63(19):3982-3988 (2007).

Kim et al., Interplay of tumor vascular oxygenation and tumor pO2 observed using near-infrared spectroscopy, an oxygen needle electrode, and 19F MR pO2 mapping, J. Biomed Opt 8:53-62 (2003).

Klug et al., 1H/19F molecular MR-imaging in mouse models of acute and chronic inflammation, Abstract #3172, Proc. Int. Soc. Mag. Reson. 17 (2009).

Lanza et al., A novel site-targeted ultrasonic contrast agent with broad biomedical application, Circulation 94(12):3334-3340 (1996).

Laukemper-Ostendorf et al., 19F-MRI of perflubron for measurement of oxygen partial pressure in porcine lungs during partial liquid ventilation, Magn. Reson. Med. 47:82-89 (2002).

Mason et al., Hexafluorobenzene: a sensitive 19F NMR indicator of tumor oxygenation, NMR Biomed 9:125-134; (1996).

McNab et al., Tissue oxygen tension measurements in the Shionogi model of prostate cancer using $^{19}$F MRS and MRI, MAGMA 17:288-295 (2004).

Partlow et al., 19F magnetic resonance imaging for stem/progenitor cell tracking with multiple unique perfluorocarbon nanobeacons, FASEB J. 21:1647-1654 (2007).

Piacenti et al., Synthesis and characterization of fluorinated polyetheric amides, J. Fluor. Chem. 68:227-235 (1994).

Soloski, Synthesis of perfluoro (polyether) difunctional compounds, J. Fluor. Chem. 11:601-612 (1978).

Sotak et al., A new perfluorocarbon for use on fluorine-19 magnetic resonance imaging and spectroscopy, Magn. Reson. Med. 29:188 (1993).

Taylor and Deutsch, 19F-nuclear magnetic resonance: measurements of [O2] and pH in biological systems, Biophys J. 53: 227-233 (1988).

Tonelli et al., Linear perfluoropolyether difunctional oligomers: chemistry, properties and applications, J. Fluorine Chem. 95:51-70 (1999).

Tonelli et al., Perfluoropolyether alkyl diesters: Structure effects of the alkyl group on the kinetics of the hydrolysis reactions, J. Polym, Sci. Part A: Polym Chem. 40:4266-4280 (2002).

Tonelli et al., Perfluoropolyether functional oligomers: unusual reactivity in organic chemistry. J. Fluor. Chem. 118(1-2):107-121 (2002).

Wilhelm et al., Magnetophoresis and ferromagnetic resonance of magnetically labeled cells, Eur. Biophys. J. 31:118-125 (2002).

Wisner et al., A modular lymphographic magnetic resonance imaging contrast agent: contrast enhancement with DNA transfection potential, J. Med. Chem. 40(25):3992-3996 (1997).

Yu et al., High-resolution MRI characterization of human thrombus using a novel fibrin-targeted paramagnetic nanoparticle contrast agent, Mag. Res. In Med. 44:867-872 (2000).

Zhang et al., Synthetic applications of fluorous solid-phase extraction (F-SPE), Tetranedron 62:11837-11865 (2006).

* cited by examiner

Note: dashed connection denotes "optional"

a b

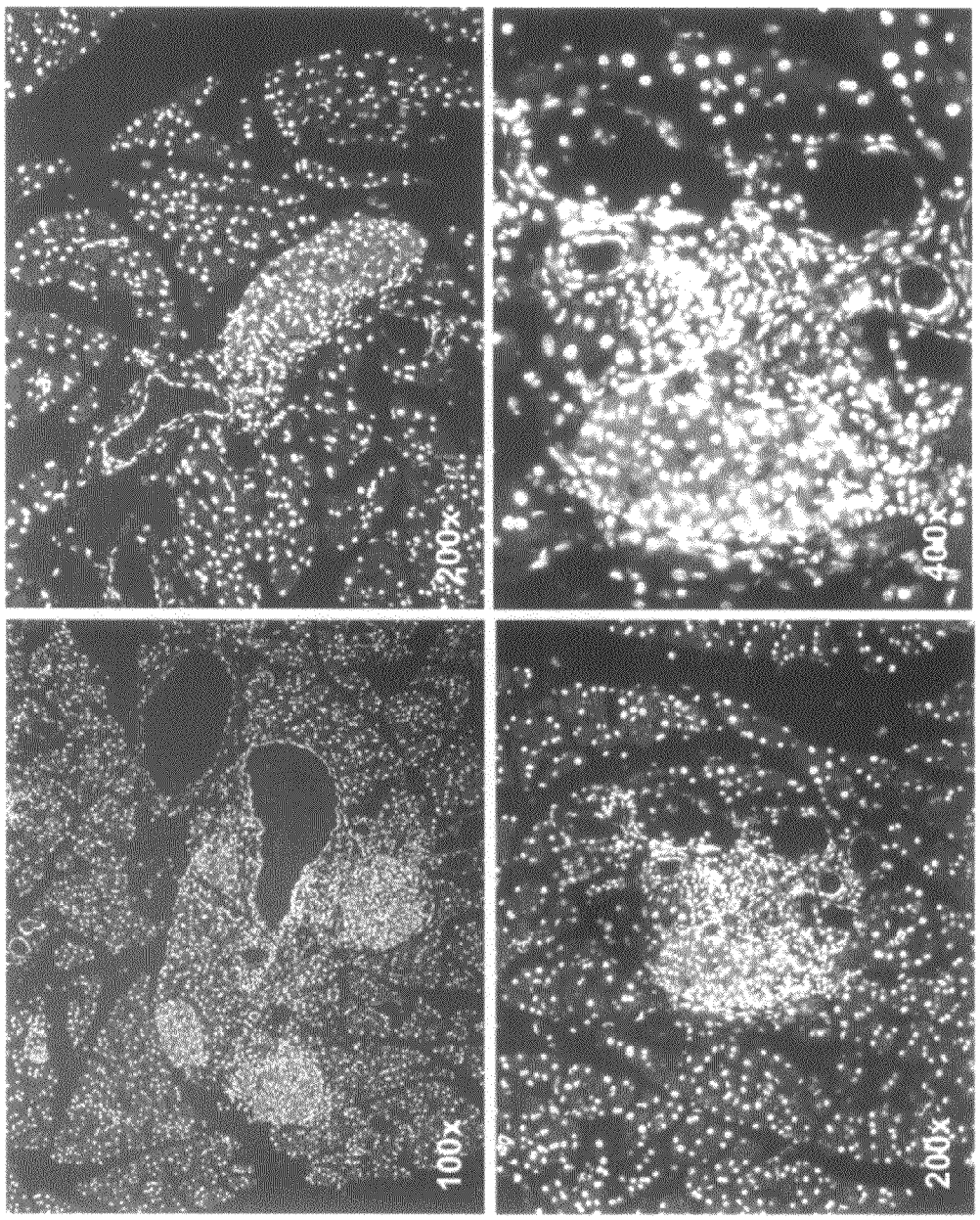

CELLULAR LABELING AND QUANTIFICATION FOR NUCLEAR MAGNETIC RESONANCE TECHNIQUES

RELATED APPLICATIONS

This application claims the benefit of U.S. Provisional Patent Application Ser. No. 60/792,003, filed on Apr. 14, 2006, the entire disclosure of which is incorporated herein by this reference.

STATEMENT REGARDING FEDERALLY-SPONSORED RESEARCH OR DEVELOPMENT

The invention described herein was supported, in whole or in part, by the National Institutes of Health (R01-EB003453, R01-EB004155, P01-HD047675, P50-ES012359). The Pittsburgh NMR Center is supported by the National Institute of Biomedical Imaging and Bioengineering as a National Biomedical Research Resource Center (P41EB-001977). The U.S. Government has certain rights in the invention.

BACKGROUND

Many biological processes are carried out by populations of cells. For example, cells of the immune system are recruited from the bloodstream to areas of inflammation or infection, resulting in an accumulation of immune cells at the affected site. A marked infiltration of immune cells often occurs in tissues affected by autoimmune diseases, cancers and infections. Likewise, transplant rejection is mediated by host immune cells that enter and destroy the transplanted tissue. There is also growing evidence that stem cells originating in the bone marrow migrate through the bloodstream and assist in the regeneration of damaged tissues.

Furthermore, the most immediately promising area of biologic therapy involves the emerging field of cellular therapy. Cellular therapy is broadly defined as the treatment of human disease by the administration of therapeutic cells that have been selected, multiplied, and pharmacologically treated outside the body, or ex vivo. These cells may be derived from the patient (autologous cells), from another human (allogenic cells), from other organisms (xenogenic cells), or from immortalized cell lines.

Cells represent the ultimate therapeutic system because of their ability to carry out complex functions and their responsiveness to changes in the surrounding tissue or host organism. In the simplest mode of cellular therapy, cells can be isolated, grown in quantity ex vivo, and implanted in patients to produce and secrete soluble factors that directly address the mechanism of disease. Cells can also accomplish tasks as complex as reconstitution of tissues, organs, or immune responses based on their ability to home to specific sites within the body, to exit from circulation, and to integrate into specific tissue or differentiate into new tissue. Other cellular therapeutics can be programmed for tumor killing or treating metastases (e.g., immunotherapeutics).

Although dynamic cell populations play a key role in significant diseases, present technologies for monitoring the location and movement of cells in vivo are quite limited. Typically, cell movements are monitored only in "snap shots" obtained by histological analysis of tissue biopsies. However, the process of sampling a tissue often alters the behavior of cells, and only a limited number of biopsies can be obtained from a particular tissue or organ. Some progress has been made studying cell movements via in vitro assays and isolated tissues ex-vivo. Existing instruments for non-invasive analysis of living organisms are, at present, ill-suited for tracking living cells. Light-based imaging technologies, such as bioluminescence (e.g. luciferases) technologies, are often ineffective at visualizing deep structures because most mammalian tissues are optically opaque. Positron emission tomography (PET) techniques using radioactively-labeled probes are highly sensitive. However, PET instrumentation is often limited to a resolution of several millimeters and is unable to resolve fine details of tissues and organs. Furthermore, labeled cells cannot be detected for time periods that extend beyond a typical PET radioisotope half-life, and generally PET is not useful for longitudinal studies. In order to gain a fundamental understanding of cellular processes, new ways to visualize and quantify the population dynamics of specific cell types in vivo must be developed.

Magnetic resonance imaging (MRI) is a widely used clinical diagnostic tool because it is non-invasive, allows views into optically opaque subjects, and provides contrast among soft tissues at reasonably high spatial resolution. Conventional MRI focuses almost exclusively on visualizing anatomy and has no specificity for any particular cell type. The 'probe' used by conventional MRI is the ubiquitous proton ($^1$H) in mobile water molecules. New classes of exogenous MRI probes or reagents are needed to facilitate cell-specific imaging in living subjects.

SUMMARY

In certain aspects, the disclosure provides novel methods and reagents for labeling cells ex vivo with an imaging reagent, such as fluorocarbon imaging reagent that can be detected by a nuclear magnetic resonance technique. In certain aspects, the disclosure provides methods and software for quantifying the numbers of labeled cells at particular locations in vivo. Cells may be labeled with a label including a fluorocarbon, for example a perfluoropolyether (PFPE), and since biological tissues have negligible endogenous fluorine content, in vivo $^{19}$F MRI can provide an effective means of detecting labeled cells. In some embodiments these images are then superimposed on a conventional $^1$H MRI to determine anatomical localization.

Labeled cells may be administered to a subject and subsequently detected by nuclear magnetic resonance techniques. Examples of nuclear magnetic resonance techniques include magnetic resonance imaging (MRI) and localized magnetic resonance spectroscopy (MRS). Because nuclear magnetic resonance techniques are generally performed as non-invasive procedures, the labeled cells may be detected at one or more time points in a living subject. Labeled cells may also be detected in a cell culture or in essentially any other milieu on which a nuclear magnetic resonance technique can be performed, such as tissue explants, organs and tissues removed from a subject (possibly prior to transplant into a transplant recipient), artificially generated tissues and various matrices and structures seeded with cells.

In certain aspects, the disclosure provides methods for labeling a cell. Such methods may include contacting the cultured cells ex vivo with a fluorocarbon imaging reagent under conditions such that the fluorocarbon imaging reagent becomes associated with the cell. Perfluoropolyethers (PFPEs) are examples of suitable fluorocarbon imaging reagents. Perfluoropolyethers may be linear or cyclic (e.g., perfluoro-crown ethers). An imaging reagent may be formulated as an emulsion, often including a surfactant. An example would be an emulsion comprising PFPE (Exfluor, Round Rock, Tex.) and Pluronic L-35 or F68 (Sigma-Aldrich, St. Louis, Mo.).

Optionally, the cell may be contacted with the fluorocarbon imaging reagent in the presence of a reagent that enhances uptake of the fluorocarbon imaging reagent. Various cationic molecules, such as cationic lipids or protamine sulfate, are examples of a suitable uptake enhancing reagent; other such reagents are described herein and are, in view of this specification, known in the art. In certain embodiments, the composition of the surfactant may be designed to impart a cationic surface to the emulsion particle that enhances cellular uptake of the emulsion without the need of an enhancing reagent. In certain embodiments, the cells are labeled with perfluorocarbon emulsion particles by electroporation.

While a fluorocarbon imaging reagent may be internalized by a cell, it may also associate with the extracellular surface of a cell. Association with an extracellular surface may be increased by conjugating the imaging reagent to a cellular targeting moiety. A cellular targeting moiety may be essentially any molecular entity that binds to the desired cells, such as an antibody that binds to an epitope that is exposed to the extracellular milieu. Uptake of an imaging reagent into a cell may be increased by conjugating the imaging reagent to an internalization moiety. An internalization moiety is any molecular entity that stimulates or promotes entry of the imaging reagent into the cell. Examples include internalizing peptides and moieties that bind to receptors or other cell surface proteins that are internalized by, for example, receptor mediated endocytosis. The cell may be essentially any cell, including prokaryotic and eukaryotic cells. In preferred embodiments, the cell is a mammalian cell. In certain embodiments the cell is a cell of the immune system, such as a dendritic cell or T cell. A cell may also be a stem cell or a cell that has been prepared for administration to a subject as part of a cellular therapy or a transplant, such as a peripheral blood stem cell transplant or bone marrow transplant. Other cell types can be labeled and imaged, for example an embryonic stem cell, a pancreatic islet, a hepatocyte, etc., perhaps in conjunction with a therapy.

In certain aspects, the disclosure provides methods of labeling cells with fluorocarbon imaging reagents. Preferred fluorocarbon imaging reagents have one or more of the following properties: reduced cytotoxicity; a $^{19}$F NMR spectrum that is simple, ideally having mostly a single, narrow resonance to minimize chemical shift artifacts; a large number of NMR-equivalent fluorine atoms per molecule; and suitability for formulation to permit efficient labeling of many cell types. Preferred fluorocarbon imaging reagents include, linear or cyclic perfluoroethers (e.g., perfluoro-crown ethers). Preferred perfluoro-crown ethers include perfluoro-15-crown-5, perfluoro-18-crown-6 and perfluoro-12-crown-4. In certain embodiments, the fluorocarbon imaging reagent is a perfluorinated polyether having an average formula:

XO(Y—O)nZ wherein Y is selected from the group comprising:

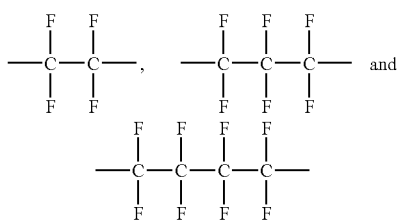

wherein n is an integer from 8 to 20; wherein X and Z are the same and are selected from the group comprising: perfluoroalkyls, perfluoroethers, fluoroalkyls terminated with fluoroacyl, carboxyl, amide or ester, methylols, acid chlorides, amides, amidines, acrylates and esters. In a particularly preferred embodiment, n is 10-12, most preferably 11. In a further embodiment, X and/or Z are polyethers that are terminated with a group (e.g. a carboxyl group) that facilitates the addition of further moieties. Optionally, the imaging reagent comprises an additional functional moiety. The additional functional moiety may be a detection moiety that facilitates detection of the reagent by a technique other than a nuclear magnetic resonance technique. Examples of detection moieties include fluorescent detection moieties and PET detection moieties. Accordingly, the disclosure provides linear fluorocarbons derivatized at one or more polymer ends with at least one functional moiety, wherein at least one functional moiety is selected from the group comprising: a detection moiety, a hydrophilic moiety, a targeting moiety and a cellular uptake moiety. The incorporation of a detection moiety creates a dual (or higher order) labeling moiety that facilitates detection by more than one technique (e.g., PET and MRI or fluorescence microscopy and MRS). Optionally, an imaging reagent may be formulated as an emulsion. Preferred emulsions will be stable at body temperature (37° C. for humans) and at a storage temperature, such as 4° C. or room temperature (20-25° C.). Preferably an emulsion is designed to facilitate uptake of the imaging agent by the subject cells. An emulsion may have an average particle (or droplet) size of between 10 and 500 nm in diameter (meaning that the emulsion may contain particles smaller than 10 nm in diameter or larger than 500 nm in diameter, but having an arithmetical mean particle diameter falling between 10 and 500 nm, as calculated by methods known in the art). In one embodiment the average particle diameter of the emulsion will be between 30 and 300 nm or between 30 and 200 nm less than 20, 10, or 5 nm. Preferably, the average particle diameter of the emulsion will be 90-120 nm or 100-110 nm±less than 80, 40, 20, 10, or 5 nm.

In certain aspects, the disclosure provides methods for detecting a cell in a subject. A method may comprise: administering to the subject a cell that is labeled with a fluorocarbon imaging reagent and examining at least a portion of the subject by a nuclear magnetic resonance technique. Such analysis may include MRI or MRS, which may include collecting data for and generating an image of $^{19}$F distribution. Imaging may also include collecting data for and generating a conventional anatomical $^{1}$H image. In a preferred embodiment, $^{19}$F and $^{1}$H images are generated and compared, optionally by superposition or overlay. Optionally, labeled cells may be detected using $^{19}$F MRS. In a preferred embodiment a conventional anatomical $^{1}$H image is used as a template to guide the positions of one or more localized voxels for $^{19}$F MRS. NMR data is understood to include both raw and processed data.

In certain aspects, the disclosure provides a method for quantifying cell number in vivo. A method may comprise administering to a subject, cells that are labeled with a fluorocarbon imaging reagent; and examining at least a portion of the subject by a nuclear magnetic resonance technique, thereby detecting labeled cells in the subject; and quantifying the number of labeled cells in a region of interest (ROI). In certain embodiments the disclosure provides a method for quantifying labeled cells in a recipient of a transplant that includes labeled cells.

Calibrating the mean "cellular dose" of labeling agent of a particular cell population may be a pre-requisite for in vivo quantitative determinations. The in vivo equivalent of the cellular dose will be referred to as the number of $^{19}$F molecules (F's) per cell or cell quantity, but is understood to be any measure of the amount of label per cell in vivo. In certain embodiments the mean number of $^{19}$F molecules (F's) per cell or cell quantity of a labeled cell population is first measured (i.e., calibrated) in vitro prior to administration of cells to the subject or transplantation. In certain embodiments the mean number of $^{19}$F molecules (F's) per cell or cell quantity of a labeled cell population is measured (i.e., calibrated) contemporaneously with examination of labeled cells. In certain embodiments the mean number of $^{19}$F molecules (F's) per cell or cell quantity of a labeled cell population is calibrated after the labeled cells have been examined. In certain embodiments the mean number of $^{19}$F molecules (F's) per cell or cellular dose of a labeled cell population is calibrated in a test population of cells of a particular type, not necessarily destined for a patient, but used to calibrate cellular dose of labeling agent as a consequence of a particular labeling protocol or set of conditions; the value of cellular dose is then used to for future labeling and in vivo imaging experiments in the same population type of cells with the same labeling protocol. In certain embodiments the cellular dose or cell quantity of labeling agent is assayed using a variety of quantitative techniques, for example using the integrated area of a $^{19}$F NMR spectrum of a cell pellet of a known number of labeled cells. Besides $^{19}$F NMR, many other quantitative methods can be used to assay the cell quantity or cellular dose of the labeling reagent, as described herein. In certain embodiments, the cell quantity or cellular dose can be represented or deduced from prior data. In certain embodiments, the cellular dose or cell quantity may not be directly counted in $F^{19}$ molecules, but the units of the cellular dose of labeling reagent will be representative of this and will be understood to be equivalent.

In certain embodiments, quantifying includes using a calibrated $^{19}$F signal in the ROI. A calibrated $^{19}$F signal is a signal that, by virtue of any of the various calibration techniques described herein, or other techniques that will be apparent from this description, is such that one can deduce a relationship between the signal and the representative number of $^{19}$F molecules or cell quantity. As an example, calibration may be achieved by placing a vial of known quantity of $^{19}$F molecules in the MRI detection field during imaging of the ROI. This permits one to calculate the relationship between the signal strength within the ROI and the number of $^{19}$F molecules.

In certain embodiments, the disclosure provides a method of quantifying the numbers of labeled cells in vivo within an ROI. For example, following cell administration, and in vivo $^{19}$F MRI/MRS, one can compare the total (e.g. integrated) $^{19}$F signal intensity in an ROI to a calibrated $^{19}$F reference. The $^{19}$F reference may be, for example, a vessel containing a solution with a known concentration of $^{19}$F nuclei. The vessel would be placed preferably externally or alongside, or optionally inside, the imaged subject or patient prior to data acquisition. In preferred embodiments, the reference is imaged along with the subject in the same image field of view. Optionally, the reference can be imaged in a separate scan, or no external reference can be used.

By computationally manipulating or combining a key set of parameters from the $^{19}$F MRI/MRS data set, one can calculate the number of labeled cells present in an ROI as described herein. For example, a key set of parameters may include: (i) the cellular dose of labeling agent (i.e., Fc) measured in vitro; (ii) in vivo $^{19}$F MRI/MRS data set taken in the subject at one or more time points following labeled cell administration; (iii) the voxel volume; (iv) the in-plane voxel area (i.e., area of the image pixel); (v) optionally, the MRI/MRS data set from the $^{19}$F reference standard; (vi) optionally, the measured Johnson noise of the $^{19}$F MRI/MRS data in the subject material; (vii) optionally, the measured signal-to-noise ratio (SNR) of one or more voxels of the $^{19}$F MRI/MRS data set in the subject material; (viii) optionally, the measured SNR of one or more voxels of the $^{19}$F MRI/MRS data set from the reference standard; (ix) optionally, the $^{19}$F NMR relaxation times (T1, T2, and T2*) of the subject material; (x) optionally, the $^{19}$F NMR relaxation times (T1, T2, and T2*) of the reference standard (for example, see *Magnetic Resonance Imaging, Third Edition*, chapter 4, editors D. D. Stark and W. G. Bradley, Mosby, Inc., St. Louis Mo. 1999). Those skilled in the art can derive other parameters, combinations of the above set, or derivations thereof, particularly from the $^{19}$F MRI/MRS dataset, that can be used to quantify the number of labeled cells in situ. In certain embodiments the above set of key parameters can be used to derive quantitative or statistical measures of the accuracy or confidence of the measured number of labeled cells.

There are many ways to combine the key parameters (i-x, above), any subsets of these, or any of their combinations or approximations, to estimate the effective number of labeled cells seen by $^{19}$F MRI in the subject material, denoted by $N_c$. For example, one can use an equation of the form $$N_c = \frac{[F_R]v}{I_R} \frac{1}{F_c} \sum_{i=1}^{N_{ROI}} I_c^{(i)}$$

where: $N_c$=total number of labeled cells in the ROI; $[F_R]$=concentration of $^{19}$F in the calibrated $^{19}$F reference solution (or gel); v=voxel volume; $I_R$=mean intensity of the calibrated $^{19}$F reference taken with the MRI/MRS scan, averaged over one or more voxels; $F_c$=average $^{19}$F cellular dose of the labeling agent measured in vitro; $N_{ROI}$=number of voxels in the ROI containing labeled cells; $I_c^{(i)}$=image intensity of the $i^{th}$ voxel in the ROI containing labeled cells; i=unitless index for voxels in the ROI containing labeled cells.

In certain aspects, the disclosure provides a calculating system for the quantification of $^{19}$F labeled cells and optionally; a statistical measure of the uncertainty in the measured cell number. In certain embodiments the disclosure provides a computer; a computer readable medium, operatively coupled to the computer, and computer readable medium program codes that can quantify the number of $^{19}$F labeled cells in a ROI in vivo. In certain embodiments the system calculates the number of labeled cells by ratios of the intensity of $^{19}$F signal and the volume of labeled cells in a ROI compared to a reference. In certain embodiments the system calculates the number of labeled cells according to a formula, an example of which is stated above. In certain embodiments the quantification comprises relating a calibrated NMR signal to a cellular dose.

In certain aspects, the disclosure provides a computer readable medium having computer readable program codes embodied therein for performing in vivo quantification of $^{19}$F labeled cells and optionally, a statistical measure of the uncertainty in the measured cell number. In certain aspects the computer readable medium program codes calculate the number of $^{19}$F labeled cells in a ROI detected by a magnetic resonance technique. In certain embodiments the system calculates the number of labeled cells by ratios of the intensity of $^{19}$F signal and the volume of labeled cells in a ROI compared to a reference. In certain embodiments the system calculates the number of labeled cells according to a formula. In certain embodiments the same computer can be used to calculate a statistical confidence coefficient accompanying the cell number calculation. In certain embodiments the quantification comprises relating a calibrated NMR signal to a cellular dose.

As will be apparent from this disclosure, methods described herein will be useful in a variety of clinical procedures. For example, the disclosure provides methods for detecting donor cells in a recipient, such as a transplant recipient or a recipient of other types of cell-based therapy. Such a method may comprise administering cells for transplant to a transplant recipient, at least a portion of which cells for transplant are labeled with a fluorocarbon imaging reagent; and examining at least a portion of the subject by a nuclear magnetic resonance technique, thereby detecting the labeled cells. Detection of the labeled cells may be done once or repeatedly and may be performed so as to provide information about the location and trafficking of labeled cells in the transplant recipient. Examples of cell recipients include recipients of bone marrow transplants (or cellular fractions containing hematopoietic stem cells, commonly but not exclusively derived from bone marrow, peripheral blood or cord blood) and other cell or organ transplant recipients. Organ transplant recipients include recipients of donor organs such as liver, heart, lung, kidney, pancreatic tissue, neural tissue or other transplants. Recipients also include recipients of donor cells, which may be derived directly from a donor (in the case of autologous cells, the "donor" is the same individual as the recipient) or subjected to limited or extensive culturing prior to use. Donor cells may be derived from essentially any tissue that serves as a source of useful cells, and may include stem cells (including precursor cells), such as hematopoietic stem cells, hemangioblasts, hepatic stem cells, neural stem cells, muscle stem cells (e.g. satellite cells), cardiomyocyte precursor cells, pancreatic stem cells, vascular endothelial precursor cells, mesenchymal stem cells, bone or cartilage precursor cells, or may include mature cells, such as dendritic cells, immune cells (e.g., T cells, B cells), chondrocytes, osteoblasts, and the like. Cells for administration may be autologous, heterologous or even derived from another organism, such as a pig. Other aspects of the present invention will be apparent from the disclosure below.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 8. Fluorescence micrographs of histological sections of pancreatic tissue from a NOD SCID mouse receiving PFPE labeled T cells. Mice received $4\times10^6$ labeled BDC2.5 T cells 48 hours prior. The fixed section staining is as follows: insulin is stained green, nuclei white, actin blue, and T cells red. The images show early insulitis, with T cells infiltrating into the islets or around blood vessels, suggesting that PFPE labeling does not impair T cell trafficking.

DETAILED DESCRIPTION

1. Overview

Figure 1:
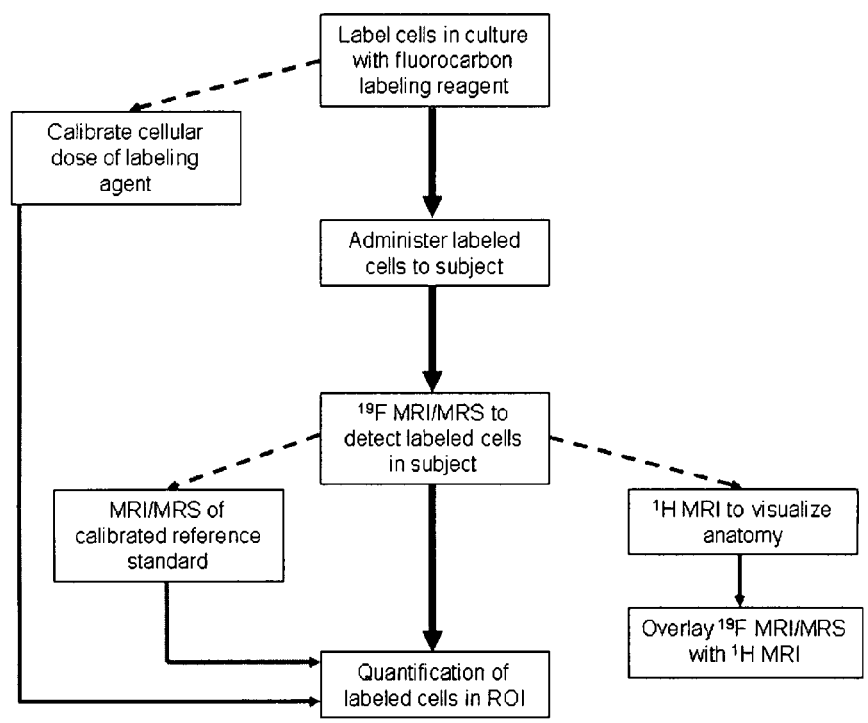
FIG. 1. Schematic diagram of pathway for cell labeling, imaging, and quantification. The dashed connections denote optional steps.

In certain aspects, the disclosure provides novel methods and reagents for labeling cells ex vivo with a nuclear magnetic resonance imaging reagent, such as a fluorocarbon imaging reagent and quantifying the labeled cells in vivo or ex vivo. Labeled cells may be detected by a $^{19}$F nuclear magnetic resonance technique (e.g., MRI/MRS) and quantified according to methods described herein. $^{19}$F nuclear magnetic resonance techniques are excellent imaging tools for biological systems because of the absence of endogenous background signals. Fluorine is present, if at all, at exceedingly low levels in living organisms, and generally not in a chemical form that is detectable by liquid-state nuclear magnetic resonance techniques. This is quite distinct from conventional $^1$H MRI which, while providing visualization of fine anatomical detail, does not permit selective detection of particular cell populations. Certain methods disclosed herein permit whole or partial body screening to visualize the distribution of labeled cells in a living subject. The precise anatomical location of labeled cells detected by $^{19}$F nuclear magnetic resonance may be determined by, for example, superimposition of a $^1$H MRI image that provides anatomical detail. In preferred embodiments, the $^1$H image is acquired during the same imaging session as the $^{19}$F image (without moving the subject) to ensure registration. Additionally, the nuclear magnetic resonance techniques disclosed herein may be applied effectively in ex vivo contexts, as in the case of tissue samples, excised organs and cell cultures. The imaging technology disclosed herein may be applied to a large number of biological and medical problems.

It certain aspects, a method of the invention may comprise labeling cells ex vivo with a $^{19}$F imaging reagent, administering the labeled cells to a subject, and detecting labeled cells in the subject. The cells to be labeled may be a crude cellular fraction or tissue sample, or the cells may be cultured and/or subjected to enrichment prior to labeling. For example, particular cell types may be selected by fluorescence activated cell sorting (FACS) prior to labeling. Other sorting or selective enrichment methods are known in the art for the various different cell types that may be of interest. The types of cells that are labeled may also be controlled by the nature of the imaging reagent. For example, simple colloidal suspensions of imaging reagent will tend to be taken up more quickly by cells with phagocytic activity. As another example, an imaging reagent may be formulated with or covalently bound to a targeting moiety that facilitates selective targeting of the imaging reagent to a particular population of cells. Imaging reagents are described further below. After labeling, cells may be immediately administered or the cells may be stored, further cultured, purified, enriched, segregated or processed in any way that is not incompatible with the intended use of such cells.

In certain aspects, labeled cells will be administered for a therapeutic purpose. Technology described herein may be used for monitoring the trafficking of cellular therapeutics in vivo or in any other desired milieu, such as a tissue explant. Bone marrow cell transplants have been widely used for many years in recipients of ablative therapies for cancers. Various purified cell populations have also been used in place of bone marrow, such as cell populations enriched for hematopoietic stem cells; for example cells may be harvested from umbilical cord blood or peripheral blood. After entering the bloodstream, the stem cells generally travel to the bone marrow, where they begin to produce new white blood cells, red blood cells, and platelets. This engraftment usually occurs within about 2 to 4 weeks after transplantation. Traditionally, engraftment is monitored by testing blood counts on a frequent basis, and complete recovery of immune function generally requires several months (for autologous transplant recipients) to years (for patients receiving allogeneic or syngeneic transplants). Cell sampling by bone marrow aspiration can provide further information on the function of the transplanted cells. These monitoring techniques may be enhanced by ex vivo labeling of the cells to be transplanted (or some small fraction of such cells), thus permitting non-invasive monitoring of the location and movement of transplanted cells by nuclear magnetic resonance techniques. Non-myeloablative allogeneic transplantation (i.e. reduced-intensity transplant) is a similar cell therapy that can be effective for treating several types of cancer. Generally, this technique relies on a lower dose of radiation and/or chemotherapeutic and a limited graft-versus-host disease (the action of immune cells from the transplant against any residual host cancer cells) to provide sufficient anti-cancer activity, as well as the hematopoietic potential of the graft cells to restore the patient's hematopoietic system. As with a traditional ablative graft, the techniques of the present invention may be used to monitor the locations and movements of graft cells in a non-myeloablative allogeneic transplantation.

Cellular therapeutics are also in development for use in the delivery of therapeutic proteins. In one embodiment, cells can be isolated, grown in quantity ex vivo and then implanted to produce and secrete soluble factors, which may be active either locally (e.g. enzymes, cytokines, and neurotransmitters) or at a distance (e.g. hormones and growth regulators). Cells may also be administered to a patient in order to accomplish complex therapeutic purposes, such as reconstitution of tissues, organs, or immune responses based on their ability to home to specific sites within the body, exit from the circulation, and integrate into surrounding tissue or differentiate to replace damaged tissue. Stem cell therapies have also been proposed for myriad diseases including neurological disorders, particularly those characterized by cell death (e.g., Parkinson's disease, stroke and brain injury caused by trauma), cardiovascular disorders (e.g., myocardial infarction), muscle regeneration (e.g., in patients suffering from cachexia or other wasting disorders), pancreatic regeneration in diabetes, liver regeneration, etc. In each instance, cells, or a subpopulation thereof, may be labeled with an imaging reagent ex vivo prior to administration, thus allowing the monitoring of these cells in vivo. In vivo monitoring by a nuclear magnetic resonance technique may be useful, for example, to evaluate the viability of the administered cells. A doctor may tailor a dosing schedule depending on the degree to which labeled cells are detected in a patient after administration. In vivo monitoring may also be useful in determining whether therapeutic cells have localized to a desired location. In general, it will be possible to investigate correlations between the migration behavior of therapeutic cells in vivo, as well as the number and/or survivorship of therapeutic cells in vivo, and therapeutic outcomes. When such correlations have been established, the in vivo imaging of therapeutic cells may be used as a prognostic indicator that may be helpful in selecting the appropriate dosage, administration modes and additional therapeutic interventions that will benefit the patient. Certain imaging advances of the invention will benefit a broad range of cellular therapeutic strategies because these imaging methodologies will be able to detect when, where and if the therapeutic cells have been delivered to the desired targets in vivo. Additionally, the detection of labeled cells may be enhanced by quantification of labeled cells in a ROI, such as a particular organ or tissue.

One example of an application of technology disclosed herein is in tracking dendritic cells (DCs). DCs are known to be the most efficient antigen presenting cells and have the capacity to stimulate naive T cells to initiate an immune response. Because DCs are the most potent stimulators of immune response in the body, DCs represent a possible therapeutic approach to increasing the "visibility" of tumors to a patient's immune system. DCs are the focus of tumor vaccines in development. Varying methods are used to expose the dendritic cells to tumor antigens ex vivo, after which educated dendritic cells are reinfused to stimulate development of T-cell mediated tumor killing. Data applying an embodiment of the present disclosure to the labeling and tracking of DCs and other cell types, presented in WO2005072780, is incorporated by reference herein.

In addition to DCs, other cell types have demonstrated promise for immunotherapy in cancer and other diseases such as diabetes, although their progress has been hampered by many factors, including the inability to observe their movement following transplantation into animals and humans. Natural killer (NK) cells, when harvested, treated ex vivo, and transplanted, have demonstrated the ability to kill metastatic tumor cells. Additional cell types treated ex vivo and transplanted to promote cancer immunity include lymphokine-activated killer (LAK) cells, tumor-infiltrating lymphocytes, and activated killer monocytes. Transplantation of T cells, which are white blood cells that attack pathogenic cells, has demonstrated promise against a variety of cancers, including pancreatic cancer, in which clinical trials are beginning, and against multiple sclerosis and HIV infection.

In certain aspects, labeled cells are administered to a subject for non-therapeutic purposes. For example, cells may be labeled ex vivo, administered to a subject and then detected, with the expectation that the labeled cells will behave similarly to like, unlabeled cells in vivo and may therefore be used to monitor the behavior of endogenous cell populations. Monitoring may be used for the purpose of tracking movements of cells, particularly in the case of cells that are known to be highly mobile, such as cells of the immune system, many types of stem cells and blood born cells. Monitoring may also be used for the purpose of tracking viability or adherence of non-mobile cells at the site of implant. Cells of many tissues, such as muscle, liver, pancreas, kidney, brain or skin will tend to be relatively stationary, but disappearance of label may indicate a high death rate, low adherence, or other information. Modern cell culture and sorting techniques allow the selective pooling and labeling of virtually any desired cell population, including various stem cell types, immune cell types, and other blood cell types. For example, cell surface markers can be used to sort mixed populations of cells to purify a population of interest. As described in the examples below, both T cells and dendritic cells may be labeled ex vivo and detected in vivo.

As an example, labeled immune cells may be used as detectable proxies for the movements of immune cells in a patient. Immune cells participate in and are markers for a host of inflammatory and autoimmune disorders, as well as cancer and atherosclerotic plaque formation. As a general methodology, any process involving the recruitment of immune cells may be detected in a patient by administering to the patient labeled immune cells. The accumulation of label in a particular area provides an indication of the degree of immune response occurring in that portion of the body. Traditionally, these types of studies involve histological techniques that are incompatible with living subjects. Certain methods of the disclosure may facilitate the development of therapeutic strategies for the treatment of human diseases. The ability to track selected populations of immune cells non-invasively, and without the use of radioisotopes, can impact many areas of basic and clinical immunology, such as multiple sclerosis, diabetes, monitoring organ transplant rejection, and cancer. For instance, tumors are often highly infiltrated by immune cells. Labeled cells may be imaged in a subject to reveal the location of a tumor, and in some instances may be useful as a non-invasive detection screen. Early detection of cancers has been a critical problem, as most early stage cancers are readily treated by surgery without resort to debilitating chemotherapeutic agents. Likewise, the progress of other inflammatory diseases may be monitored by tracking the dynamics of immune cells in the patient. The effectiveness of immunosuppressant therapy may be assessed as well. In the instance of an organ transplant recipient, the recipient could receive a dose of labeled immune cells prior to receiving the transplantation. In vivo monitoring of the accumulation of immune cells in the transplant could then be used as an early warning sign of rejection. In the case of transplants, the methods disclosed herein are particularly desirable because the alternative, biopsies, are well-known to increase the risk of organ rejection.

As an additional example, cells for use in a bone marrow cell transplant, or a peripheral blood stem cell transplant, may be labeled ex vivo as described herein, administered, and monitored in vivo by a nuclear magnetic resonance technique. Such monitoring may be used to evaluate the engraftment of donor cells in the recipient bone cavities, as well as survivorship and movement of labeled cells in the recipient. A physician can use information relating to the trafficking of donor cells in a recipient as an early indication of the likely success or failure of the procedure. This type of early detection will allow physicians to tailor the post-transplant therapeutic regimen accordingly. Another cellular cancer therapeutic where the detection technology can be applied is the allogeneic non-myeloablative, or reduced intensity transplant. This procedure may be used with a donor lymphocyte infusion to boost graft-versus-tumor effect which destroys cancer cells. Here the entire population, or a fraction, of transplanted cells could be labeled before infusion. A nuclear magnetic resonance technique could then be used determine where the cells traffic to in the body, which can be indicative of the efficacy of the procedure. As it is often desirable to limit the dose of allogeneic cells to minimize rejection, the cell's trafficking pattern may be used to calibrate dose. In the above cancer cell therapies it may be desirable to selectively label one or more sub-population of the transplanted cells (e.g., CD34+ stem cells or T cells) that are believed to have therapeutic efficacy.

As a further example, cells involved in formation of new tissue, such as in angiogenesis, can be labeled, administered to a subject, and detected to identify hotspots of tissue formation. For example, smooth muscle cells and/or endothelial precursor cells may be labeled and introduced into the bloodstream. Such cells are expected to accumulate at sites of angiogenic activity. Angiogenic activity may be associated with physiological and pathological events such as menstrual cycling, early pregnancy, collateral vessel formation in response to arterial blockages, tumor development and wound healing. Similarly, cells involved in wound healing, such as fibroblasts, may be labeled and administered systemically or to a site of suspected injury in order to monitor cellular behavior.

For example, a medicament or delivery device containing labeled cardiomyocyte lineage cell aggregates or cells derived therefrom may be provided for treatment of a human or animal body, including formulations for cardiac therapy. Cardiomyocyte lineage cells may be administered to a patient in a method for reconstituting or supplementing contractile and/or pacemaking activity in cardiac tissue (see US Patent Application No. 20060040389, 20050112104, 20050244384, which are incorporated in their entirety herein).

In accordance with the present invention labeled cardiomyocyte lineage cells are used to regenerate or repair striated cardiac muscle that has been damaged through disease or degeneration. The labeled cardiomyocyte lineage cells integrate with the healthy tissue of the recipient to replace the function of the dead or damaged cells, thereby regenerating the cardiac muscle as a whole. Cardiac muscle does not normally have reparative potential. The labeled cardiomyocyte lineage cells are used, for example, in cardiac muscle regeneration for a number of principal indications: (i) ischemic heart implantations, (ii) therapy for congestive heart failure patients, (iii) prevention of further disease for patients undergoing coronary artery bypass graft, (iv) conductive tissue regeneration, (v) vessel smooth muscle regeneration and (vi) valve regeneration.

The administration of the cells can be directed to the heart, by a variety of procedures. Localized administration is preferred. The mesenchymal stem cells can be from a spectrum of sources including, in order of preference: autologous, allogeneic, or xenogeneic. There are several embodiments to this aspect, including the following. The present invention allows monitoring of the progress of these cell in vivo.

The cardiomyocyte lineage cells may be cardiomyocyte precursor cells, or differentiated cardiomyocytes. Differentiated cardiomyocytes include one or more of primary cardiomyocytes, nodal (pacemaker) cardiomyocytes; conduction cardiomyocytes; and working (contractile) cardiomyocytes, which may be of atrial or ventricular type. In certain embodiments, cells come from a muscle sample (or other sample) that contains muscle progenitor cells such as satellite cells (see US Patent Application No. 20050244384). In certain embodiments, cells are mesenchymal stem cells (MSCs) (see US Patent Application No. 20050112104).

A "cardiomyocyte precursor" is defined as a cell that is capable (without dedifferentiation or reprogramming) of giving rise to progeny that include cardiomyocytes. Such precursors may express markers typical of the lineage, including, without limitation, cardiac troponin I (cTnI), cardiac troponin T (cTnT), sarcomeric myosin heavy chain (MHC), GATA4, Nkx2.5, N-cadherin, .beta.1-adrenoceptor (.beta.1-AR), ANF, the MEF-2 family of transcription factors, creatine kinase MB (CK-MB), myoglobin, or atrial natriuretic factor (ANF).

In certain instances, cells may prove to be so thoroughly associated with a biological site or structure of interest that the labeled cells may be administered for the sole purpose of aiding in the visualization of such a structure. As mentioned above, immune cells characteristically infiltrate tumors. Accordingly, labeled immune cells may be administered for the purpose of visualizing tumors.

Technology disclosed herein may be applied to studies of animal models of human diseases. Various animal models of diseases may evince altered dynamics or survival of one or more cell populations. Such cell populations may be labeled, administered to the animal and monitored. For example, the infiltration of immune cells into the pancreas of the NOD mouse model for diabetes may be monitored. Other examples of animal models include: experimental allergic encephalomyelitis (multiple sclerosis model), gliosarcoma tumor models, and organ-transplant rejection. By tracking phenotypically-defined populations of immune cells in these models, one can elucidate aspects of the disease etiology and monitor how cell trafficking is affected by therapeutics. This method may be used, for example, to screen for drugs that have a desired effect in an animal model. A drug screening assay may comprise administering labeled cells to an animal and detecting the cells in vivo in the presence of a test agent. Changes in cell behavior that are correlated with the presence of the test agent may be indicative of a therapeutic effect. Such changes may be detected by comparison to a suitable reference, including, for example, the same animal before and after treatment with the test agent or a separate, untreated animal. In addition to a test agent, the methods may be used to evaluate the effects of test conditions, such as an exercise regimen, injury, genetic alteration, etc. As an example, it is expected that a drug for treatment of an autoimmune disease would decrease the tendency of immune cells to accumulate in an affected tissue. In addition to steady state evaluations, methods disclosed herein may be used to evaluate kinetic properties of cells, such as the rate at which cells arrive at a particular site and the time of signal persistence at a site. Drug screening assays may be particularly powerful when combined with in vivo monitoring of tightly defined cell populations, such as certain groups of immune cells that are implicated in various disorders. For example, monitoring of labeled cytotoxic T cells may be particularly useful in identifying drugs that may be useful in preventing transplant rejection. The ability to monitor cells in vivo provides a powerful assay that may be applied to the analysis of essentially any experimental animal, including, for example, any of the various transgenic or otherwise mutant mice that have been generated.

Several groups have studied labeling and visualizing immune cells using MRI contrast agents. Other researchers have used MRI contrast agents to label cell types such as stem cells and neuronal precursors. The majority of these studies render the cells magnetically-distinct via the incorporation superparamagnetic iron-oxide (SPIO) agents. Cells labeled with contrast agents incorporating other types of metal ions, particularly gadolinium and manganese have also been used. In studies utilizing these metal-ion based agents, the compounds are not directly imaged; instead, one observes their indirect effect on surrounding waters. The presence of the agent tends to shorten the relaxation times ($T_1$, $T_2$, or $T_2^*$) of water in proximity to the compound; these effects can be detected in relaxation time-weighted images. SPIO agents, for example, impart contrast to conventional $^1H$ images by locally perturbing the magnetic field experienced by the nearby mobile water molecules, which in turn modulates $T_1$, $T_2$, or $T_2^*$. Methods described herein are distinctly different from all methods using metal ion based contrast agents because signals from $^{19}F$ nuclei in the imaging reagents may be directly detected and, optionally, imaged.

An inherent drawback to detecting labeled cells using metal-ion based contrast agents is that one is often in a situation where it is necessary to interpret subtle changes in grayscale contrast in regions that are believed to contain labeled cells. The large $^1H$ background signal from the high concentration of mobile water present in tissues can make it difficult to unambiguously identify regions containing labeled cells; this is especially problematic if the labeled cell biodistribution is not known a priori. The results of a 'snapshot' image are often ambiguous as to whether labeled cells are present in a specific tissue. This is a particularly vexing problem when trying to detect SPIO labeled cells in iron-laden organs that intrinsically appear dark in anatomical ($T_2$- or $T_2^*$-weighted) images, such as in the liver or the spleen. Often one must resort to detecting the time-lapse image intensity changes in a particular organ over a period of several hours to verify that labeled cells have accumulated. Furthermore, quantification of labeled cells in vivo in regions of interest using metal-ion based contrast agents is problematic, and there is generally no simple and reliable way to do this using relaxation-time weighted MRI or by using quantitative relaxation-time MRI maps.

Thus the methods and compositions disclosed herein provide much needed tools in the fields of medicine and biology.

2. Imaging Reagents and Formulations

The imaging reagent used in the subject methods is a fluorocarbon, i.e., a molecule including at least one carbon-fluorine bond. By virtue of the $^{19}F$ atoms, the imaging reagents disclosed herein may be detected by $^{19}F$ MRI and other nuclear magnetic resonance techniques, such as MRS techniques. In certain preferred embodiments, a fluorocarbon imaging reagent will have one or more of the following properties: 1) reduced cytotoxicity; 2) a $^{19}F$ NMR spectrum that is simple, ideally having a single, narrow resonance to minimize chemical shift artifacts; 3) high sensitivity with a large number of NMR-equivalent fluorine atoms in each molecule; 4) formulated to permit efficient labeling of many cell types and not restricted to phagocytic cells.

Exemplary compounds include aryl or heteroaryl trifluoromethyl sulfonic acid esters (triflates) or sulfonamides (triflamides), esters of fluorinated alcohols (such as 2,2,2-trifluoroethanol, perfluoro-tert-butanol, and 2,2,3,3,3-pentafluoropropanol), esters and amides of perfluoroalkanoic acids (such as trifluoroacetic acid, perfluorotetradecanoic acid, and nonafluoropentanoic acid), ethers of perfluoroalkanes, and the like. Preferably, the imaging reagent comprises a plurality of fluorines bound to carbon, e.g., greater than 5, greater than 10, greater than 15 or greater than 20 fluorines bound to carbon. Preferably, at least 4, at least 8, at least 12 or at least 16 of the fluorines have a roughly equivalent NMR chemical shift.

In certain embodiments, the imaging reagent is a perfluoro crown ether, such as perfluoro-15-crown-5, perfluoro-18-crown-6, perfluoro-12-crown-4, etc., also referred to herein as cyclic perfluoropolyethers (cyclic PFPEs). Such compounds are advantageous in that the $^{19}F$ nuclei of these molecules will have similar or identical NMR resonances, resulting in a higher signal-to-noise ratio image with an absence of chemical-shift image artifacts. The macrocycle perfluoro-15-crown-5 ether has particularly preferable characteristics. It is neither lipophilic nor hydrophilic, which is typical for perfluoropolyethers, and is emulsified into aqueous solution. Typical emulsions are small particulates (~10-500 nm diameter) that are stable in aqueous solution and can be taken up by cells. One of skill in the art will recognize, that other fluorinated compounds will have desirable properties, particularly those fluorinate compounds in which each fluorine atom is in a similar chemical environment. Esters of perfluoro-tert-butanol, 1,3,5-tris(trifluoromethyl)benzene, hexafluoroacetone, poly(trifluoromethylethylene), and perfluorocyclohexane are examples of compounds having multiple fluorine atoms with $^{19}F$ resonances that have the same, or nearly the same, Larmor frequencies.

In certain embodiments, the imaging reagent is a polymer. In certain embodiments, the imaging reagent is or includes a linear perfluoropolyether (linear PFPE), e.g., a compound having a structure or portion thereof comprising repeated units of —[O—CF$_2$(CF$_2$)$_x$CF$_2$]$_n$—, where x is an integer from 0 to 10, preferably from 0-3, and n is an integer from 2 to 100, preferably from 4 to 40. Perfluorinated linear polyethylene oxide, for example, can be obtained from Exfluor Corp. (Round Rock, Tex. Either or both ends (or a plurality of ends, in the case of branched polymers) may be derivatized with a moiety that provides an additional desired functionality. For example, an imaging reagent may have a formula of A-B-C, where A and/or C may be a functional moiety and B comprises repeated units of —[O—CF$_2$(CF$_2$)$_x$CF$_2$]$_n$—, where x is an integer from 0 to 10, preferably from 0-3, and n is an integer from 2 to 100, preferably from 4 to 40. Functional moieties (e.g., non-fluorinated monomers conferring a particular desired function) are discussed further below.

A linear perfluoropolyether may also be described as a composition having the average formula:

wherein Y is selected from the group comprising:

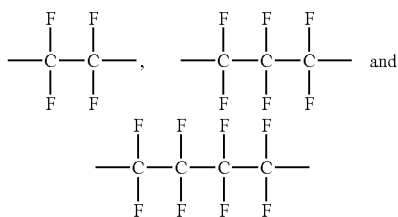

wherein n is an integer from 8 to 30; wherein X and Z are the same and are selected from the group comprising: perfluoroalkyls, perfluoroethers, fluoroalkyls terminated with fluoroacyl, carboxyl, amide or ester, methylols, acid chlorides, amides, amidines, acrylates and esters, as well as any of the preceding derivatized with a functional moiety.

While a completely fluorinated polymer can be formed, for example, by reacting a perfluorinated diacid with a perfluorinated dihalocarbon (such as 1,4-diiodooctafluorobutane), fluorinated monomers can be reacted with other monomers (optionally functional moieties, which may be non-fluorinated) to form hybrid polymers that are useful as imaging reagents. A variety of different non-fluorinated monomers can be used to vary the chemical and physical properties of the overall polymer, and make it possible to tailor the imaging reagent for specific uses. For example, a highly lipophilic imaging reagent may concentrate in cultured cells that will be destined for a patient as part of a cellular therapeutic.

For labeling cells in culture, the imaging reagents can be employed in one or more of at least three modalities: 1) imaging reagents that are internalized or otherwise absorbed by target cells without the formation of any covalent or other binding association; 2) imaging reagents that covalently attach to target cells; and 3) imaging reagents coupled to molecules, such as antibodies or ligands, that bind to molecules present on the target cells.

Imaging reagents of the first type include the perfluoro crown ethers and other PFPEs that are taken up by cells and, preferably, are retained in the cell without degradation for a substantial period of time, e.g., having a half-life in the cell of at least 1 hour, at least 4 hours, at least about a day, at least about three days, or even at least about a week. For obvious reasons, it is preferred that the imaging reagent not interfere with ordinary cellular functions or exhibit cytotoxicity at the concentrations employed for labeling. As demonstrated herein, perfluoropolyethers show reduced toxic effect on the labeled cells.

Imaging reagents of the second type include electrophilic compounds that react with nucleophilic sites on the cell surface, such as exposed thiol, amino, and/or hydroxyl groups. Accordingly, imaging reagents such as maleimides, alkyl iodides, N-hydroxysuccinimide or N-hydroxysulfosuccinimide esters (NHS or sulfo-NHS esters), acyl succinimides, and the like can form covalent bonds with cell surfaces. Other techniques used in protein coupling can be adapted for coupling imaging reagents to cell surface proteins. See Means et al. (1990) *Bioconjugate Chemistry* 1:2-12, for additional approaches to such coupling.

Imaging reagents of the third type can be prepared by reacting imaging reagents of the second type not with the cells themselves, but with a functional moiety that is a cell-targeting ligand or antibody. Suitable ligands and antibodies can be selected for the application of interest. For example, a ligand that selectively targets hematopoietic cells could be labeled with an imaging reagent as described herein and administered to a patient, such as by injection.

Alternatively, an imaging reagent can be coupled to an indiscriminate internalizing peptide, such as antepennepedia protein, HIV transactivating (TAT) protein, mastoparan, melittin, bombolittin, delta hemolysin, pardaxin, Pseudomonas exotoxin A, clathrin, Diphtheria toxin, C9 complement protein, or a fragment of any of these. Cells treated with this indiscriminate molecule ex vivo will absorb the imaging reagent. When such labeled cells are implanted into an animal, such as a mammal, the imaging reagent can be used to visualize and/or track the implanted cells by nuclear magnetic resonance techniques.

In one embodiment, the internalizing peptide is derived from the drosophila antepennepedia protein, or homologs thereof. The 60-amino acid-long homeodomain of the homeo-protein antepennepedia has been demonstrated to translocate through biological membranes and can facilitate the translocation of heterologous polypeptides to which it is coupled. See for example Derossi et al. (1994) *J Biol Chem* 269:10444-10450; and Perez et al. (1992) *J Cell Sci* 102:717-722. It has been demonstrated that fragments as small as 16 amino acids long of this protein are sufficient to drive internalization. See Derossi et al. (1996) *J Biol Chem* 271:18188-18193.

Another example of an internalizing peptide is the HIV transactivator (TAT) protein. This protein appears to be divided into four domains (Kuppuswamy et al. (1989) *Nucl. Acids Res.* 17:3551-3561). Purified TAT protein is taken up by cells in tissue culture (Frankel and Pabo, (1989) *Cell* 55:1189-1193), and peptides, such as the fragment corresponding to residues 37-62 of TAT, are rapidly taken up by cell in vitro (Green and Loewenstein, (1989) *Cell* 55:1179-1188). The highly basic region mediates internalization and targeting of the internalizing moiety to the nucleus (Ruben et al., (1989) *J. Virol.* 63:1-8). Peptides or analogs that include a sequence present in the highly basic region can be conjugated to fluorinated imaging reagents to aid in internalization and targeting those reagents to the intracellular milieu.

Another PFPE composition of interest is linear PFPEs (structure shown above) derivatized with a variety of end groups. The linear compounds have the advantage that one can conjugate a variety of functional entities to the end groups, such as functional moieties of various types. The $^{19}$F NMR spectra of these linear compounds generally is more complex than the macrocyclic compounds, but a PFPE with two well-separated NMR signals can also be used. In this case it may be desirable to use an MRI pulse sequence that incorporates one or more off-resonance saturation pulses applied to the smaller resonance to eliminate any chemical shift artifacts.

A particularly useful application of linear PFPEs is the synthesis of a "dual mode" agent that can be detected by $^{19}$F nuclear magnetic resonance techniques and includes a detection moiety that facilitates detection by a second detection method. As an example, a fluorescent moiety attached to the endgroups may be used to generate imaging reagents that can be visualized with $^{19}$F MRI and fluorescence microscopy. A wide range of fluorescent moieties may be used in a dual-mode agent. Many suitable fluorophores are known, including fluorescein, lissamine, phycoerythrin, rhodamine (Perkin Elmer Cetus), Cy2, Cy3, Cy3.5, Cy5, Cy5.5, Cy7, FluorX (Amersham), and Alexa dyes (Molecular Probes). Fluorescent moieties include derivatives of fluorescein, benzoxadioazole, coumarin, eosin, Lucifer Yellow, pyridyloxazole and rhodamine. These and many other exemplary fluorescent moieties may be found in the Handbook of Fluorescent Probes and Research Chemicals (2000, Molecular Probes, Inc.). Additional fluorescent moieties include fluorescent nanocrystals, such as the "quantum dot" products available from Quantum Dot Corporation (Hayward, Calif.). Such nanocrystals may be constructed with a semiconductor core having an appropriate emission spectrum (e.g., CdS, CdSe, CdTe), a shell composed of a non-emissive transparent and relatively non-reactive material that can be efficiently wed to the underlying core material (e.g., ZnS), and a coating that provides desirable solubility (e.g., for solubility in aqueous, physiological solutions) and possible reactive groups for attachment to a fluorocarbon described herein.

Dual mode imaging reagents that permit fluorescent detection are particularly useful in a variety of applications. For example, fluorescent labeling permits the use of fluorescence-based cell sorting mechanisms, such as Fluorescence Activated Cell Sorting (FACS). Cell sorting may be desirable, for example, to enrich for a population of cells that have been successfully labeled. This may be particularly useful where labeling has been directed to rarer cell populations. Dual mode agents are also useful for finding and characterizing labeled cells after they have been implanted into a living subject. In this application, cells may be biopsied, or by some other means harvested, from the subject after they have resided there for some duration. Biological analysis of the harvested cells can then be performed. For example, FACS analysis can be performed on the harvested cells, where after positively selecting cells for the fluorescent PFPE label, the cells can be assayed for the expression of specific cell surface markers (using a different color fluorescent probe) to investigate any change in cell phenotype that occurred following implantation. Fluorescent labels may also be used for fluorescence microscopy of cells, particularly using three-dimensional confocal fluorescence microscopy. Fluorescence microscopy will not generally be useful for in vivo visualization of deep tissues containing labeled cells, but surface tissues may be visualized as well as tissue samples. Dual labeling will be particularly valuable in calibrating and validating any new fluorocarbon-based nuclear magnetic resonance labeling method. Results obtained by, for example, MRI/MRS may be compared to those obtained by fluorescence detection, both in cultured labeled cells (biopsied or otherwise) and in vivo, to the extent possible. A known fluorescence signal strength per unit molecule may be used to calibrate MRI/MRS measurements.

Detection moieties suitable for PET imaging may also be used to create dual mode imaging reagents that are detectable by nuclear magnetic resonance techniques and by PET techniques. For example, the $^{18}$F isotope is a potent label for PET detection methods. A fluorocarbon imaging reagent may comprise a mixture of $^{18}$F and $^{19}$F isotopes, thus providing a dual mode label that is suitable for MRI/MRS and PET. $^{18}$F and $^{19}$F may also be added in separate monomers to form a mixed copolymer, or $^{18}$F portions may be located at either end of a linear polyether, at the position where most other functional moieties would be added. $^{18}$F has no NMR signal and so may be added at positions that would, for example, tend to decrease NMR linewidth, simplify the NMR spectrum, or alleviate chemical shifts from resonances that adversely affect the read-out obtained by a nuclear magnetic resonance technique. In addition, molecules of the fluorocarbon imaging reagents can incorporate other radioisotopes that are effective PET probes, such as $^{11}$C, $^{15}$O, and $^{13}$N. Those skilled in the art can, in view of this specification, devise many other PET-detectable moieties that can be incorporated into or, for example, attached to an endgroup(s), of the imaging reagents of this disclosure.

In certain embodiments, a linear perfluoropolyether may be derivatized with a relatively hydrophilic moiety at one, or preferably, both ends. For example, the hydrophilic moiety may be a polyethylene glycol, thus forming a tri-block copolymer with water-soluble regions on each end and a hydrophobic region in the center. When mixed in an aqueous environment, imaging reagents of this type will tend to form micelles, with the PFPE core surrounded by a water-soluble coat. Amino-PEG blocks are commercially available with a range of molecular weights. Coupling the PFPE core with other groups, such as aliphatic amines and phosphatidyl ethanolamine in place of the hydrophilic sections, will give derivatives with different solubility characteristics (see WO2005072780).

In certain embodiments, the disclosure provides formulations of imaging reagents that are suitable for uptake by cells. Optionally, an imaging reagent may be formulated as an emulsion. For example, in a preferred embodiment, a label formulation comprises a 1:1 molar ratio of PFPE with Pluronic L-35 or F68. Emulsions including a fluorocarbon imaging reagent, such as a PFPE, will preferably have a distribution of particle sizes that allow adequate cellular uptake. In certain embodiments, a uniform particle size may be advantageous. The desired degree of uniformity of particle size may vary depending upon the application. For example, it will generally be desirable that the mean particle size fall within a range from 10 nm to 500 nm, and preferably a range of from 30 nm to 150 nm or a range of from about 350 to 500 nm. Optionally, 25%, 50%, 75% or more of the particles will also fall within the selected range. Particle sizes may be evaluated by, for example, light scattering techniques or by visualizing the emulsion particles using EM micrographs. In certain cell types that have a relatively small amount of cytoplasm, such as most stem cells, preferred particle sizes will be in the range of 10-50 nm in diameter, and optionally 100-200 nm diameter.

Emulsions for use in cells should preferably be stable at a wide range of temperatures. Preferred emulsions will be stable at body temperature (37° C. for humans) and at a storage temperature, such as 4° C. or room temperature (20-25° C.). For example, it will often be desirable to store the emulsion at a cool temperature, in the range of 2-10° C., and preferably 4° C., and then warm the emulsion to room temperature (e.g., 18 to 28° C., and more typically 20 to 25° C.). After labeling of cells, the emulsion will experience a temperature of about 37° C. Accordingly, a preferred emulsion will retain the desired range of particle sizes at temperatures ranging from refrigeration temperatures up to body temperature.

The properties of an emulsion may be controlled primarily by the properties of the imaging reagent itself, the nature of surfactants and/or solvents used, and the type of processing device (e.g., sonicator, Microfluidizer, homogenizer, etc.). Methods for forming PFPE emulsions are extensively described in U.S. Pat. Nos. 5,330,681 and 4,990,283. A continuous phase of a polyhydroxylated compound, such as polyalcohols and saccharides in concentrated aqueous solution may be effective. The following polyalcohols and saccharides have proved to be particularly effective: glycerol, xylitol, mannitol, sorbitol, glucose, fructose, saccharose, maltitol, dimer compounds of glycerol (di-glycerol or bis(2,3-di-hydroxypropyl) ether, solid water soluble polyhydroxylated compounds as sugars and glycerol condensation products as triglycerol and tetraglycerol. The dispersion in emulsion may be performed in the presence of conventional surfactants, including cationic, anionic, amphoteric and non-ionic surfactants, with ionic surfactants being preferable. Examples of suitable surfactants include sodium lauryl sulphate, sulphosuccinate (sulphosuccinic hemiester), coco-amphocarboxyglycinate, potassium cetyl phosphate, sodium alkyl-polyoxyethylene-ether carboxylate, potassium benzalconium chloride, alkyl amidopropyl betaine, cetyl-stearilic ethoxylated alcohol, and sorbitan-ethoxylate(20)-mono-oleate Tween 20. While thermodynamic equations may be used to attempt to predict mixtures of imaging reagents that will give emulsions having the desired particle sizes and stability, it is generally accepted that actual testing of various mixtures will be most effective. The emulsification of mixtures is simple and quick, permitting rapid testing of a wide range of combinations to identify those that give rise to emulsions that are suitable for use in the methods disclosed herein.

Preferably an emulsion is designed to facilitate uptake of the imaging reagent by the subject cells. A surfactant may be designed to form stable emulsions that carry a large quantity of PFPE into the aqueous phase. Additionally, it may have properties that increase the intracellular delivery of the emulsion particles in the shortest possible incubation time. Increasing the PFPE intracellular loading improves sensitivity to the labeled cells. Furthermore, minimizing the culture time can be important when working with the primary cells cultures. The efficiency of intracellular uptake depends on cell type. For example macrophages and some dendritic cells will endocytose almost any particulate, whereas other cell types of interest may only be weakly phagocytic. In either case the uptake efficiency can be boosted substantially by designing the surfactant so that the surface of the emulsion particle has properties that promote cellular uptake in culture (i.e. "self-delivering" emulsion particles). The emulsion particle surface can be made to have lipophilic, or optionally cationic, properties via appropriate surfactant design. For example the surfactant can incorporate lipids, such as cationic lipids, oil-in-water emulsions, micelles, mixed micelles, or liposomes, that tend to bind to or fuse with the cell's surface, thereby enhancing emulsion particle uptake. A preferred colloidal system for use as a delivery vehicle in vitro and in vivo is a liposome (i.e., an artificial membrane vesicle). The preparation and use of such systems is well known in the art. Suitable cationic lipids are described in the following and are herein incorporated in their entirety: Felgner et al., 1987, PNAS 84, 7413-7417; Eppstein et al., U.S. Pat. No. 4,897,355), (Rose, U.S. Pat. No. 5,279,833; Eppand et al. U.S. Pat. No. 5,283,185; Gebeyehu et al., U.S. Pat. No. 5,334,761; Nantz et al., U.S. Pat. No. 5,527,928; Bailey et al., U.S. Pat. No. 5,552,155; Jesse, U.S. Pat. No. 5,578,475). Other approaches include incorporation into the surfactant peptides (e.g. oligo-Arg9 and TAT-like peptides) that facilitate entry into cells, or antibodies that target specific cell surface molecules. Additionally, in certain embodiments, one can incorporate small cationic proteins into the surfactant, such as protamine sulfate, to enhance cellular uptake. Protamine sulfate is non-toxic to cells and has FDA approval for use in humans as a heparin antagonist. In certain embodiments, colloidal dispersion systems are used, such as macromolecule complexes, nanocapsules, microspheres, and beads. Other approaches for enhancing uptake of the emulsified fluorocarbons, such as by using additional transfection agents or by using electroporation of the cells, is described herein.

In preferred embodiments, emulsions have "self-delivering" properties without having to add uptake enhancing reagents. Said emulsions are preferably stable and have a shelf-life of a period of months or years.

It is understood that surfactants and uptake enhancing reagents are not meant to be exclusive groups and in some cases they may be overlapping.

3. Cells and Labeling

Methods described herein may be used with a wide range of cells, including both prokaryotic and eukaryotic cells, and preferably mammalian cells. Technologies for cell preparation include cell culture, cloning, nuclear transfer, genetic modification and encapsulation.

A partial list of suitable mammalian cells includes: blood cells, myoblasts, bone marrow cells, peripheral blood cells, umbilical cord blood cells, cardiomyocytes (and precursors thereof), chondrocytes (cartilage cells), dendritic cells, fetal neural tissue, fibroblasts, hepatocytes (liver cells), islet cells of pancreas, keratinocytes (skin cells) and stem cells. In certain preferred embodiments, the cells to be used are a fractionated population of immune cells. Recognized subpopulations of immune cells include the lymphocytes, such as B lymphocytes (Fc receptors, MHC class II, CD19+, CD21+), helper T lymphocytes (CD3+, CD4+, CD8−), cytolytic T lymphocytes (CD3+, CD4−, CD8+), natural killer cells (CD16+), the mononuclear phagocytes, including monocytes, neutrophils and macrophages, and dendritic cells. Other cell types that may be of interest include eosinophils and basophils.

Cells may be autologous (i.e., derived from the same individual) or syngeneic (i.e., derived from a genetically identical individual, such as a syngeneic littermate or an identical twin), although allogeneic cells (i.e., cells derived from a genetically different individual of the same species) are also contemplated. Although less preferred, xenogeneic (i.e., derived from a different species than the recipient) cells, such as cells from transgenic pigs, may also be administered. When the donor cells are xenogeneic, it is preferred that the cells are obtained from an individual of a species within the same order, more preferably the same superfamily or family (e.g. when the recipient is a human, it is preferred that the cells are derived from a primate, more preferably a member of the superfamily Hominoidea).

Cells may, where medically and ethically appropriate, be obtained from any stage of development of the donor individual, including prenatal (e.g., embryonic or fetal), infant (e.g., from birth to approximately three years of age in humans), child (e.g. from about three years of age to about 13 years of age in humans), adolescent (e.g., from about 13 years of age to about 18 years of age in humans), young adult (e.g., from about 18 years of age to about 35 years of age in humans), adult (from about 35 years of age to about 55 years of age in humans) or elderly (e.g., from about 55 years and beyond of age in humans).

In many embodiments, cells are labeled by contacting the cells with an emulsion of the imaging reagent, such that the reagent is taken up by cells. Both phagocytic and non-phagocytic cells may be labeled by such a method. For example, as demonstrated in WO2005072780, both dendritic cells (phagocytic) and gliosarcoma cells (non-phagocytic) can be labeled by contacting the cells with an emulsion of the imaging reagent.

In certain embodiments the cells to be labeled are stem cells. Stem cell therapies are commonly used as part of an ablative regimen for treatment of cancer with high dose radiation and/or chemotherapeutic agents. Ablative regimens generally employ hematopoietic stem cells, or populations of cells containing hematopoietic stem cells, as may be obtained, for example, from peripheral blood, umbilical cord blood or bone marrow. Cells of this type, or a portion thereof, may be labeled and tracked in vivo to monitor survival and engraftment at the appropriate location. Other types of stem cells are increasingly attractive as therapeutic agents for a wide variety of disorders.

As an example, cells may be mouse embryonic stem cells, or ES cells from another model animal. The labeling of such cells may be useful in tracking the fate of such cells administered to mice, optionally as part of a preclinical research program for developing embryonic stem cell therapeutics. Examples of mouse embryonic stem cells include: the JM1 ES cell line described in M. Qiu et al., Genes Dev 9, 2523 (1995), and the ROSA line described in G. Friedrich, P. Soriano, Genes Dev 5, 1513 (1991), and mouse ES cells described in U.S. Pat. No. 6,190,910. Many other mouse ES lines are available from Jackson Laboratories (Bar Harbor, Me.). Examples of human embryonic stem cells include those available through the following suppliers: Arcos Bioscience, Inc., Foster City, Calif., CyThera, Inc., San Diego, Calif., BresaGen, Inc., Athens, Ga., ES Cell International, Melbourne, Australia, Geron Corporation, Menlo Park, Calif., Göteborg University, Göteborg, Sweden, Karolinska Institute, Stockholm, Sweden, Maria Biotech Co. Ltd.—Maria Infertility Hospital Medical Institute, Seoul, Korea, MizMedi Hospital—Seoul National University, Seoul, Korea, National Centre for Biological Sciences/Tata Institute of Fundamental Research, Bangalore, India, Pochon CHA University, Seoul, Korea, Reliance Life Sciences, Mumbai, India, ReNeuron, Surrey, United Kingdom, StemCells, Inc., Palo Alto, Calif., Technion University, Haifa, Israel, University of California, San Francisco, Calif., and Wisconsin Alumni Research Foundation, Madison, Wis. In addition, examples of embryonic stem cells are described in the following U.S. patents and published patent applications: U.S. Pat. Nos. 6,245,566; 6,200,806; 6,090,622; 6,331,406; 6,090,622; 5,843,780; 20020045259; 20020068045. In preferred embodiments, the human ES cells are selected from the list of approved cell lines provided by the National Institutes of Health and accessible at http://escr.nih.gov. In certain preferred embodiments, an embryonic stem cell line is selected from the group comprising: the WA09 line obtained from Dr. J. Thomson (Univ. of Wisconsin) and the UC01 and UC06 lines, both on the current NIH registry.

In certain embodiments, a stem cell for use in disclosed methods is a stem cell of neural or neuroendocrine origin, such as a stem cell from the central nervous system (see, for example U.S. Pat. Nos. 6,468,794; 6,040,180; 5,753,506; 5,766,948), neural crest (see, for example, U.S. Pat. Nos. 5,589,376; 5,824,489), the olfactory bulb or peripheral neural tissues (see, for example, Published US Patent Applications 20030003574; 20020123143; 20020016002 and Gritti et al. 2002 J Neurosci 22(2):437-45), the spinal cord (see, for example, U.S. Pat. Nos. 6,361,996, 5,851,832) or a neuroendocrine lineage, such as the adrenal gland, pituitary gland or certain portions of the gut (see, for example, U.S. Pat. No. 6,171,610 and PC12 cells as described in Kimura et al. 1994 J. Biol. Chem. 269: 18961-67). In preferred embodiments, a neural stem cell is obtained from a peripheral tissue or an easily healed tissue, thereby providing an autologous population of cells for transplant.

Hematopoietic or mesenchymal stem cells may be employed in certain disclosed methods. Recent studies suggest that marrow-derived hematopoietic (HSCs) and mesenchymal stem cells (MSCs), which are readily isolated, have a broader differentiation potential than previously recognized. Purified HSCs not only give rise to all cells in blood, but can also develop into cells normally derived from endoderm, like hepatocytes (Krause et al., 2001, Cell 105: 369-77; Lagasse et al., 2000 Nat Med 6: 1229-34). Similarly, HSCs from peripheral blood and from umbilical cord blood are expected to provide a useful spectrum of developmental potential. MSCs appear to be similarly multipotent, producing progeny that can, for example, express neural cell markers (Pittenger et al., 1999 Science 284: 143-7; Zhao et al., 2002 Exp Neurol 174: 11-20). Examples of hematopoietic stem cells include those described in U.S. Pat. Nos. 4,714,680; 5,061,620; 5,437,994; 5,914,108; 5,925,567; 5,763,197; 5,750,397; 5,716,827; 5,643,741; 5,061,620. Examples of mesenchymal stem cells include those described in U.S. Pat. Nos. 5,486,359; 5,827,735; 5,942,225; 5,972,703, those described in PCT publication nos. WO 00/53795; WO 00/02654; WO 98/20907, and those described in Pittenger et al. and Zhao et al., supra.

Stem cell lines are preferably derived from mammals, such as rodents (e.g. mouse or rat), primates (e.g. monkeys, chimpanzees or humans), pigs, and ruminants (e.g. cows, sheep and goats), and particularly from humans. In certain embodiments, stem cells are derived from an autologous source or an HLA-type matched source. For example, stem cells may be obtained from a subject in need of pancreatic hormone-producing cells (e.g. diabetic patients in need of insulin-producing cells) and cultured to generate autologous insulin-producing cells. Other sources of stem cells are easily obtained from a subject, such as stem cells from muscle tissue, stem cells from skin (dermis or epidermis) and stem cells from fat.

In some preferred embodiments, cells for administration to a human should be compliant with good tissue practice guidelines set by the U.S. Food and Drug Administration (FDA) or equivalent regulatory agency in another country. Methods to develop such a cell line may include donor testing, and avoidance of exposure to non-human cells and products.

Cells derived from a donor (optionally the patient is the donor) may be administered as unfractionated or fractionated cells, as dictated by the purpose of the cells to be delivered. Cells may be fractionated to enrich for certain cell types prior to administration. Methods of fractionation are well known in the art, and generally involve both positive selection (i.e., retention of cells based on a particular property) and negative selection (i.e., elimination of cells based on a particular property). As will be apparent to one of skill in the art, the particular properties (e.g., surface markers) that are used for positive and negative selection will depend on the desired population of cells. Methods used for selection/enrichment of cells may include immunoaffinity technology or density centrifugation methods. Immunoaffinity technology may take a variety of forms, as is well known in the art, but generally utilizes an antibody or antibody derivative in combination with some type of segregation technology. The segregation technology generally results in physical segregation of cells bound by the antibody and cells not bound by the antibody, although in some instances the segregation technology which kills the cells bound by the antibody may be used for negative selection.

Any suitable immunoaffinity technology may be utilized for selection/enrichment of the selected cells to be used, including fluorescence-activated cell sorting (FACS), panning, immunomagnetic separation, immunoaffinity chromatography, antibody-mediated complement fixation, immunotoxin, density gradient segregation, and the like. After processing in the immunoaffinity process, the desired cells (the cells bound by the immunoaffinity reagent in the case of positive selection, and cells not bound by the immunoaffinity reagent in the case of negative selection) are collected and either subjected to further rounds of immunoaffinity selection/enrichment, or reserved for administration to the patient.

Immunoaffinity selection/enrichment is typically carried out by incubating a preparation of cells comprising the desired cell type with an antibody or antibody-derived affinity reagent (e.g., an antibody specific for a given surface marker), then utilizing the bound affinity reagent to select either for or against the cells to which the antibody is bound. The selection process generally involves a physical separation, such as can be accomplished by directing droplets containing single cells into different containers depending on the presence or absence of bound affinity reagent (FACS), by utilizing an antibody bound (directly or indirectly) to a solid phase substrate (panning, immunoaffinity chromatography), or by utilizing a magnetic field to collect the cells which are bound to magnetic particles via the affinity reagent (immunomagnetic separation). Alternately, undesirable cells may be eliminated from the preparation using an affinity reagent which directs a cytotoxic insult to the cells bound by the affinity reagent. The cytotoxic insult may be activated by the affinity reagent (e.g., complement fixation), or may be localized to the target cells by the affinity reagent (e.g., immunotoxin, such as ricin B chain).

Although it is expected that methods disclosed herein will be frequently used for in vivo monitoring of cells, it should be noted that the methodologies are equally effective for the monitoring of cells in culture, in a tissue sample or other ex vivo cellular material. For therapeutic uses, cells may be labeled at a desired step during the preparation for administration to the patient.

A variety of methods may be used to label cells with imaging reagent. In general, cells will be placed in contact with imaging reagent such that the imaging reagent becomes associated with the cell. Conditions will often be standard cell culture conditions designed to maintain cell viability. The term "associated" is intended to encompass any manner by which the imaging reagent and cell remain in sufficiently close physical proximity for a sufficient amount of time as to allow the imaging reagent to provide useful information about the position of the cell, whether in vivo or in vitro. Imaging reagent may be located intracellularly, e.g. after phagocytosis or surfactant mediated entry into the cell. Immune cells, such as dendritic cells, macrophages and T cells are often highly phagocytic and data presented herein and in other studies demonstrate that such cells, and other phagocytic cell types, are readily labeled. Other cell types, such as stem cells may also be labeled, regardless of phagocytic activity. Imaging reagent may be inserted into a cell membrane or covalently or non-covalently bound to an extracellular component of the cell. For example, certain linear fluorocarbons described herein may be derivatized to attach one or more targeting moiety. A targeting moiety will be selected to facilitate association of the imaging reagent with the cell to be labeled. A targeting moiety may be designed to cause non-specific insertion of the fluorocarbon into a cell membrane (e.g., a hydrophobic amino acid sequence or other hydrophobic moiety such as a palmitoyl moiety or myristoyl moiety) or to facilitate non-specific entry into the cell. A targeting moiety may bind to a cell surface component, as in the case of receptor ligands. A targeting moiety may be a member of a specific binding pair, where the partner is a cell surface component. The targeting moiety may be, for example, a ligand for a receptor, or an antibody, such as a monoclonal or polyclonal antibody or any of the various polypeptide binding agents comprising a variable portion of an immunoglobulin (e.g., Fv fragment, single chain Fv (scFv) fragment, Fab' fragment, F(ab')2 fragment, single domain antibody, camelized antibody, humanized antibody, diabodies, tribodies, tetrabodies).

Cellular labeling with fluorocarbons emulsions can also be facilitated using transfection agents to aid in cell delivery. Often transfection agents consist of cationic lipids, cationic liposomes, poly-cations, and the like. The transfection agent is pre-mixed with the fluorocarbon emulsion labeling agent, whereby it becomes associated with, or coats, the emulsion particles. The transfection agent-treated emulsion particles are then added to the cultured cells and incubated so that the cells become labeled. Common transfection agents include Lipofectamine (Invitrogen, Inc) FuGene, DOTAP (Roche Diagnostics, Inc.), and poly-L-lysine. Small proteins can also be used as transfection agents, such as many types of protamines. Protamines, the major DNA-binding proteins in the nucleus of sperm in most vertebrates, package the DNA in a volume less than 5% of a somatic cell nucleus. Protamines are simple proteins of low molecular weight that are rich in arginine and strongly basic. Commercially available protamines come from the sperm of salmon and certain other species of fish. The term "protamine" as used herein, refers to a low molecular weight cationic, arginine-rich polypeptide. The protamine molecule typically comprises about 20 to about 200 amino acids and is generally characterized by containing at least 20%, 50% or 70% arginine. Protamines are often formulated as salts, with one or more counter ions such as sulfate, phosphate and chloride.

Data provided in this application show that protamines (e.g., protamine sulfate) are highly effective in delivering PFPE fluorocarbon emulsion particles to cultured cells. Suitable protamine sulfates can come from a variety of sources (e.g., salmon, herring, trout, etc.) and be of various grades and forms (e.g., USP, grades II, III, X, etc.), with and without histones or any recombinant derivative. Examples of other protamine solutions that may be used as transfection agents include protamine phosphate, protamine chloride, protamine sulfate-2, protamine sulfate-3, protamine sulfate-10, and protamine free base.

Cell electroporation can also be used to deliver fluorocarbon emulsion particles into cells. Electroporation has the advantage that labeling is very rapid proccess, and it does not require the use of transfection agents. Many methods of cell electroporation are know in the art for a wide range of cell types, and several commercially available electropration instruments are available (e.g., BTX, Inc., Harvard Apparatus, Inc., Amaxa Biosystems, Inc., etc.). Electroporation is used to deliver nucleic acids, molecules, and small particulates into cells in vitro. Magnetoelectorporation has been shown to be effective for MRI in cell culture (Walczak P., Magn Reson Med. 2005. October; 54(4):769-74). Data in this application shows that cell electroporation is effective in delivering linear PFPE fluorocarbon emulsion particles into dendritic cells, and there is no barrier to using the same method to fluorocarbon-label many other phagocytic and non-phagocytic cell types, such as stem cells.

Where cells are to be used in a therapeutic regimen, various methods have been used to for delivery of cells including injections and use of special devices to implant cells in various organs. The present invention is not tied to any particular delivery method. Data presented herein demonstrate that labeled cells may be monitored regardless of whether the cells are delivered directly to a particular site or delivered systemically. For example, labeled DCs were successfully imaged following either a focal implantation directly into tissues or an intravenous injection, and T-cells were imaged following intraperitoneal injection. Cells may be inserted into a delivery device which facilitates introduction by injection or implantation into the subjects. Such delivery devices may include tubes, e.g., catheters, for injecting cells and fluids into the body of a recipient subject. In a preferred embodiment, the tubes additionally have a needle, e.g., a syringe, through which the cells of the disclosure can be introduced into the subject at a desired location. The cells may be prepared for delivery in a variety of different forms. For example, the cells may be suspended in a solution or gel or embedded in a support matrix when contained in such a delivery device. Cells may be mixed with a pharmaceutically acceptable carrier or diluent in which the cells of the disclosure remain viable. Pharmaceutically acceptable carriers and diluents include saline, aqueous buffer solutions, solvents and/or dispersion media. The use of such carriers and diluents is well known in the art. The solution is preferably sterile and fluid. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like. Solutions of the disclosure may be prepared by incorporating cells as described herein in a pharmaceutically acceptable carrier or diluent and, as required, other ingredients enumerated above, followed by filtered sterilization.

4. Nuclear Magnetic Resonance Techniques

As described herein, nuclear magnetic resonance techniques may be used to detect populations of labeled cells. The term "detect" is used to include any effort to ascertain the presence or absence of a labeled molecule or cell, particularly by a nuclear magnetic resonance technique. The term "detect" is also intended to include more sophisticated measurements, including quantitative measurements and two- or three-dimensional image generation. For example, MRI may be used to generate images of such cells. In many instances, the labeled cells may be administered to a living subject. Following administration of the cells, some portion of the subject, or the entire subject, may be examined by MRI to generate an MRI data set. A "data set", as the term is used herein, is intended to include raw data gathered during magnetic resonance probing of the subject material, the acquisition parameters, as well as information processed, transformed or extracted from the raw data. The raw data includes transient signals obtained by MRI/MRS, including the free-induction decays, spin-echoes, stimulated-echoes, and/or gradient echoes. Examples of processed information include two-dimensional or three-dimensional pictorial representations of the subject material. The processed information may also include magnitude images, the real and imaginary image components, as well as the associated phase map images. Another example of extracted information is a score representing the amount or concentration of imaging reagent or $^{19}F$ signal in the subject material. By using the amount of $^{19}F$ signal in the subject material, and a calibration of the mean amount of imaging reagent per cell pre-implantation, one can estimate the absolute number of cells in the subject material. The amount of $^{19}F$ signal present in a subject material can be represented or calculated in many ways; for example, the average signal-to-noise-ratio (SNR) of the $^{19}F$ signal for a region of interest (ROI) may be measured and used to calculate the abundance of labeled cells. In certain embodiments, the average intensity, or pixel- or voxel-wise summation of the $^{19}F$ signal may be used to calculate the abundance of labeled cells. This type of data may be gathered at a single region of the subject, such as, for example, the spleen or another organ of particular relevance to the labeled cells. Labeled cells may be examined in contexts other than in the subject. It may be desirable to examine labeled cells in culture. In certain embodiments, labeled cells may be applied to or generated within a tissue sample or tissue culture, and labeled cells may therefore be imaged in those contexts as well. For example, an organ, tissue or other cellular material to be transplanted may be contacted with an imaging reagent to generate labeled cells prior to implantation of such transplant in a subject.

In general, labeling agents of the disclosure are designed for use in conventional MRI detection systems. In the most common implementation of MRI, one observes the hydrogen nucleus (proton, $^1H$) in molecules of mobile water contained in subject materials. To detect labels disclosed herein, an alternate nucleus is detected, $^{19}F$. $^{19}F$ MRI has only slightly less intrinsic sensitivity compared to $^1H$; the relative sensitivity is approximately 0.83. Both have a nuclear spin of $+\frac{1}{2}$. The natural isotopic abundance of $^{19}F$ is 100%, which is comparable to 99.985% for $^1H$. The physical principles behind the detection and image formation are the same for both $^1H$ and $^{19}F$ MRI. The subject material is placed in a large static magnetic field. The field tends to align the magnetic moment associated with the $^1H$ or $^{19}F$ nuclei along the field direction. The nuclei are perturbed from equilibrium by pulsed radio-frequency (RF) radiation at the Larmor frequency, which is a characteristic frequency proportional to the magnetic field strength where nuclei resonantly absorb energy. Upon removing the RF, the nuclei induce a transient voltage in a receiver antenna; this transient voltage constitutes the nuclear magnetic resonance (NMR) signal. Spatial information is encoded in both the frequency and/or phase of the NMR signal by selective application of magnetic field gradients that are superimposed onto the large static field. The transient voltages are generally digitized, and then these signals may be processed by, for example, using a computer to yield images.

At constant magnetic field strength, the Larmor frequency of $^{19}F$ is only slightly lower (~6%) compared to $^1H$. Thus, it is straightforward to adapt conventional MRI scanners, both hardware and software, to acquire $^{19}F$ data. The $^{19}F$ detection may be coupled with different types of magnetic resonance scans, such as MRI, MRS or other techniques. Typically, it will be desirable to obtain a $^1H$ MRI image to compare against the $^{19}F$ image. In a living organism or other biological tissue, the proton MRI will provide an image of the subject material and allow one to define the anatomical context of the labeled cells detected in the 19F image. In a preferred embodiment of the disclosure, data is collected for both $^{19}F$ and $^1H$ during the same session; the subject is not moved during these acquisitions to better ensure that the two data sets are in spatial registration. Normally, $^{19}F$ and $^1H$ data sets are acquired sequentially, in either order. An RF coil (i.e. antenna) can be constructed that can be electrically tuned from the $^{19}F$ and $^1H$ Larmor frequency. Tuning between these two frequencies can be performed manually (e.g. via an electro-mechanical variable capacitor or inductor), or electrically, via active electronic circuitry. Alternatively, with appropriate modifications to the hardware and/or software of the MRI instrument, both data sets can be acquired simultaneously, for example, to conserve imaging time. Simultaneous acquisition of the $^{19}$F and $^1$H data sets require an RF coil or antenna that can be electrically tuned simultaneously to the $^{19}$F and $^1$H Larmor frequency (i.e., a double-tuned coil). Alternatively the RF coil can be "broadband," with one broadly-tuned electrical resonance that covers both Larmor frequencies (i.e. $^{19}$F and $^1$H). Other imaging techniques, such as fluorescence detection may be coupled with $^{19}$F MRI. This will be particularly desirable where a fluorocarbon imaging reagent has been derivatized with a fluorescent moiety. In other embodiments, the $^{19}$F MRI scan may be combined with a PET scan in the same subject or patient by using dual-model radioactve $^{18}$F/$^{19}$F fluorocarbon labeling reagents as described herein.

MRI examination may be conducted according to any suitable methodology known in the art. Many different types of MRI pulse sequences, or the set of instructions used by the MRI apparatus to orchestrate data collection, and signal processing techniques (e.g. Fourier transform and projection reconstruction) have been developed over the years for collecting and processing image data (for example, see *Magnetic Resonance Imaging, Third Edition*, editors D. D. Stark and W. G. Bradley, Mosby, Inc., St. Louis Mo. 1999). The reagents and methods of this disclosure are not tied to any particular imaging pulse sequence or processing method of the raw NMR signals. For example, MRI methods that can be applied to this disclosure broadly encompasses spin-echo, stimulated-echo gradient-echo, free-induction decay based imaging, and any combination thereof. Fast imaging techniques, where more than one line in k-space or large segments of k-space are acquired from each excited signal, are also highly suitable to acquire the $^{19}$F (or $^1$H) data. Examples of fast imaging techniques include fast spin-echo approaches (e.g. FSE, turbo SE, TSE, RARE, or HASTE), echo-planar imaging (EPI), combined gradient-echo and spin-echo techniques (e.g. GRASE), spiral imaging, and burst imaging. Furthermore, rapid acquisition schemes using reduced k-space sampling known in the art are highly appropriate for $^{19}$F imaging (e.g., key-hole imaging, single value decomposition encoding, reduced imaging using generalized series reconstruction, RIGR, and the like). Ideally, in these sampling schemes only the central parts of k-space are acquired where most of the $^{19}$F signal is present. Although some edge resolution loss may occur, often only a low resolution $^{19}$F image is needed, and the $^1$H image overlay provides the fine anatomical detail. The development of new and improved pulse sequence and signal processing methods is a continuously evolving field, and persons skilled in the art can devise multiple ways to image the $^{19}$F labeled cells in their anatomical context.

As another example of a nuclear magnetic resonance technique, MRS can be used to detect the presence of fluorocarbon-labeled cells in localized tissues or organs. Normally MRS methods are implemented on a conventional MRI scanner. Often the localized volume of interest (VOI) is defined within a conventional anatomical $^1$H MRI scan. Subsequently, the magnitude of the $^{19}$F NMR signal observed within the VOI is directly related to the number of labeled cells, and/or the mean concentration of PFPE per cell present in the tissue or organ. Methods for isolating a VOI within a much larger subject are well known the art (for example, *Magnetic Resonance Imaging, Third Edition*, Chapter 9, Editors D. D. Stark and W. G. Bradley, Mosby, Inc., St. Louis Mo. 1999). Examples include using a localized RF surface coil near the VOI, surface spoiling, surface coil BI-gradient methods, slice-selective $B_0$-gradient techniques, STEAM, PRESS, image selective in vivo spectroscopy (ISIS), and magnetic resonance spectroscopic imaging (MRSI). The development of new and improved pulse sequence and signal processing methods is continuously evolving for MRS, and persons skilled in the art can devise multiple ways to detect the $^{19}$F NMR signals emanating from the fluorocarbon labeled cells in VOIs.

In certain embodiments the disclosure provides a method of quantifying the numbers of labeled cells in vivo or in subject materials within an ROI. An ROI may include all labeled cells in a subject or labeled cells in specific organs such as the pancreas, specific tissues such as lymph nodes, or any region or of one or more voxels showing detectable MRI/MRS $^{19}$F signal. A ROI can be an otherwise undefined area beyond a particular experiment. There are a number of ways that labeled cells may be quantified in the subject materials or in vivo, as described herein.

Calibrating the mean "cellular dose" of $^{19}$F labeling agent pre-implantation of a particular cell population is often a pre-requisite for quantitative cell determinations in subject materials or the patient. It is anticipated that different cell types have different innate abilities to take up the labeling agents in vitro, and thus the cellular dose of the labeling agent will also vary. Furthermore, different cells of the same type acquired from different sources (e.g., different patients) may have different affinities for the labeling agent. Thus a cellular dose calibration may be required. This calibration may be used, initially, to modify the labeling protocol (i.e., incubation conditions, duration of time that cells are incubated with labeling fluorocarbon emulsion, concentration of fluorocarbon emulsion in culture medium during labeling, etc.) to achieve a certain range of cellular dose before labeled cells are actually used in a subject to be imaged. Alternatively, one can fix the labeling conditions and protocol and measure the mean value $^{19}$F labeled per cell, as is, for subsequent quantification in the subject to be imaged. In certain embodiments the mean number of $^{19}$F molecules (F's) per cell of a labeled cell population is measured (i.e., calibrated) in vitro prior to administration of the cells to the subject or patient. In certain embodiments the mean number of $^{19}$F molecules (F's) per cell of a labeled cell population is calibrated in a test population of cells of a particular type, not necessarily destined for a patient, but used to calibrate cellular dose of labeling agent as a consequence of a particular labeling protocol or set of conditions; optionally, the value of cellular dose is then used for future labeling and in vivo imaging experiments in the same population type of cells with the same labeling protocol.

The cellular dose of labeling agent can be assayed in vitro using a variety of quantitative techniques. For example, one can use a one-dimensional (1D) $^{19}$F NMR spectrum obtained from a cell pellet, cell suspension, or cell lysate, of a known number of labeled cells. From this spectrum, one can calculate the integrated area of the $^{19}$F spectrum or a portion thereof, originating from the labeling reagent associated with the cells. The integrated area of the $^{19}$F spectrum, denoted $S_{cells}$, is directly proportional to the total amount of $^{19}$F in the cell pellet, suspension, or lysate. To measure the absolute number of $^{19}$F nuclei, the measured $S_{cells}$ may be normalized to a $^{19}$F standard. A $^{19}$F standard can be, for example, a solution of a known volume and concentration of a fluorochemical, where one can calculate the total number of $^{19}$F nuclei in the standard, denoted $F_{stan}$. A suitable fluoro-chemical reference ideally has a simple $^{19}$F NMR spectrum, preferable with a single narrow resonance (e.g. trifluoroacetic acid or trifluoroethanol) and optionally a $^{19}$F chemical shift that is significantly different than the labeling fluorocarbon. The $^{19}$F standard can be placed in the same NMR tube as the labeled cell material being measured, in a separate tube, or optionally can be measured in a separate experiment using the same NMR instrument. The integrated area of the spectrum from the $^{19}$F standard, denoted $S_{stan}$, can then be measured. Subsequently, the mean number of $^{19}$F per labeled cell, denoted $F_c$, can be calculated, for example using the formula:

$$F_c = \frac{S_{cells}}{S_{stan}} F_{stan} \frac{1}{N_{cells}}$$

where $N_{cells}$ is the number of labeled cells contained in the in vitro test sample. An example of this calibration procedure is described herein in the Examples. Quantitative NMR methods for $^{19}$F and other nuclei are well know in the art, and those skilled can devise many variations to the cellular dose calibration procedure described above. Besides $^{19}$F NMR, there are other quantitative methods that can be used to assay the cellular dose of the labeling reagent. For example, a reagent may be labeled fluorescently, luminescently, optically, or radioactively.

In order to extract accurate quantification of labeled cells from the $^{19}$F MRI/MRS data sets, additional calibrations and standards may be employed. For example, one can use a calibrated external $^{19}$F reference (i.e. phantom) during the actual $^{19}$F MRI/MRS scan of the subject material containing labeled cells. The image intensity of the calibrated phantom is used when analyzing the $^{19}$F MRI/MRS data set to proved an absolute standard for the number of $^{19}$F nuclei when examining the subject material or patient. The calibrated phantom is used to normalize the sensitivity of the particular MRI/MRS system that has been loaded with a particular subject to be imaged. The $^{19}$F reference may be, for example, one or more vessels containing a solution of a known concentration of $^{19}$F nuclei. In preferred embodiments, the solution contains a dilute concentration of the emulsified fluorocarbon labeling reagent. Optionally, the solution contains non-emulsified fluorocarbon labeling reagent, a gel, or liquid, for example that has been diluted in a suitable solvent. Optionally, the solution can be comprised of another fluoro-chemical, ideally with a simple $^{19}$F NMR spectrum, preferable with a single narrow NMR resonance (e.g. trifluoroacetic acid (TFA) or trifluoroacetamide (TFM) and other fluorinated acids). In preferred embodiments, the T1 and T2 values of the reference solution are similar to those of the labeling reagent. Optionally, the solution can contain perfluorocarbon-labeled cells, or lysates of the same. The non-cellular reference has the advantage of longer storage times. Optionally, the solution can take the form of a gel. The vessel containing the solution is preferably sealable, and can take a variety of geometries; preferred vessel geometries include ellipsoidal, cylindrical, spherical, and parallel piped shapes. One or more vessels containing $^{19}$F reference solution can be used during the $^{19}$F MRI/MRS of the subject material. If multiple $^{19}$F references (i.e. vessels) are used they can contain the same $^{19}$F concentration or different concentrations, and in the case of the latter, they ideally contain graded concentrations of fluoro-chemical. The placement of the calibrated $^{19}$F reference vessel(s) can be placed preferably externally or alongside, or optionally inside, the imaged subject or patient prior to data acquisition. In preferred embodiments, the reference is imaged using $^{19}$F MRI along with the subject in the same image field of view (FOV). Optionally, $^{19}$F MRS data is acquired in the reference either sequentially or in parallel with the subject data set. Optionally, data from the reference can be acquired using MRI/MRS acquired in a separate scan. Optionally, the external reference is not scanned along with a subject in every $^{19}$F MRI/MRS examination, but rather, values of the reference $^{19}$F signal intensity acquired using MRI/MRS is used from a scan of a comparable subject or a simulated-subject. In a given $^{19}$F MRI/MRS scan, the calibrated $^{19}$F standard may be sampled by one or more voxels. The observable $^{19}$F intensity produced by a voxel may be proportional to the concentration of the fluorochemical in the solution (or gel) and the voxel volume. Often in a $^{19}$F MRI scan the reference standard is comprised of many voxels. Often one calculates the mean intensity of one, several, or all voxels in the reference standard. Optionally, the mean image intensity is calculated over an ROI defined within the $^{19}$F image of the reference standard. Optionally, the physical geometry of the reference standard vessel contributes to defining the observed $^{19}$F signal intensity; for example, the volume compartment(s) containing the $^{19}$F reference solution is smaller than the voxel volume. In other embodiments, the calibrated external reference relies on a solution with a $^1$H signal intensity of a known number of detectable $^1$H; in this case the sensitivity of the $^{19}$F signal in the subject material is reference to a $^1$H calibrated standard. Ideally the solution or gel in the $^1$H calibrated reference (contained in a vessel as described above) yields a simple $^1$H NMR spectrum, preferable with a single narrow NMR resonance (e.g., H$_2$O, or mixtures of H$_2$O-D$_2$O). Other than a different nuclei, the use of the $^1$H standard reference is the same in many other respects as described above for the $^{19}$F reference. In some embodiments, the $^1$H reference is an internal organ or region of tissue and the data may be raw or normalized. Optionally, the calibrated reference standard contains any other MRI/MRS-active nuclei. In other embodiments, the reference is a standard that is not scanned with the subject, but is calibrated by relevant factors such as the weight of the patient or the size of the body cavity.

By computationally manipulating or combining a key set of parameters from the $^{19}$F MRI/MRS data set, one can calculate the number of labeled cells present in an ROI as described herein. For example, a key set of parameters may include: (i) the cellular dose of labeling agent (i.e., $F_c$) measured in vitro; (ii) in vivo $^{19}$F MRI/MRS data set taken in the subject at one or more time points following labeled cell administration; (iii) the voxel volume; (iv) the in-plane voxel area (i.e., area of the image pixel); (v) optionally, the MRI/MRS data set from the $^{19}$F reference standard; (vi) optionally, the measured Johnson noise of the $^{19}$F MRI/MRS data in the subject material; (vii) optionally, the measured signal-to-noise ratio (SNR) of one or more voxels of the $^{19}$F MRI/MRS data set in the subject material; (viii) optionally, the measured SNR of one or more voxels of the $^{19}$F MRI/MRS data set from the reference standard; (ix) optionally, the $^{19}$F NMR relaxation times (T1, T2, and T2*) of the subject material; (x) optionally, the $^{19}$F NMR relaxation times (T1, T2, and T2*) of the reference standard (for example, see *Magnetic Resonance Imaging, Third Edition*, chapter 4, editors D. D. Stark and W. G. Bradley, Mosby, Inc., St. Louis Mo. 1999). Those skilled in the art can derive other parameters, combinations of the above set, or derivations thereof, particularly from the $^{19}$F MRI/MRS dataset, that can be used to quantify the number of labeled cells in situ. In certain embodiments the above set of key parameters can be used to derive quantitative or statistical measures of the accuracy or confidence of the measured number of labeled cells.

There are many ways to combine the key parameters (i-x, above), any subsets of these, or any of their combinations or approximations, to estimate the effective number of labeled cells seen by $^{19}$F MRI in the subject material, denoted by $N_c$. For example, one can use an equation of the form $$N_c = \frac{[F_R]v}{I_R} \frac{1}{F_c} \sum_{i=1}^{N_{ROI}} I_c^{(i)}$$

where: $N_c$=total number of labeled cells in the ROI; $[F_R]$=concentration of $^{19}$F in the calibrated $^{19}$F reference solution (or gel); v=voxel volume; $I_R$=mean intensity of the calibrated $^{19}$F reference taken with the MRI/MRS scan, averaged over one or more voxels; $F_c$=average $^{19}$F cellular dose of the labeling agent measured in vitro; $N_{ROI}$=number of voxels in the ROI containing labeled cells; $I_c^{(i)}$=image intensity of the $i^{th}$ voxel in the ROI containing labeled cells; i=unitless index for voxels in the ROI containing labeled cells.

There are also many ways to approximate $N_c$ from the $^{19}$F data set. For example, one could use the expression $$N_c \approx \frac{I_c^{avg}}{I_R}[F_R]v\frac{1}{F_c}N_{ROI}$$

where $I_c^{avg}$ is the average intensity of the ROI containing the labeled cells, (i.e. the average intensity of the $N_{ROI}$ voxels). As another example, one could use $$N_c \approx \frac{I_c^{avg}}{I_R}V_c\frac{1}{F_c}[F_R]$$

where $V_c$ is the total volume of the ROI containing the labeled cells. As a further example, one could use $$N_c \approx \frac{I_c^{avg}}{I_R}\frac{V_c}{V_R}\frac{1}{F_c}N_R$$

where $V_R$ is the effective volume of the reference in the $^{19}$F MRI/MRS and NR is the number $^{19}$F nuclei in $V_R$. Note that in all of the above formulas the various intensities (i.e., $I_R$, $I_c^{avg}$, $I_c^{(i)}$) can be normalized to the image noise, and thus the above formulas can be equivalently expressed in terms of the appropriate SNR values for the particular regions. Thus, there are many ways to estimate the number of labeled cells, $N_c$, and many similar forms of these basic expressions can be derived by basic mathematical manipulations, however, all rely on the same basic content contained within the input parameters described by (i-x). Furthermore, quantification of labeled cells in an ROI need not be expressed in terms of absolute numbers or effective cell numbers. Other quantitative indices can be derived that are indicative of the amount of cells in an ROI. For example, one can calculate the ratio $I_c^{avg}/I_R$, or the ratio of the average SNR values observed in the ROI and the reference; all of these fall within subsets of the above expressions and/or the parameters. In certain embodiments, the quantity of apparent PFPE-labeled cells is calculated directly from the in vivo MRI data set, the external $^{19}$F reference, and the measured $F_c$, where the calculation is performed on a per-slice basis.

It is noted that the above analysis of cell numbers and related indices assume that the $^{19}$F NMR relaxation times (i.e., particularly T1 and/or T2) of the fluorocarbon label is approximately the same as material in the calibrated $^{19}$F reference standard. In the case that the relaxation times are not comparable, one of skill in the art can readily correct for this by employing the known MRI intensity equations of the particular imaging protocol being used, expressed in terms of T1 and T2.

Optionally, the $^{19}$F MRI data set of the subject material can undergo post-processing before the actual cell quantification calculation is performed (as described above). For example, post-processing algorithms may include "de-noising" the $^{19}$F data set. This can be accomplished by, for example, by thresholding the image to cut off low-intensity noise; this involves rescaling the image intensity so that low values are set to zero. In magnitude MRI images, random Johnson noise is often apparent and uniformly distributed across the image FOV. It is well know in the art that one can threshold out the low-level image intensity so that regions known to contain no true signal (i.e. devoid of $^{19}$F and/or $^1$H nuclei) appear to have a null or very near-null intensity. This process can be performed in an ad-hoc fashion (i.e. "manually" or by visual inspection), or by using a computer algorithm. In other embodiments, de-noising of the data set can be achieved by using other algorithms, for example using wavelet analysis or Rician corrections (21), and many methods are known in the art for image de-noising. The following references are incorporated in their entirety herein: Khare, A., et al., INTERNATIONAL JOURNAL OF WAVELETS MULTIRESOLUTION AND INFORMATION PROCESSING, 3 (4): 477-496 DECEMBER 2005; Cruz-Enriquez, H., et al., IMAGE ANALYSIS AND RECOGNITION, 3656: 247-254 2005; Awate, S P., et al., INFORMATION PROCESSING IN MEDICAL IMAGING, PROCEEDINGS, 3565: 677-688 2005; Ganesan, R., et al., IIE TRANSACTIONS, 36 (9): 787-806 SEPTEMBER 2004; Scheunders, P., IEEE TRANSACTIONS ON IMAGE PROCESSING, 13 (4): 475-483 APRIL 2004; Ghugre, N R., MAGNETIC RESONANCE IMAGING, 21 (8): 913-921 OCTOBER 2003; Bao, P., et al., IEEE TRANSACTIONS ON MEDICAL IMAGING, 22 (9): 1089-1099 SEP 2003; Wu, Z Q., et al., ELECTRONICS LETTERS, 39 (7): 603-605 APR. 3, 2003; LaConte, S M., et al., MAGNETIC RESONANCE IN MEDICINE, 44 (5): 746-757 NOVEMBER 2000; Laine, A F., ANNUAL REVIEW OF BIOMEDICAL ENGINEERING, 2: 511-550 2000; Zaroubi, S., et al., MAGNETIC RESONANCE IMAGING, 18 (1): 59-68 JANUARY 2000; Nowak, R D., IEEE TRANSACTIONS ON IMAGE PROCESSING, 8 (10): 1408-1419 OCTOBER 1999; and Healy, D M., et al., ANNALS OF BIOMEDICAL ENGINEERING, 23 (5): 637-665 SEPTEMBER-OCTOBER 1995.

Other types of post-processing algorithms are know in the art that can be applied to the $^{19}$F MRI data set before or after quantification, such as zero-filling (A Handbook of Nuclear Magnetic Resonance, $2^{nd}$ Edition, Ray Freeman, Addison Wesley Longman Press 1997) and various image interpolation, de-noising, and image smoothing algorithms (for example, see The Image Processing Handbook, $3^{rd}$ Edition, John C. Russ, CRC Press/IEEE Press).

In certain embodiments the above set of key parameters (i-x) can be used to derive quantitative or statistical measures of the accuracy or confidence of the measured number of labeled cells or related indices. $^{19}$F MRI/MRS data sets are often subject to SNR limitations within ROI, and thus it is often useful to calculate a metric of the confidence or accuracy of the measurement. Many methods are known in the art for the statistical analysis of MRI and other biomedical-type images. The claimed embodiment is understood to encompass these known methods.

5. Computer Methods

Figure 16:
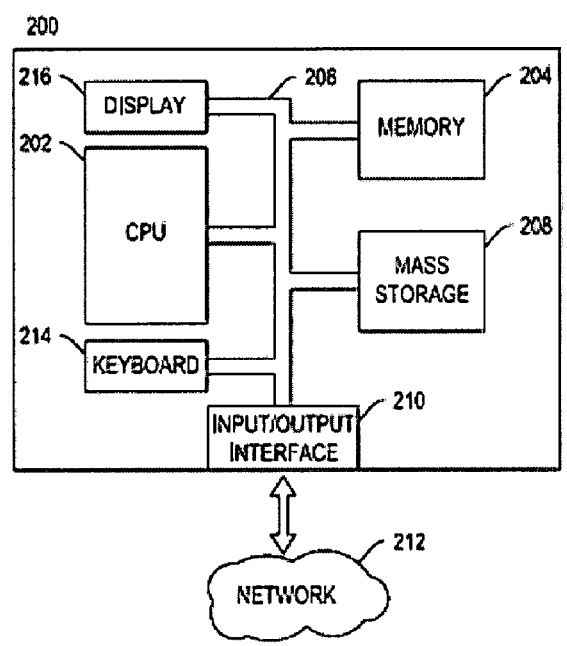
FIG. 16. A functional block diagram of a general purpose computer system 200 for performing the functions of the computer 104 according to an illustrative embodiment of the invention.

Methods for quantifying labeled cells will typically be conducted with the aid of a computer, which may operate software designed for the purpose of such quantification. Such software may be a stand-alone program or it may be incorporated into other software, such as MRI image processing software. FIG. 16 shows a functional block diagram of general purpose computer system 200 for performing the functions of the computer according to an illustrative embodiment of the disclosure. The exemplary computer system 200 includes a central processing unit (CPU) 202, a memory 204, and an interconnect bus 206. The CPU 202 may include a single microprocessor or a plurality of microprocessors for configuring computer system 200 as a multi-processor system. The memory 204 illustratively includes a main memory and a read only memory. The computer 200 also includes the mass storage device 208 having, for example, various disk drives, tape drives, etc. The main memory 204 also includes dynamic random access memory (DRAM) and high-speed cache memory. In operation, the main memory 204 stores at least portions of instructions and data for execution by the CPU 202.

The mass storage 208 may include one or more magnetic disk or tape drives or optical disk drives, for storing data and instructions for use by the CPU 202. At least one component of the mass storage system 208, preferably in the form of a disk drive or tape drive, stores the database used for processing the cell quantification of the disclosure. The mass storage system 208 may also include one or more drives for various portable media, such as a floppy disk, a compact disc read only memory (CD-ROM), or an integrated circuit non-volatile memory adapter (i.e. PC-MCIA adapter) to input and output data and code to and from the computer system 200.

The computer system 200 may also include one or more input/output interfaces for communications, shown by way of example, as interface 210 for data communications via the network 212. The data interface 210 may be a modem, an Ethernet card or any other suitable data communications device. To provide the functions of a computer, the data interface 210 may provide a relatively high-speed link to a network 212, such as an intranet, internet, or the Internet, either directly or through another external interface. The communication link to the network 212 may be, for example, optical, wired, or wireless (e.g., via satellite or cellular network). Alternatively, the computer system 200 may include a mainframe or other type of host computer system capable of Web-based communications via the network 212.

The computer system 200 also includes suitable input/output ports or uses the interconnect bus 206 for interconnection with a local display 216 and keyboard 214 or the like serving as a local user interface for programming and/or data retrieval purposes. Alternatively, server operations personnel may interact with the system 200 for controlling and/or programming the system from remote terminal devices via the network 212.

The computer system 200 may run a variety of application programs and stores associated data in a database of mass storage system 208. One or more such applications may enable the receipt and delivery of messages to enable operation as a server, for implementing server functions relating to quantification.

The components contained in the computer system 200 are those typically found in general purpose computer systems used as servers, workstations, personal computers, network terminals, and the like. In fact, these components are intended to represent a broad category of such computer components that are well known in the art. Certain aspects of the disclosure may relate to the software elements, such as the executable code and database for the server functions of the quantification system.

The disclosure will be more readily understood by reference to the following examples, which are included merely for purposes of illustration of certain aspects and embodiments of the present application, and are not intended to limit the disclosure.

EXAMPLES

Figure 2:
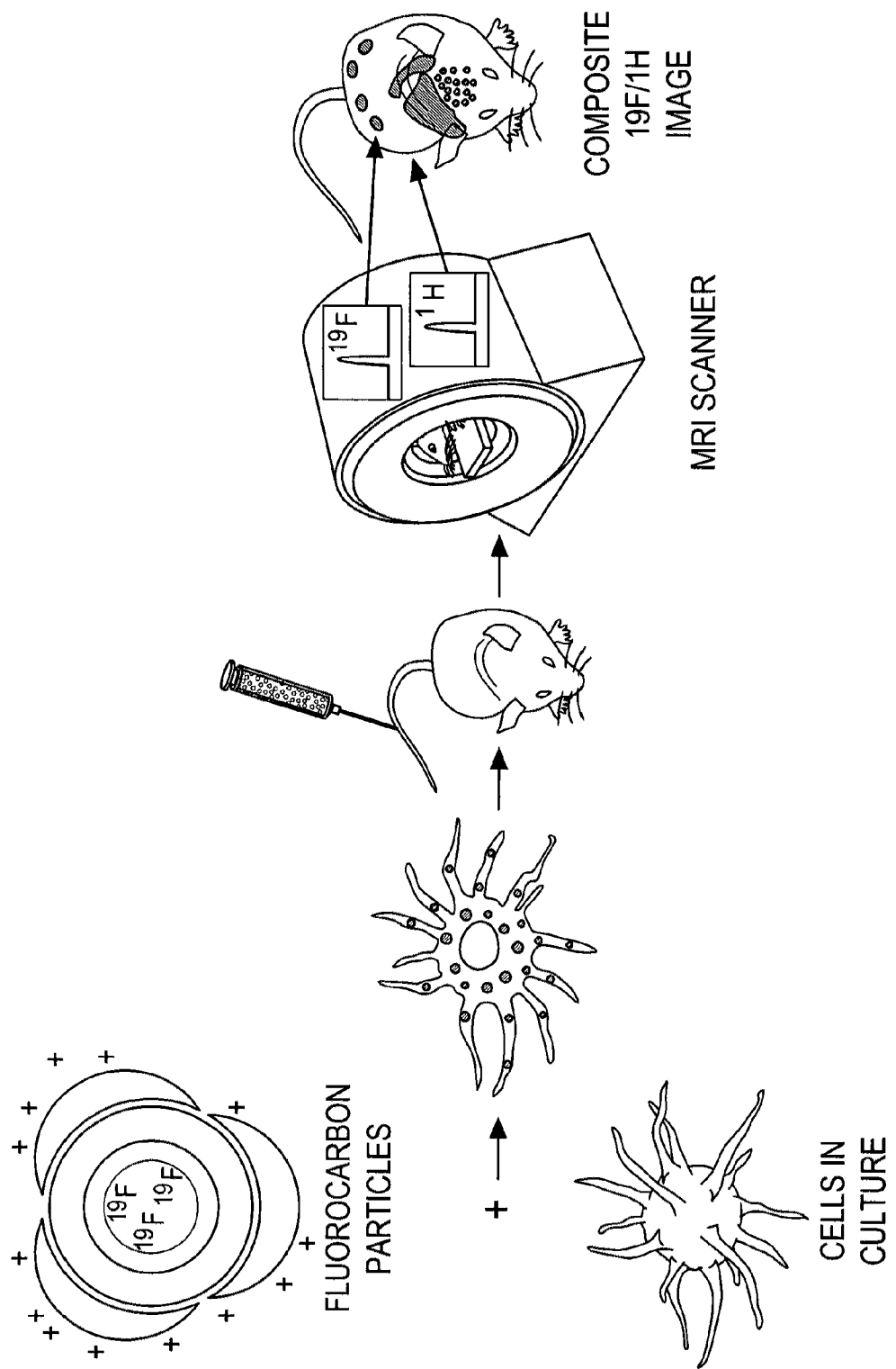
FIG. 2. Illustration of cells being labeled ex vivo, transferred into a host, and imaged using $^{19}F$ and $^{1}H$, and visualized via a composite $^{19}F/^{1}H$ image.
Figure 9C:
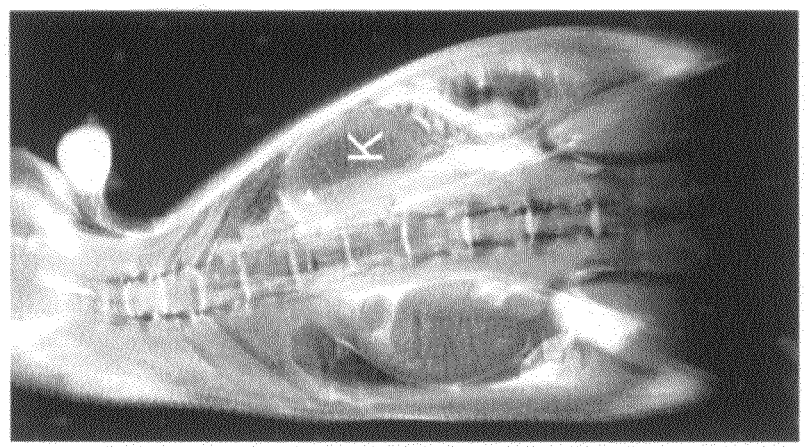
FIGS. 9A-9D. In vivo MRI showing transferred T cells homing to the pancreas. Panels (a)-(c) are composite $^{19}F/^{1}H$ images through the mouse torso, where the $^{19}F$ is rendered in pseudo-color and the $^{1}H$ is in grayscale. Only slices containing $^{19}F$ signal are shown. (a) Image of PFPE labeled, in vitro activated diabetogenic T cells ($5\times10^6$) transferred i.p. into an NOD SCID mouse 48 hours prior. The image shows specific T cells (pseudo-color) homing to the pancreas (P). The $^{19}F$ reference capillary (R) is placed next to the mouse. The lungs, spleen (S) and liver (L) are labeled. Panel (b) shows a negative control image of an NOD SCID mouse that received cell-free PFPE nanoparticles in PBS at an equivalent $^{19}F$ dose of $1\times10^7$ labeled T cells. We detected the PFPE (pseudo-color) only near the gut (G). Panel (c) shows a negative control image of a NOD SCID mouse that received activated, labeled MHC-mismatched T cells. We did not detect a signal in or around the pancreas, liver or spleen, but cells (pseudo-color) can be seen at a site near the kidney (K). Panel (d) shows results of the in vivo quantification of the apparent T cells homing to the pancreas for the cohort of NOD SCID mice. The values represent the percentage of cells detected in the pancreas compared to the total number of i.p. transferred cells, ranging from $2\text{-}6\times10^6$ cells. See Methods for explanation of error bars.
Figure 9B:
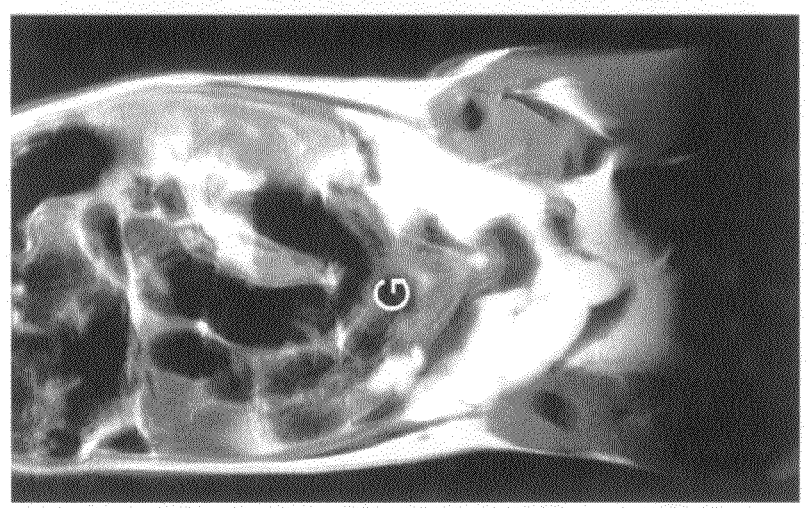
Figure 9A:
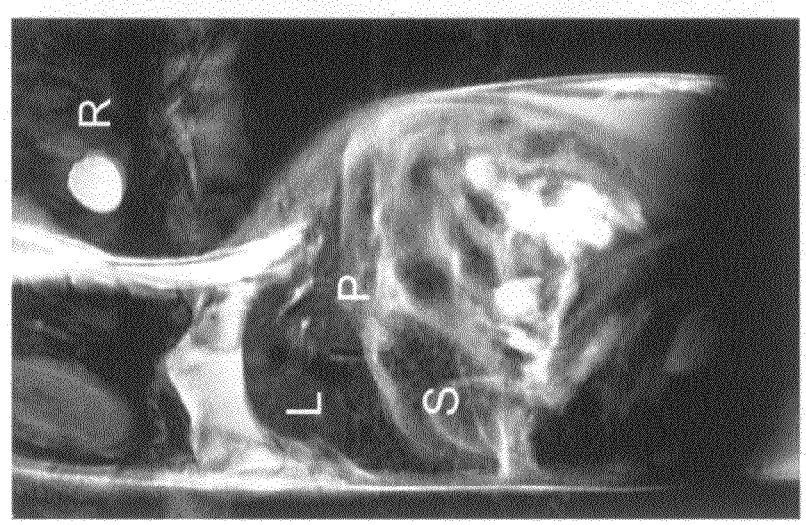
Figure 13:
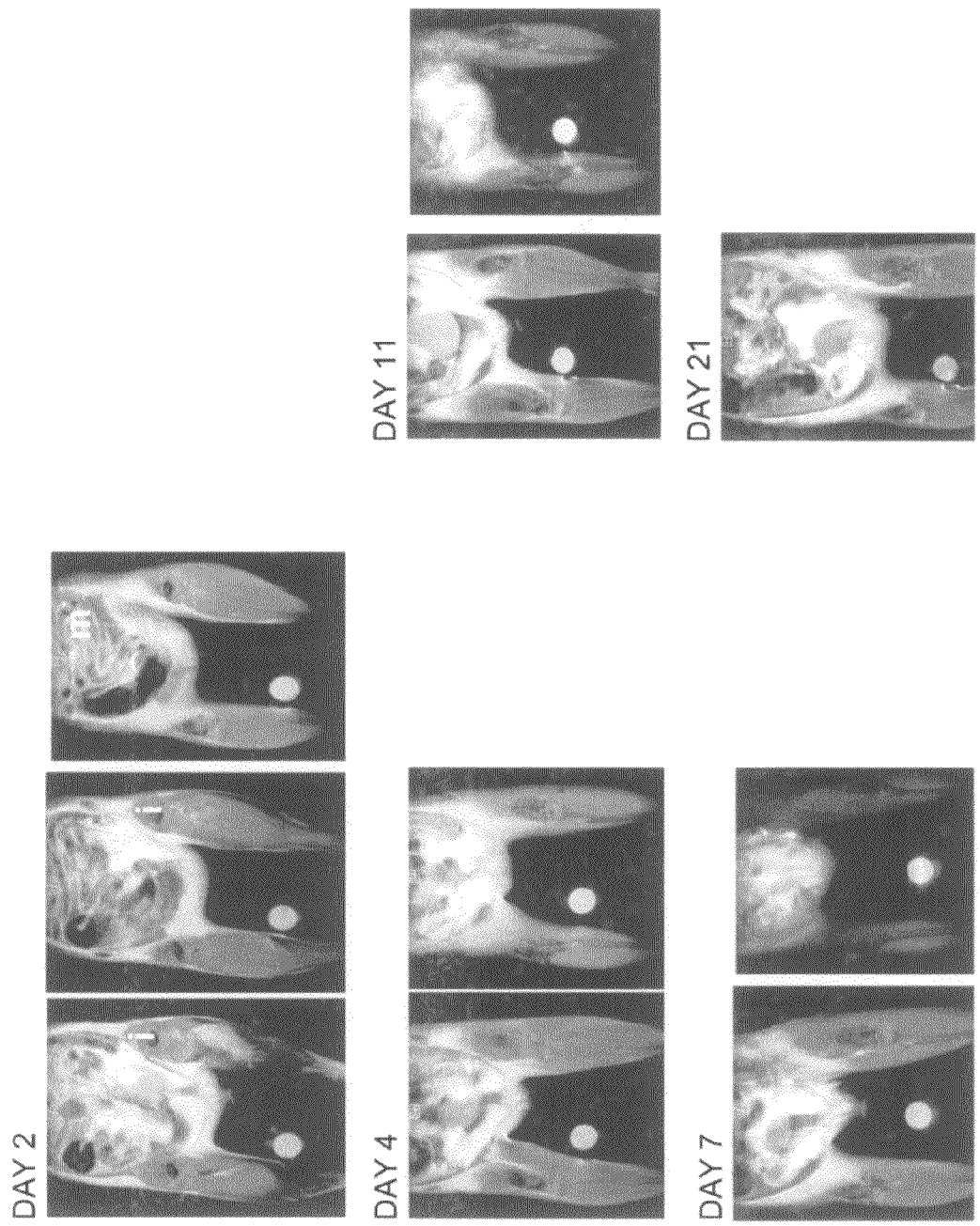
FIG. 13. Slices containing the inguinal lymph nodes at various time points after the injection of PFPE labeled T cells. The T cells are visible in the inguinal node (i, 4 day panels) only on the side where ovalbumin/IFA was administered. Some localization to the mesentery nodes is also observed (m, 4 day panel). Only slices with appreciable $^{19}$F signal are shown.

Data presented in WO2005072780 demonstrated that immune cells and other cell types cells could readily be labeled with a fluorocarbon imaging reagent ex vivo, and that labeled cells could be detected in vivo. In this section, data demonstrating the further feasibility of the disclosed methods is presented, including data demonstrating the in vivo quantification of labeled cells. The overall scheme is summarized in FIG. 1. The exemplary embodiment of the disclosure uses fluorine-based imaging reagents to label cultured cells. Labeled cells are introduced into a living subject and tracked in vivo using $^{19}F$ MRI or MRS, as shown in FIG. 2 $^{19}F$ MRI images are overlaid with $^1H$ MRI images to establish the anatomical location of the labeled cells as shown in FIGS. 2, 9A and 13. In the examples, quantification of labeled cells in an ROI in the subject is measured using the $^{19}F$ intensity of the ROI and a calibrated external $^{19}F$ reference.

1. Emulsion Preparation

Figure 3B:
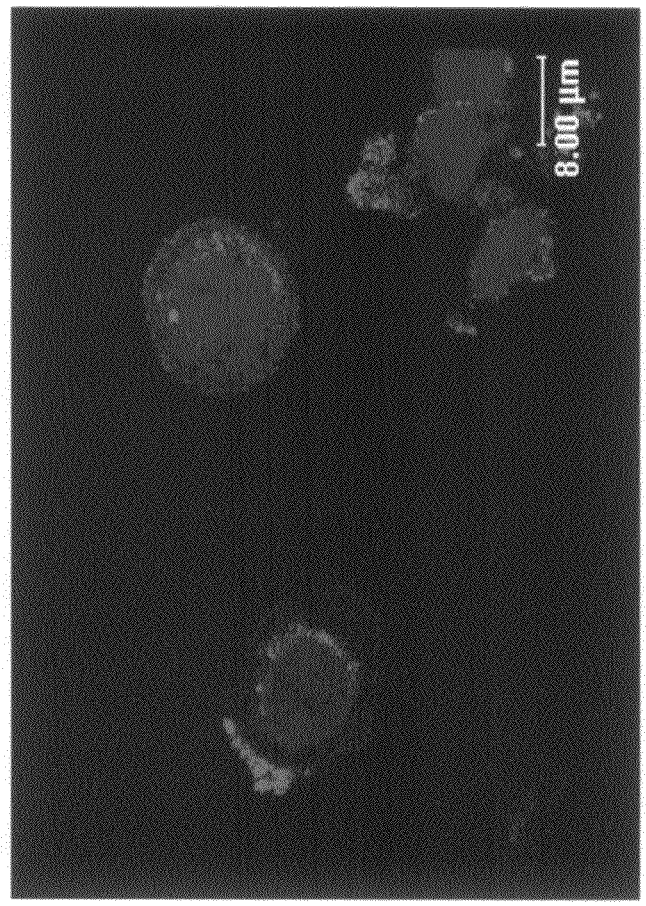
FIGS. 3A-3D. T cells are efficiently labeled with PFPE nanoparticles ex vivo. (a) Shows a $^{19}F$ NMR spectrum of pelleted, labeled ($1\times10^6$) T cells. The PFPE has two peaks, one at −92 ppm and the other at −79 ppm. A capillary containing trifluoroacetic acid (TFA) was used as a reference alongside the cell pellet and shows a peak at −76 ppm. The $^{19}F$ NMR was measured at 470 MHz. (b) Confocal fluorescence micrographs of labeled, activated T cells. The PFPE nanoparticles were treated with DiI (pink) before cell labeling. Cell nuclei are TOTO3 stained (blue), which also weakly stains the cytoplasm. Nanoparticles are visible both on the cell surface and intracellularly. The scale bar represents 8 μm. (c) Molecular structure of the PFPE, a dimethyl ester derivative of PEG 600, with approximately 40 F's per molecule. This molecule can be emulsified, for example, using Pluronic L35. (d) Emulsion particle size as seen by dynamic light scattering (left panel) and electron microscopy (EM) (right panel). The dynamic light scattering measured the size distribution of the nanoparticles in PBS. The plot shows the mean number of nanoparticles (%) versus the mean particle diameter (nm). The nanoparticles have an average diameter of 103±4 nm.
Figure 3A:
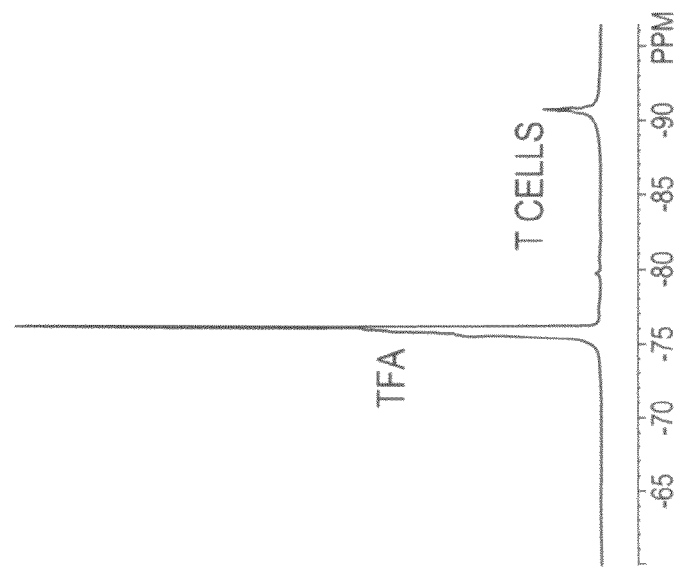
Figure 3C:
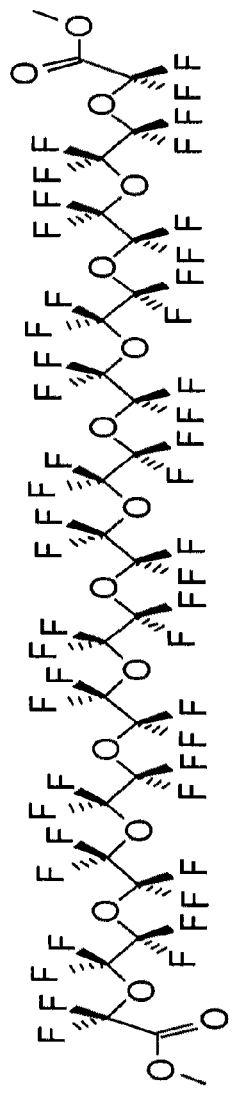
Figure 3D:
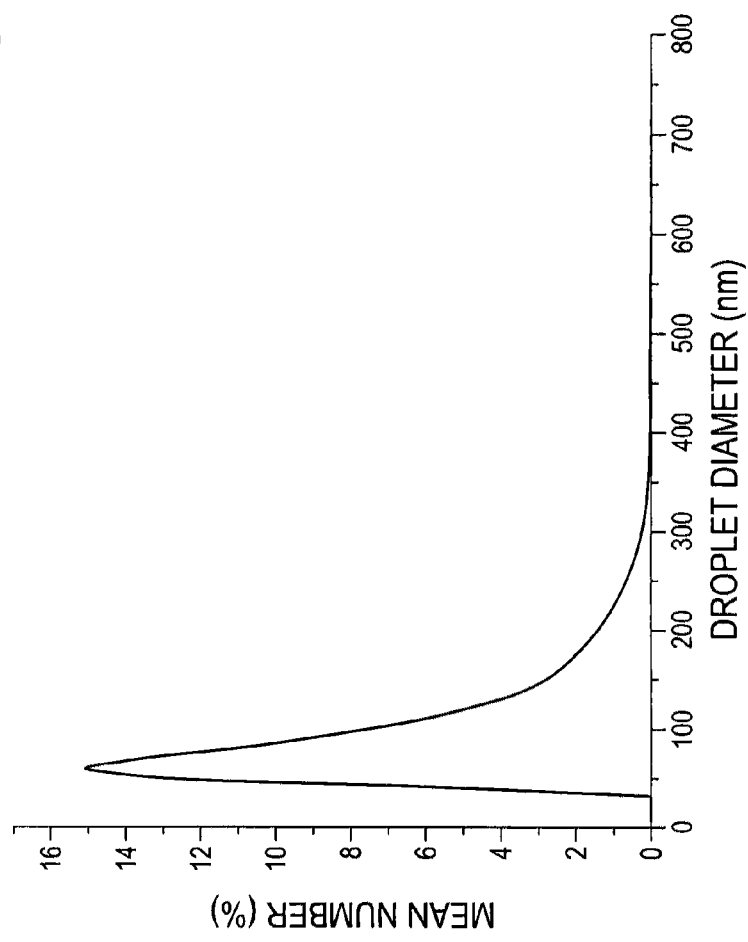

A label formulation was prepared, consisting of a 1:1 molar ratio of the PFPE (Exfluor, Round Rock, Tex.) molecule shown in FIG. 3c with Pluronic L-35 (Sigma-Aldrich, St. Lois, Mo.). The PFPE and water were autoclaved, and the Pluronic L-35 was 0.22 µm filtered to ensure sterility. The mix was emulsified by probe sonication on ice. Light scattering using standard means was performed on the emulsified product to confirm particle size distribution as shown in FIG. 3d. Dynamic light scattering was done using a Malvern Zetasizer Nano ZS (Malvern Instruments, Worcestershire, UK) instrument. The nanoparticles have an average diameter of 103±4 nm.

2. Cell Labeling

T cells were extracted from the mouse spleen, and single cell suspensions of splenocytes were sorted using a MACS pan T-cell isolation kit (Miltenyi Biotec, Auburn Calif.). (See Example 6 for additional details.) T cells were activated before labeling by incubating them in plates coated with anti-TCR, anti-CD-28, and IL-2 for 3 days. The cells were maintained in RPMI with 10% fetal bovine serum (FBS), 100 µg/ml each of streptomycin and penicillin, and supplemented with 10 µg/ml IL-2 and 1 µl/ml of 2-mercaptoethanol. Cells were then harvested and resuspended in fresh medium at 2 million/ml. Label was prepared by mixing 2 µl of the PFPE emulsion and 8 µl of FuGene 6 (Roche, Inc., Indianapolis Ind.) in 300 µl FBS-free media for 20 min before adding to the cell suspension at 2 µl label/ml cells for 3 hrs. Cells were washed in PBS twice and resuspended in 300 µl HBSS before administration to the subject. Between four and eight million cells were used for each experiment (n=6).

$^{19}F$ NMR, shown in FIG. 3a, was used to confirm cell labeling and for quantification of the intracellular dose (i.e., $F_c$ or "cellular dose") of the labeling reagent. FIG. 3a shows a $^{19}F$ NMR spectrum of activated, labeled T cells. The spectrum of the linear PFPE molecule has two peaks, a major $CF_2$ peak at −92 ppm and a minor peak at −79 ppm from the $CF_2$ end groups (FIG. 3c). The ratio of the spectral weight of these peaks is 10:1, and generally the minor peak is below MRI detectability in vivo. The third peak, at −76 ppm, is from the TFA reference in a sealed capillary. We calculated the mean $^{19}$F content per cell ($F_c$) to be $2.2\times10^{13}$ fluorine atoms post-labeling. Confocal microscopy of the labeled cells confirmed that the PFPE label distribution is intracellular and also on the cell surface (FIG. 3b).

Figure 4A:
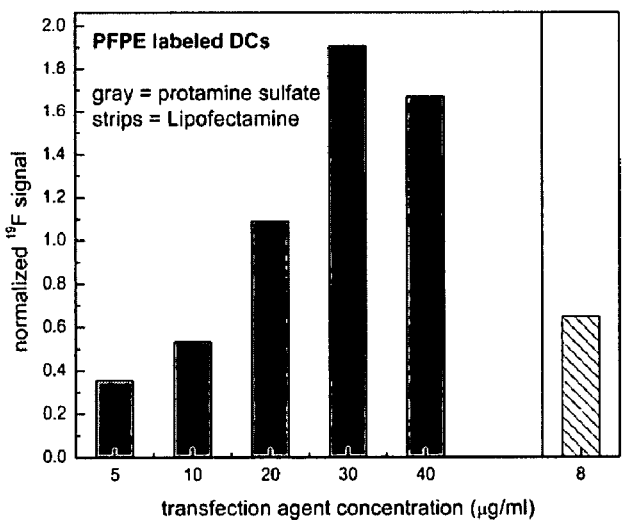
FIGS. 4A-4B. In vitro cell labeling with fluorocarbons (i.e., PFPE) emulsions using various transfection agents. The agents shown are protamine sulfate (Sigma, Inc.), Lipofectamine (Invitrogen, Inc.), DOTAP (Roche, Inc.), and FuGene (Roche, Inc.). Examples are given for typical cell types, including dendritic cells (DCs) (panel a) and T-cells (panels b). In panels a-b, different cationic transfection reagents were used to significantly boost uptake in culture of the PFPE particles and reduce labeling incubation time to of order of 1-3 hours. The $^{19}F$ content was assayed using integrated $^{19}F$ NMR spectra of labeled cell pellets, where values were normalized to cell number and a TFA reference located next to the cell pellet.
Figure 4B:
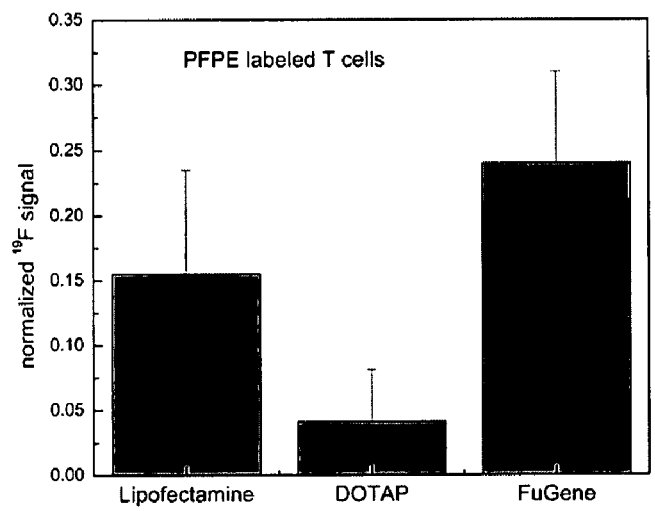

Besides FuGene, many other transfection agents can be used to boost the PFPE labeling of many cell types. FIG. 4b shows that T cells can also be labeled with Lipofectamine (Invitrogen, Inc., Carlsbad, Calif.) and DOTAP (Roche). In other examples shown in FIG. 4a, DC labeling can be boosted with the aid of the small cationic protein, protamine sulfate, and the labeling results give the same order of magnitude as what is achievable with Lipofectamine (FIG. 4a). In the examples shown in FIG. 4, the $^{19}$F content was assayed using the integrated $^{19}$F NMR spectrum of the labeled cell pellet, where values were normalized to cell number and a TFA reference located next to the cell pellet.

Figure 5A:
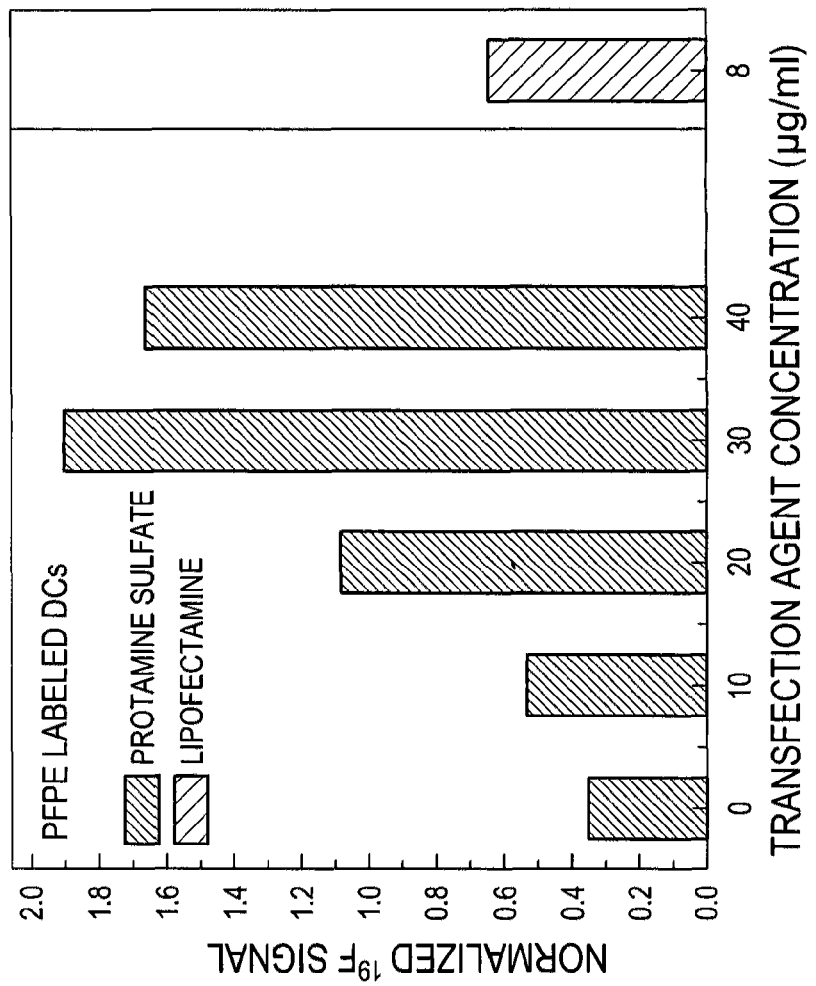
FIGS. 5A-5B. In vitro cell labeling with perfluorocarbon (i.e., PFPE) emulsion particles using electroporation. DCs were electroporated in culture media. Panel a shows a typical $^{19}F$ NMR spectrum of a pellet of labeled cells. Panel b shows the $^{19}F$ content as a function of electoporation voltage, at fixed PFPE concentration in the medium. The intracellular $^{19}F$ content was assayed using $^{19}F$ NMR spectroscopy of labeled cell pellets, where values are normalized to cell number and a TFA reference located next to the cell pellet.
Figure 5B:
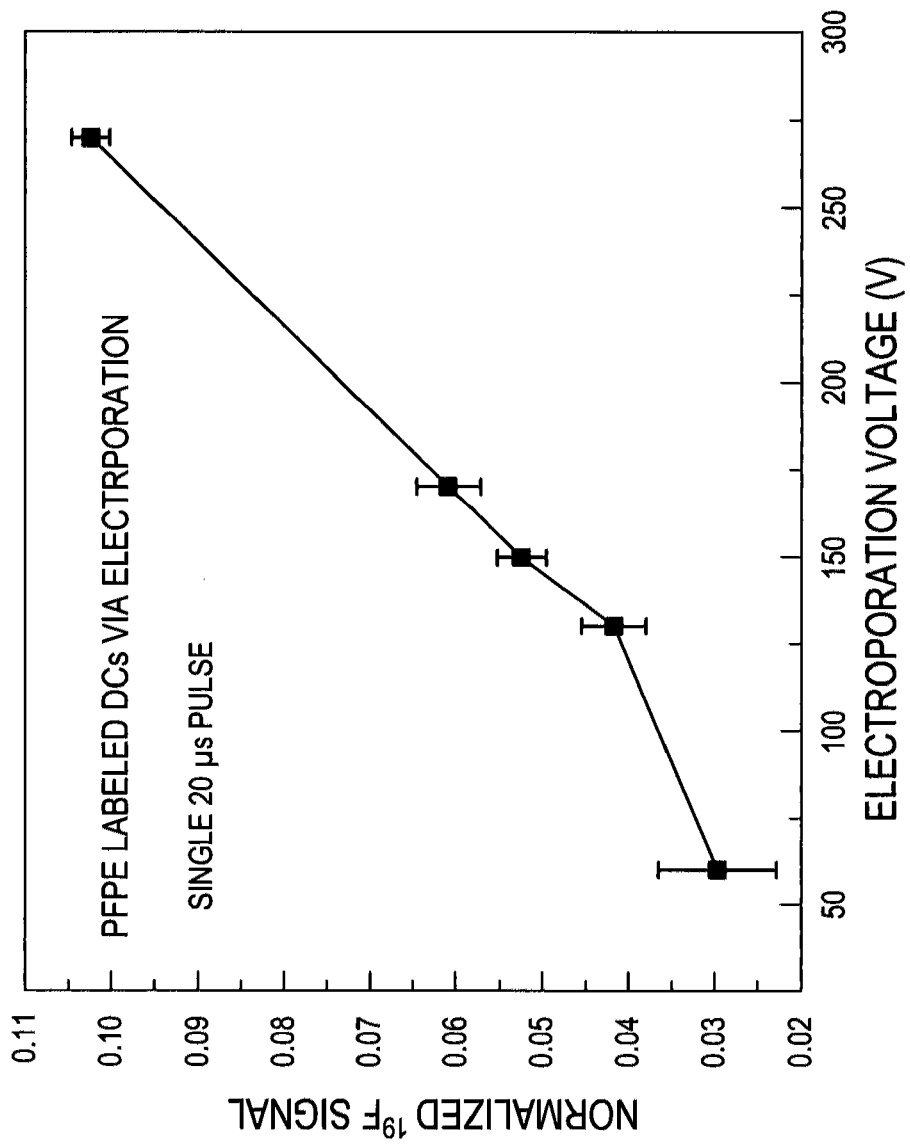

As alternative to the use of transfection agents, one can use cell electroporation to boost PFPE labeling. FIG. 5a shows a $^{19}$NMR spectrum of a pelleted DCs that have been electroporated with PFPE emulsion particles while in culture. By varying the electroporation parameters, such as the electroporation voltage, one can systematically vary and optimize the amount of label internalized into the cells, as shown in FIG. 5b. As above, the $^{19}$F content was assayed using the integrated $^{19}$F NMR spectrum of the labeled cell pellet, where values were normalized to cell number and a TFA reference located next to the cell pellet. In the electroporation experiments a commerecially available apparatus was used (ECM 830, BMX, Inc., Holliston, Mass.). Before electroporation DCs were resuspend in HBSS so that each sample had about 1-1.6 million cells in a 700 µl in the cuvette. The PFPE emulsion (2 µl/ml) was added directly into the cuvette. For the data shown in FIG. 5b, a single 20 µs electroporation pulse was used. One minute after the pulse, 1 ml of culture media was added, and the samples were kept on ice for ~10 minutes. The cells were then washed twice in PBS to remove excess (i.e, unincorporated) PFPE.

3. $^{19}$F Labeling Does Not Affect Cell Behavior

Figure 6:
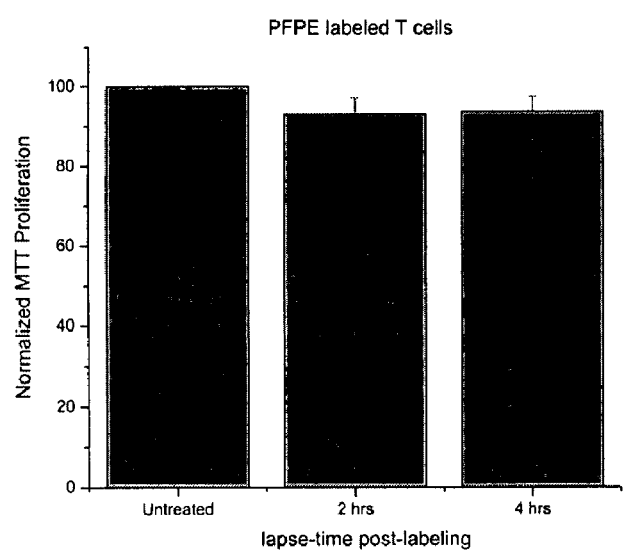
FIG. 6. MTT toxicity assay of PFPE labeled primary T-cells in vitro. Minimal toxicity is observed due to PFPE labeling. Data is taken from aliquots of cells taken at 2 hrs and 4 hrs after labeling. In this example a transfection agent (FuGene) was used to boost uptake. Data was normalized to the untreated control, multiplied by 100, and the experiment was averaged over n=9 trials.

T cell labeling was optimized for maximal uptake and minimal cytotoxicity. Label uptake was measured through $^{19}$F NMR and cytotoxicity through standard assays, such as trypan blue exclusion and MTT assays. To confirm viability and phenotype of labeled T cells, we performed several in vitro assays. Labeled cell viability, assayed using trypan blue immediately after labeling, showed 94±3.7% viability relative to untreated controls, where the error bar is the standard deviation for n=6 wells; at 48 hours post-labeling, the cells displayed 95±6% viability (n=3). The MTT assay (ATCC, Manassas, Va.) was carried out on T cell aliquots taken at 2 and 4 hours post-labeling. Data were normalized to untreated controls. Labeled cells showed minimal decrease in the MTT relative to controls, as shown in FIG. 6. Thus, these data suggest that the label process causes no overt toxicity. In addition, the lack of cytotoxicity was confirmed by the trypan exclusion assay and direct cell counts.

Figures 7A, 7B, 7C:
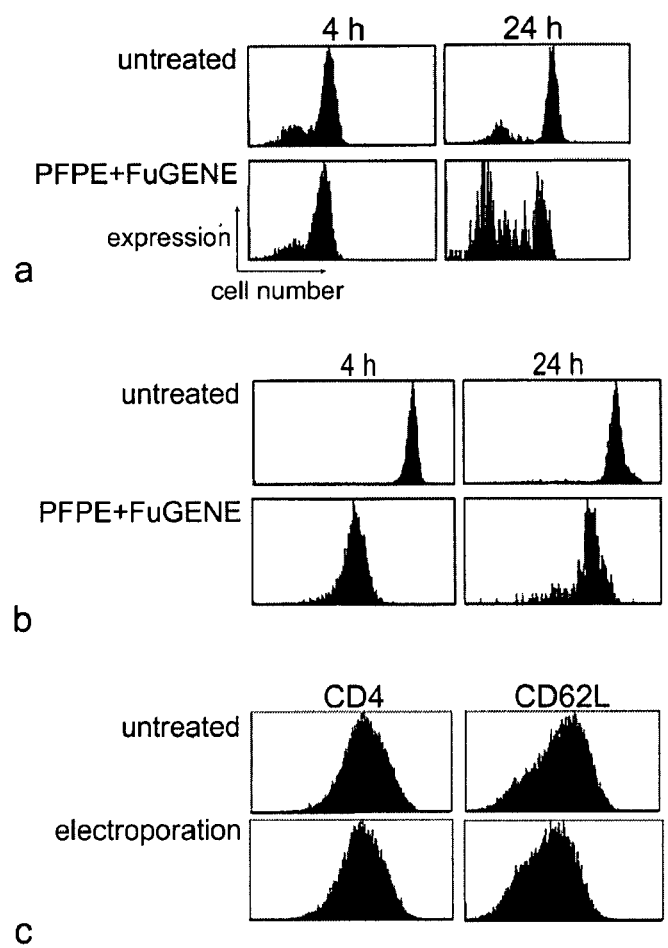
FIGS. 7A-7C. FACS results in PFPE labeled T cells. Panels (a) and (b) are CD62L+ and CD4+ expression levels, respectively, at 4 and 24 hours post-labeling using the transfection agent method. Panel (c) shows CD4+ and CD62L+ expression at 4 hours post-labeling via electroporation.

To confirm that the labeling process itself does not activate T cells, we studied expression of the cell surface markers CD62L and CD4 on naïve BDC2.5 T cells after labeling. CD62L, a lectin-binding protein that aids in lymphocyte rolling, is expressed at high levels only on naïve T cells. We found minimal downregulation in the expression of CD62L in labeled cells compared to unlabeled cells (FIG. 7a), indicating that labeling does not activate naïve T cells. CD4, a co-receptor that interacts with the MHC II molecule, is expressed on both naïve and activated T cells. The level of CD4 expression was reduced immediately after labeling using the transfection agent, but recovered within 24 hours (FIG. 7b). To better understand the origin of this transient downregulation, T cells were labeled via electroporation, without transfection agent. There was no reduction in CD4 expression immediately after labeling using electroporation (FIG. 7c), indicating that this effect is likely an artifact from transfection agent usage.

In vitro retention studies showed that the label is retained for at least 24 hours. Intracellular localization of the label was confirmed by electron microscopy.

Correct in vivo cell homing and function of labeled cells was confirmed using fluorescence microscopy (FIG. 8). To test this, we investigated T cell infiltration into the pancreas in a Type I diabetes model. For all in vivo experiments we used an established adoptive transfer method that has been shown to result in reproducible diabetes induction (22,23). The BDC2.5 T cells (~$4\times10^6$) were purified, activated in vitro, PFPE labeled, and injected i.p. into a recipient NOD SCID mouse (Jackson Labs, Bar Harbor Me.). All T cells in the NOD BDC-2.5 transgenic only recognize a peptide derived from a specific B cell granule protein. Adoptive transfer of NOD BDC 2.5 T cells is known to cause diabetes in NOD SCID mice. All mice were 8-10 week old, and each mouse received ~5 million labeled cells. Control mice received an equivalent amount of label in buffer. All NOD SCID mice received 200 mg/kg of cyclophosphamide (Sigma Aldrich) in PBS i.p. 24 hrs before cell transfer.

FIG. 8 confirms that the PFPE-labeled cells are able to home to the pancreas, showing that the labeling process does not interfere with cell function in vivo. The injected cells were only visible in or around islets and blood vessels, as expected. This suggests specific homing to the islets, rather than merely accumulation of cells in the pancreas. These micrographs also show strong CD4+ immuno-staining, implying strong CD4 expression levels. All detected T cells in the pancreas are those that were labeled and transferred, since NOD SCID mice lack endogenous lymphocytes.

4. In Vivo Cell Tracking

In vivo MRI experiments were used to confirm that labeled cells can be detected in the appropriate organs (e.g., pancreas). Purified T cells from transgenic NOD BDC 2.5 mice were activated and labeled in vitro, as described above, and transferred i.p. into host NOD SCID mice (Jackson Labs, Bar Harbor Me.). All mice were 8-10 week old, and each mouse received 3-8 million labeled cells. Control mice received an equivalent amount of emulsified PFPE in buffer without cells. All NOD SCID mice received 200 mg/kg of cyclophosphamide (CY) i.p. 24 hours before cell transfer.

Animals were imaged 48 hours after cell transfer. Prior to MRI, mice were anesthetized, intubated, and connected to a mechanical respirator. A capillary tube containing a $^{19}$F reference, comprised of the PFPE emulsion containing $10^{18}$ fluorine atoms per ml of PBS, was placed next to the animal in the image field of view. MRI was carried out using an 11.7 T, 89 mm vertical-bore micro-imaging system (Bruker Instruments, Inc., Billerica, Mass.). $^{19}$F images were acquired using a RARE sequence with TR/TE=1000/6.4 ms with a RARE factor of 8, a matrix of 164×32 image points, and a slice thickness of 2 mm. $^1$H imaging was performed immediately afterwards using a 2DFT spin-echo sequence, with TR/TE=1200/22 ms, 512×256 image points, and the same geometrical coordinates as the $^{19}$F. All in vivo imaging was respiratory-gated, and animal temperature was maintained at 37° C.

A representative $^{19}$F/$^1$H composite image is shown in FIG. 9a. The anatomical $T_2$-weighted $^1$H image (grayscale) that serves as an underlay was acquired with the same slice geometry and in the same imaging session as the $^{19}$F. The $^{19}$F images through the torso show localized signal in a region consistent with the pancreas (pseudo-color, FIG. 9a). No signal was detected in any other regions, including the liver and spleen, indicating that the cells are not being taken up by these organs in significant numbers. Moreover, cells that remained in circulation or that were localized at low concentrations in other organs or tissues are not detected. The complete lack of signal in any other region shows specific trafficking to the pancreas, which is the expected immunological response in vivo.

To confirm that the detected signal was due to specific T cell homing, we carried out two control in vivo MRI experiments in the NOD model. These employed i.p. injections of either cell-free PFPE nanoparticles or non-specific, labeled T cells. Imaging results after 48 hours (FIG. 9b) show $^{19}$F accumulation from cell-free PFPE in regions in or near the bladder but not the pancreas. The second control employed purified non-specific CD4$^+$ T cells from MHC-mismatched BALB/c mice. Since T cells recognize antigen in the context of the MHC, BALB/c T cells are not expected to carry out specific homing in NOD mice. FIG. 9c shows that after 48 hours no $^{19}$F was detected in or around the pancreas.

5. Quantification Through In Vivo MRI

Figure 9D:
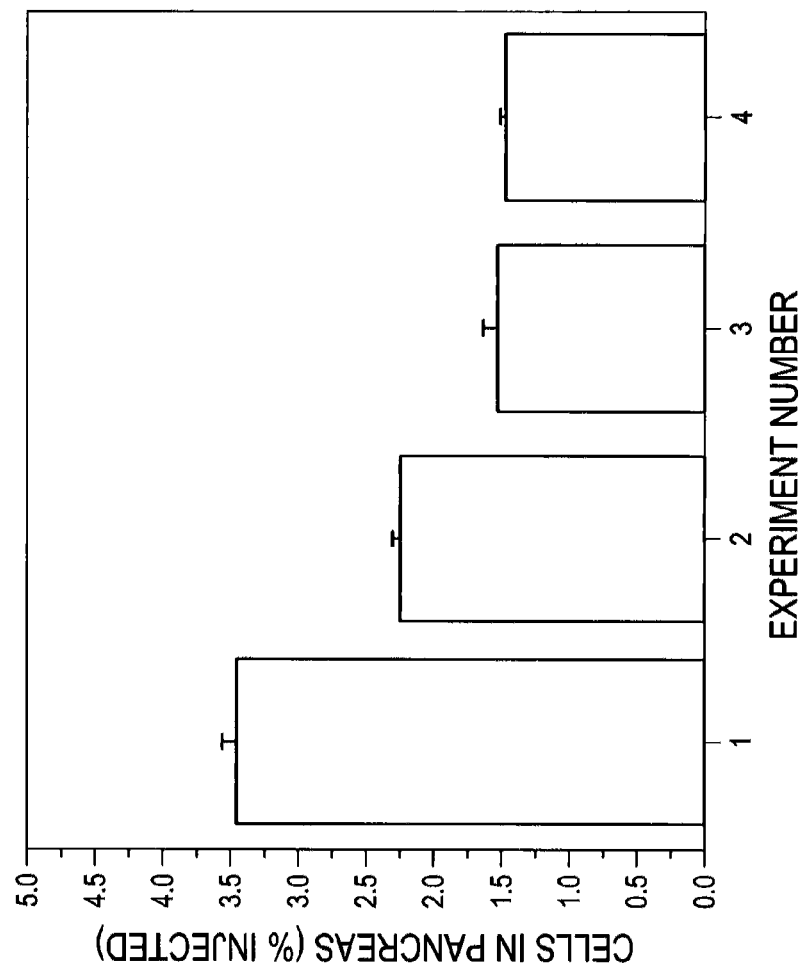

Using the in vivo $^{19}$F MRI data we applied an algorithm (See Example 6) to quantify the effective number of transferred cells within regions of interest. FIG. 9d shows a summary of the cell quantification results in pancreata from n=4 animals. The number of apparent T cells detected ranged from approximately 1.5-3.4% of the total transferred cells (FIG. 9d). The mean number of cells detected for the cohort was 2.2±0.9% of the total transferred cells, where the uncertainty is the standard deviation (n=4). The average cell density in vivo was ~28,000 cells/voxel in the pancreas.

Figure 10A:
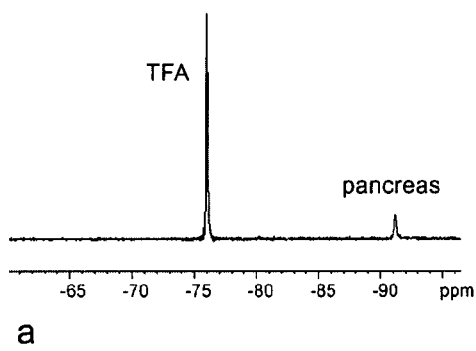
FIGS. 10A-10B. $^{19}$F NMR spectra of excised pancreas (a) and spleen (b) from an NOD SCID mouse inoculated with labeled T cells. $^{19}$F NMR on whole, fixed organs was performed after in vivo MRI (FIG. 9a). The $^{19}$F peak is detected in the pancreas (a), but is absent in the spleen (b), consistent with the in vivo MRI findings (FIG. 9a). The TFA $^{19}$F reference was located in a sealed capillary adjacent the organ. A larger number of averages (8-times) were used to acquire (b) compared to (a).
Figure 10B:
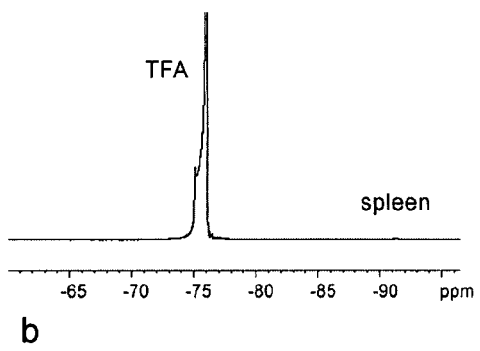

We independently validated the quantity of labeled cells homing to the pancreas via high-resolution $^{19}$F NMR spectroscopy in excised organs (FIG. 10). The mouse was sacrificed after the MRI scan, and we harvested and fixed the pancreas and other organs. FIG. 10a shows a $^{19}$F NMR spectrum from an intact, excised pancreas. The area under the $^{19}$F NMR peak of the pancreas, measured with respect to a TFA reference sample in the same NMR tube, gives the total $^{19}$F content in the organ. In the pancreata, the mean number of cells detected for the cohort using NMR was 2.9±0.3% of the total transferred cells, where the uncertainty is the standard deviation for n=4. Thus, the mean cell numbers obtained by NMR in the excised organs is consistent with the values obtained using in vivo $^{19}$F MRI. The excised spleens showed minimal $^{19}$F NMR signal (FIG. 10b), as is seen in the MRI data.

Figures 11A, 11B:
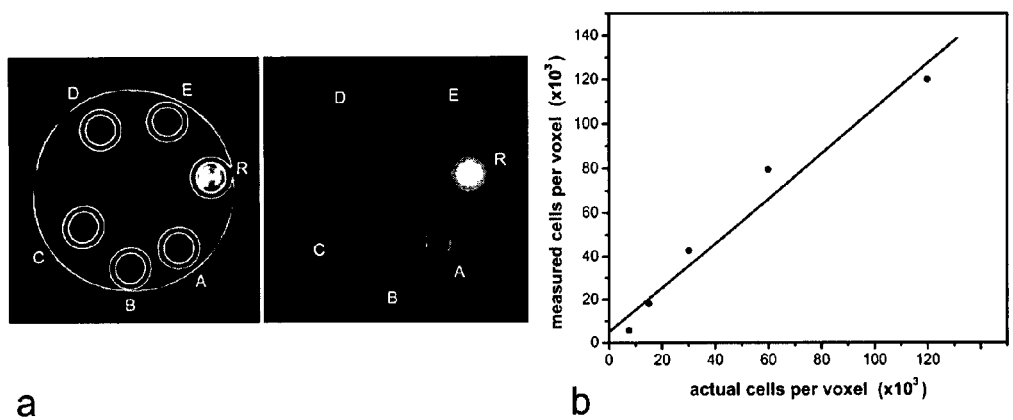
FIG. 11. Phantom studies validating T cell quantification methods using $^{19}$F MR images. Panel (a) shows a composite $^{19}$F/$^1$H image (left) and intensity-rescaled $^{19}$F image (right) through a phantom containing capillary tubes containing different densities of labeled T cells suspended in agarose, where capillary A=12, B=6, C=3, D=1.5, and E=0.75 ($\times10^4$) cells/voxel, and R is a calibrated $^{19}$F reference capillary. The $^{19}$F image (a, right) was rescaled to show the intermediate cell densities, i.e., capillaries B, C, D. Capillary E (7,500 cells/voxel) is not visible in this scaling, however, our quantitative analysis is able to detect and measure cells in this sample. These data were acquired using similar imaging parameters as FIG. 9. A $CF_2$ endgroup chemical shift artifact, or 'ghost', from the highly-concentrated R capillary is observed near capillary A. Panel (b) shows the actual versus MRI-measured cell numbers in the phantom. The Pearson correlation coefficient is 0.98. The linear fit is a guide for the eye. The error bars for the ordinate are not shown and are smaller than the data point symbol.

As an additional verification of the accuracy of the MRI cell quantification methods, we imaged a phantom containing a range of known densities of fixed, labeled T cells suspended in agarose. FIG. 11a displays a composite $^{19}$F/$^1$H image of the phantom and the $^{19}$F image alone; this image was acquired with the same parameters that were used for the in vivo data (FIG. 9a). The 'ghost' seen adjacent capillary A is a CF$_2$ endgroup chemical shift artifact from the highly concentrated reference capillary, R. We calculated the number of apparent cells per voxel directly from the $^{19}$F MR images using the same methods that were used for the in vivo data. The measured results are 120, 80, 43, 18 and 5.7 ($\times 10^3$) cells/voxel, for capillaries A, B, C, D and E respectively (FIG. 11b). The Pearson correlation coefficient was 0.98, when compared to the actual cell numbers per voxel. Overall, the phantom experiment demonstrated reasonable accuracy of the quantitative methods, with a minimum cell detection limit of approximately 7,500 cells/voxel.

6. Methods for Examples 1-5

Label Synthesis and Characterization

PFPE emulsions were prepared using a 1:1 molar ratio of autoclaved perfluoro-polyethelene glycol (molecular weight ~1500, Exfluor, Round Rock, Tex.) and sterile filtered Pluronic L35 (Sigma-Aldrich, St. Louis, Mo.). Emulsification was by probe sonication using a Sonifier Cell Disruptor (Misonix Inc., Farmingdale, N.Y.). The average emulsion particle diameter was determined to be 103±4 nm by dynamic light scattering using a Malvern Zetasizer Nano ZS instrument (Malvern Instruments, Worcestershire, United Kingdom). Fluorescent PFPE emulsion particles were prepared by mixing 2 μl PFPE emulsion, 1 μg dialkylcarbocyanine dye (DiI, Molecular Probes-Invitrogen, Carlsbad, Calif.) dissolved in dimethyl sulfoxide (1 μl), 8 μl FuGENE 6 (Invitrogen), and 100 μl Roswell Park Memorial Institute (RPMI) media.

T Cell Purification, Activation and Labeling

T cells from the BDC2.5 TCR transgenic mouse were purified from single cell suspensions of splenocytes using a magnetic cells sorting (MACS) pan T-cell isolation kit (Miltenyi Biotec, Auburn, Calif.). Cell were grown in RPMI with 10% fetal bovine serum (FBS; both from Gibco, Carlsbad, Calif.), 100 μg/ml each of streptomycin and penicillin, and 1 μl/ml of 2-mercaptoethanol. Cells were activated in vitro by a three day incubation on plates coated with anti-TCR antibody in the presence of 1 μg/ml anti-CD28 and 10 U/ml IL-2. Cells were then harvested and resuspended in fresh medium at 2×10$^6$/ml. The PFPE emulsion (2 μl) was pre-mixed with 8 μl of FuGENE 6 (Roche, Indianapolis, Ind.) transfection agent in 300 μl FBS-free media for 20 minutes; this mix was added to the cell suspension at 2 μl/ml and incubated for 3.5 hours. Cells were washed in phosphate buffered saline (PBS) twice and resuspended in 300 μl Hank's balanced salt solution (HBSS) prior to inoculation. Alternatively, electroporation cell labeling was carried out on aliquots of 5×10$^6$ T cells in HBSS. A unidirectional 80 mV pulse of 20 ms length was delivered via a BTX 830 electroporator (Harvard Apparatus, Holliston, Mass.). Cells were then incubated on ice for 10 min before the addition of media and a further incubation of 4 h at 37° C.

Cellular Toxicity, Proliferation and Phenotype

Cellular viability was measured using the methyl thiazole tetrazolium (MTT) assay (ATCC, Manassas, Va.) according to the manufacturer's instructions. Cell aliquots were assayed at two, four and 48 hours after labeling. Cellular toxicity of labeled cells was also assessed using a trypan blue exclusion assay; aliquots of cells were mixed with trypan blue and then counted in a hemocytometer. For the fluorescence activated cell sorting (FACS) analyses, cells were stained using either fluorescein isothiocyanate (FITC) or phycoerythrin (PE) conjugated antibodies against CD4 and CD62L (PharMingen, San Diego, Calif.). The expression levels of these markers were determined by flow cytometry on a LSRII FACS instrument (Becton Dickinson, Mountain View, Calif.).

Murine Diabetes Model

Experiments were carried out in accordance with the guidelines provided by the Carnegie Mellon Institutional Animal Care and Use Committee (IACUC) and the National Institute of Health Guide for the Care and Use of Laboratory Animals. NOD SCID and BALB/c mice were obtained from Jackson Laboratories, and NOD BDC2.5 mice were bred in house. All mice were housed in the animal facilities at the University of Pittsburgh or at the Pittsburgh NMR Center for Biomedical Research at Carnegie Mellon University. For the adoptive transfer experiments, purified T cells from the spleens of NOD BDC2.5 mice were activated in vitro, labeled, and transferred intraperitoneally (i.p.) into host NOD SCID mice. Recipient mice were pre-treated i.p. with 200 mg/kg of cyclophosphamide (Sigma-Aldrich) in PBS 24 hours before cell transfer (20). All mice were 8-10 weeks old, and each mouse received 2-6×10$^6$ labeled cells i.p.

In vivo control experiments were carried out in exactly the same manner, except mice received either cell-free PFPE in HBSS at a $^{19}$F dose equivalent to 1×10$^7$ labeled T cells, or received labeled, activated T cells from MHC-mismatched BALB/c mice in place of the BDC2.5 T cells.

Optical Microscopy

In vitro activated T cells were incubated with the fluorescent emulsion preparation (described above) and washed twice. T cells were incubated on poly-L-lysine coated glass coverslips for 30 min and then fixed in 1% paraformaldehyde (PFA). The fixed cells were mounted in VectaShield (Vector Labs, Burlingame, Calif.) mounting medium with a 10 μg/ml TOTO-3 nuclear stain (Molecular Probes-Invitrogen) after RNAse treatment. The slides were then imaged using a Leica TCS SP2 spectral confocal microscope (Leica Microscopes, Inc., Exton, Pa.).

Histological sections were also prepared of the pancreas from NOD SCID mice that had received PFPE labeled NOD BDC2.5 T cells. The mouse was perfused with 2% paraformaldehyde (PFA) 48 hours after cell transfer, and its pancreas was excised and immersed in 2% PFA. Frozen sections (6 μm) were mounted on glass slides, stained, and viewed in an Olympus BX51 microscope (Olympus America, Inc., Center Valley, Pa.). Cell nuclei were stained using 4'-6-Diamidino-2-phenylindole (DAPI), and actin was stained with phalloidin. T cells were immuno-stained using rat anti-mouse CD4 primary (Pharmingen-BD Biosciences, San Jose, Calif.) and goat anti-rat Cy3 secondary antibodies (Jackson ImmunoResearch Laboratories, Inc., West Grove, Pa.). Insulin was stained using an anti-insulin rabbit polyclonal (Santa Cruz Biotechnology, Inc., Santa Cruz, Calif.) and goat anti-rabbit Cy5 secondary antibodies (Jackson ImmunoResearch Laboratories, Inc.).

NMR

All $^{19}$F NMR measurements were made at 470 MHz using a Bruker DRX500 spectrometer (Bruker BioSpin, Inc. Billerica, Mass.). The mean intracellular $^{19}$F dose per cell, $F_c$, was measured by pelleting 1×10$^6$ labeled cells in an NMR tube. The NMR tube also contained a small sealed capillary containing a 5 μl of 5% v/v trifluoroacetic acid (TFA), providing a calibrated quantity of $^{19}$F spins. The $F_c$ was calculated from the ratio of the integrated areas of the PFPE and the TFA spectra. For whole organ NMR, mice were sacrificed immediately after MRI, and the organs were harvested and fixed with 4% PFA for 48 hours. The fixed organs were placed in NMR tubes that also contained a sealed capillary containing the TFA $^{19}$F reference solution. All $^{19}$F spectra, except where noted, were acquired using a recycle delay of 8 s, a 12 μs pulse width, a spectral width of 20 kHz, 256 averages, 2048 acquisition points, and a 90° flip angle.

MRI

Before imaging, mice were anesthetized with a ketamine/xylazine cocktail and an IP catheter was secured with sutures and connected to a syringe pump to infuse additional cocktail into the mice for the duration of the experiment (2-3 hours). A maximum total dose of approximately 0.33 mg ketamine and 0.02 mg xylazine was delivered via an incremental step-down dose protocol. During the scan the mouse was intubated and connected to a mechanical ventilator (Harvard Apparatus Inc., Hilliston, Mass.) delivering a 2:1 $O_2/NO_2$. Mice were positioned in a cradle and imaged using an 11.7 T, 89 mm vertical-bore micro-imaging system (Bruker). A volume birdcage-type resonator was used that could be tuned to either 470 MHz for $^{19}$F or 500 MHz for $^1$H. The mouse temperature was maintained at 35-37° C. using a water-filled jacket surrounding the animal cradle that was connected to a regulated closed-cycle water bath. A sealed tube containing dilute PFPE emulsion was placed by the torso in the image field of view and served as a calibrated external $^{19}$F reference. $^{19}$F images were acquired using a rapid acquisition with relaxation enhanced (RARE) sequence with a RARE factor equal to eight, TR/TE=1000/6.4 ms, 64×32 image points, and a 50 kHz bandwidth. $^1$H images were acquired using a 2DFT spin-echo sequence with TR/TE=1200/22 ms and 512×256 image points. Eight contiguous, 2 mm thick slices through the torso were acquired for both $^{19}$F and $^1$H with exactly the same coordinates. The field of view was 5×2.8 cm for all acquisitions. All MRI excitations were respiratory-gated.

To validate the MRI cell quantification method, we constructed a phantom containing 5 mm capillaries with different densities of labeled T cells suspended in 2% agarose in PBS. The cell densities used were 87.0, 43.5, 21.9, 10.8, and 5.4 cells/nl, which correspond to 12, 6, 3, 1.5, and 0.75 (×10$^4$) cells/voxel, respectively. A $^{19}$F reference capillary of dilute emulsion was also placed in the phantom, as is used for the in vivo imaging. All capillaries were embedded in agarose, and imaging was performed at 37° C. using the same birdcage resonator and pulse sequence parameters that were used for the in vivo imaging.

Cell Quantification Using MRI

The quantity of apparent PFPE-labeled cells was calculated directly from the in vivo MRI data set, the external $^{19}$F reference, and the measured $F_c$. The calculation was performed on a per-slice basis. The real-valued noise magnitude, N, of the $^{19}$F image was determined by calculating the standard deviation of voxel values near the periphery of the image. The N can be calculated equivalently from either the real or imaginary component. Next, the magnitude values were calculated for each voxel and then corrected to compensate for the resulting Rician-distributed noise that is observed in low signal-to-noise ratio images (21). Our Rician correction reset the magnitude value, m, to a lower value, m', such that the expected value of the magnitude of (m'+0i) with noise N added to each component of m' is m=E(|(m'+n$_1$)+n$_2$i|), where E denotes expected value, and n$_1$ and n$_2$ are normally distributed random variables with zero mean and standard deviation N. The m can be estimated statistically for a given m' by finding the mean value of m for a set of random values of n$_1$ and n$_2$. Random pairs of n$_1$ and n$_2$ (1,000,000 trials) were drawn for each estimate of m. To avoid this calculation for each pixel value, m was estimated for m'=0, 0.1N, 0.2N, . . . 8N. The m' is monotonic in m, thus additional m values were calculated by interpolating the m' results using the Matlab function interp1( ). Above 8N no adjustment was made because the Rician distribution is approximately Gaussian and the correction was insignificant. Next, the average magnitude signal value, R, was calculated in an ROI containing the $^{19}$F reference. The R was calculated by interactively choosing a box containing the reference and automatically identifying voxels within it with magnitude >2.5N, thereby setting a confidence factor of >99% that the voxels scored contain actual $^{19}$F signal. This automatically calculated ROI was then dilated by one-half voxel in-plane to capture any nearby signal and account for partial volume effects. From this analysis we also calculated a parameter, r, which is the amount of $^{19}$F per voxel in the reference. Next, the total signal in the pancreas, P, was calculated. An ROI was defined by interactively choosing a box containing the pancreas, and voxels with signal >2.5N were automatically identified in the magnitude images. Again, the identified region's periphery was dilated by ½ voxel. The P was then calculated by summing the adjusted magnitude-valued signal from all of the identified voxels. The number of apparent cells contained in the pancreas, C, was calculated using the relationship C=(Pr)/(RF$_c$). The uncertainty in C was estimated by using the equation σ(P)r/(RF$_c$), where σ(P)=N$\sqrt{2n}$, i.e., the standard deviation of P, and n is the number of voxels identified as having signal. This cell quantification algorithm was also tested on the calibrated phantom containing capillaries with different known densities of labeled T cells suspended in agarose.

7. Imaging and Quantifying T Cells at the Site of Acute Inflammation

As an additional example of the utility of the fluorocarbon-based cell labeling and imaging methods, experiments in an acute inflammation model are described. We demonstrate the utility of a dual $^{19}$F MRI-fluorescent cell PFPE label in a murine model of localized inflammation. We show that activated T cells can be efficiently labeled with PFPE nanoparticles ex vivo, enabling the selective visualization of homing and quantitation of inflammatory loci in vivo via longitudinal MRI, as well as through optical imaging methods. This provides a convenient model for the study of T cell kinetics. We tracked the migration of antigen-specific T cells in vivo for up to 21 days. Cell number quantification was carried out at five time points directly from the in vivo image data sets. We found that approximately 30% of transferred cells reach the draining lymph node at 48 hours post-transfer. A fluorescent dye covalently bound to the $^{19}$F PFPE label allowed for in vivo optical imaging, as well as recovery and characterization of labeled T cells, through histology and FACS. Taken together, our data demonstrate that this novel dual-mode agent allows for the non-invasive tracking and quantification of cell migration, at least up to 3 weeks after cell transfer. The localized inflammation model described here can be used to study immunological and inflammatory aspects of multiple disease states, such as organ rejection, cancer therapy and autoimmune diseases. This example animal model and the PFPE imaging platform can also be used to quantitatively evaluate the efficacy of small molecule drugs, recombinant proteins or any other biological or cell-based therapy that is designed to modulate or attenuate the inflammatory response.

Dual-mode PFPE nanoparticles (i.e., MRI and fluorescently active) were prepared using a 1:1 molar ratio of per-fluoro-polyethelene glycol (molecular weight ~1500, Exfluor, Round Rock, Tex.) and sterile filtered Pluronic L35 (Sigma-Aldrich, St. Louis, Mo.). A fraction of the neat PFPE molecule's endgroups were covalently bound to a bright Alexa 647 fluorescent dye (Molecular Probes). Emulsification in water was performed by probe sonication using a Sonifier Cell Disruptor (Misonix Inc., Farmingdale, N.Y.). The average emulsion particle diameter was determined to be 122±17 nm, measured by dynamic light scattering using a Malvern Zetasizer Nano ZS (Malvern Instruments, Worcestershire, United Kingdom). T cells from a DO10.11 ovalbumin-transgenic mouse were purified from single cell suspensions of splenocytes using a MACS pan T-cell isolation kit (Miltenyi Biotec, Auburn Calif.). Cells were grown in RPMI with 10% fetal bovine serum, 100 μg/ml each of streptomycin and penicillin, and 1 μl/ml of 2-mercaptoethanol (Gibco-Invitrogen, Carlsbad, Calif.). Cells were activated in vitro by a three day incubation on plates coated with anti-TCR mAb in the presence of 1 μg/ml anti-CD28 and 10 U/ml IL-2. Cells were then harvested and resuspended in HBSS at 2 million/ml, with 1 μl/ml of 2-mercaptoethanol. Dilute amounts of the PFPE label were added to the media, and the cells were incubated on ice for 10 min before addition of RPMI with 10% FBS and a further incubation of 1 h at 37° C. Cells were washed in phosphate buffered saline (PBS) twice and resuspended in 300 μl Hank's balanced salt solution (HBSS) prior to inoculation. $^{19}$F NMR was carried out on representative cell pellets that were labeled as described above. Spectra were acquired using a Bruker Avance 500 MHz NMR spectrometer, where chemical shifts were referenced to TFA, as describe above. The parameter F$_c$ was calculated by pelleting a known number of labeled cells in a capillary tube alongside another tube containing a known concentration of TFA. Approximately 10 million cells were used for each in vivo experiment. Labeled T cells were injected intraperitoneally into female Balb/c (Jackson Labs) MHC-compatible mice (Day 0). These mice simultaneously received 20 μg chicken ovalbumin (Sigma) in PBS, emulsified in IFA, subcutaneously in the quadriceps, and sterile PBS was injected on the contralateral leg as a negative control. MRI was carried out on anesthetized mice using an 11.7 T, 89 mm vertical-bore micro-imaging system (Bruker, Billerica Mass.). An external reference capillary of PFPE emulsion diluted in PBS, containing $10^{19}$ fluorine atoms per ml, was place next to the animal during the imaging sessions. The $^{19}$F images were acquired with a RARE sequence with TR/TE=1000/6.4 ms using a RARE-factor of 8 and a matrix of 64×32. The $^1$H imaging was performed using a 2DFT spin-echo sequence with TR/TE=1200/22 ms and a matrix of 512×256. Eight contiguous 2 mm slices and the same slice coordinates were used for both $^1$H and $^{19}$F. All in vivo imaging was respiratory-gated, and the temperature was regulated at 37° C. In vivo optical images were acquired on a Photometrics (Tucson, Ariz.) C258 cooled CCD camera equipped with a custom filter holder and lens adapter (Bioptechs, Butler, Pa.). Animals were illuminated using four 250 W quartz-halogen illuminators (Cuda Products, Jacksonville, Fla.). Excitation filters were 530/50 nm, and emission filters were 630/30 nm. Mice were shaved before the imaging to reduce background caused by fur. The mice were sacrificed after imaging, and the lymph nodes extracted for histology.

Figure 12:
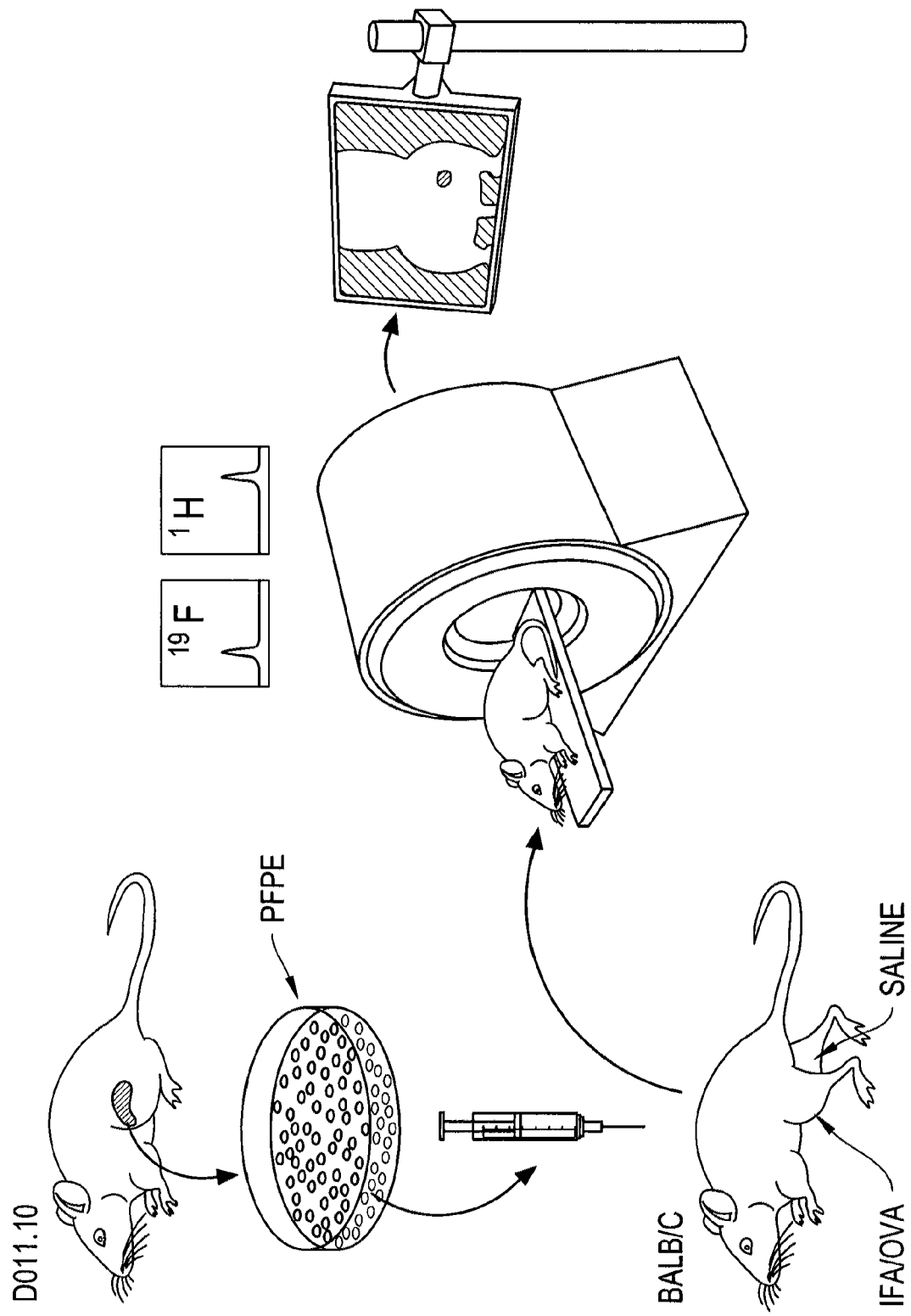
FIG. 12. Schematic showing the acute inflammation mouse model imaging experiment. Antigen-specific, MHC-matched T cells were in vitro activated prior to PFPE labeling and transfer. The host mice received s.c. ovalbumin/IFA in the quadrucepts on the right side to initiate an inflammatory response, and a PBS injection in the left leg served as a control. The mice were then longitudinally imaged using $^{19}$F and $^1$H in the same imaging session at 2, 4, 7, 11 and 21 days after cell transfer.
Figure 14:
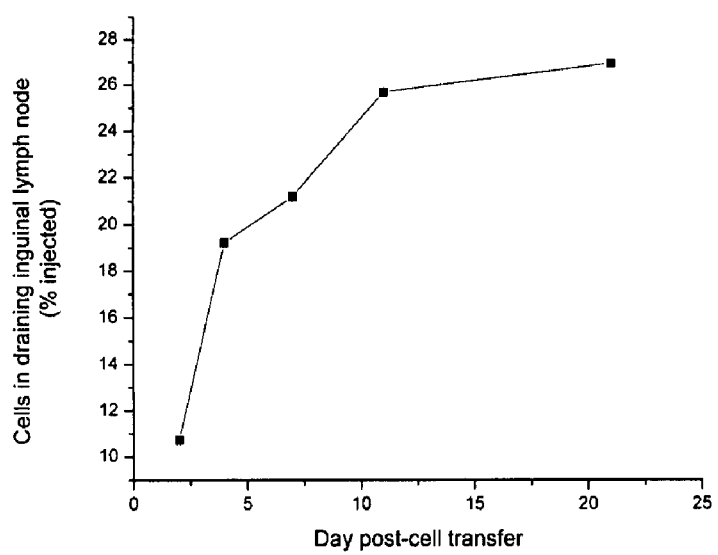
FIG. 14. Plot of average number of T cells in the inguinal lymph node at day 2, 4, 7, 11 and 21 after cell transfer. These quantitative data were measured directly from the in vivo $^{19}$F images.
Figure 15A:
FIGS. 15A-15B. In vivo optical imaging at day 4 after cell transfer. The Alexa-PFPE label is visible through the skin at day 4 in shaved mice. (a) Fluorescence is concentrated in the mesenteric region, and in the draining inguinal lymph node. The box highlights the region over the draining inguinal. (b) To compare fluorescence in the inguinal nodes, without interference from the mesenteric region, the lymph nodes were excised and imaged separately. The image is an overlay of the fluorescent image (false color) over a white light image. A difference in size as well as fluorescence is apparent in the inguinal lymph nodes, where the control lymph node is on the left.
Figure 15B:
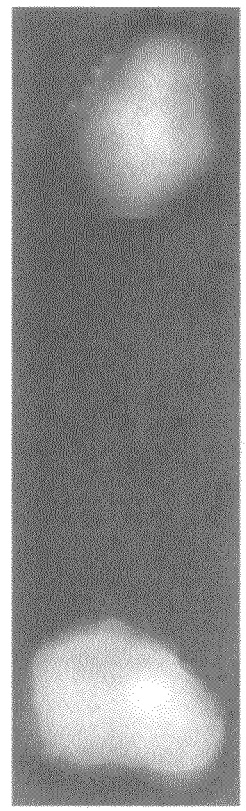

FIG. 12 shows an overall schematic of the model used in this study. In vitro activated, ovalbumin-specific T cells were labeled and injected into a MHC-matched host mouse, that also received a s.c. injection of antigen emulsified in IFA. Sterile PBS was injected in the other flank as a negative control. FIGS. 13-15 show exemplary results from these experiments. The in vivo MRI results (FIG. 13) demonstrate specific T cell homing to the lymph node draining antigen. No T cells are visible in the control lymph node. $^{19}$F was also detected in the mesenteric regions, especially at the earlier time points. With aid of the external $^{19}$F reference capillary, we quantified the number of apparent cells present in the lymph node (FIG. 14) using the methods described above. In vivo optical imaging (FIG. 15a) demonstrates that the dual-mode PFPE nanoparticles in the labeled cells can be imaged in live mice in superficial regions, including mesentery and superficial lymph nodes. The inguinal lymph nodes can overlap with the intestinal loops; to prevent ambiguity in localization, the lymph nodes were excised and imaged separately (FIG. 15b). This panel shows fluorescence only in the draining inguinal node on the side of the Ova/IFA injection, while the control node had no fluorescence and was also smaller in size.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

1. Miyazaki A, Hanafusa T, Yamada K, Miyagawa J, Fujinokurihara H, Nakajima H, Nonaka K, Tarui S. Predominance of lymphocytes-T in pancreatic-islets and spleen of pre-diabetic non-obese diabetic (NOD) mice—a longitudinal-study. Clin Exp Immunol 1985; 60(3):622-630.
2. Leiter E H, Prochazka M, Coleman D L. The nonobese diabetic (NOD) mouse. Am J Pathol 1987; 128(2):380-383.
3. Yeh T C, Zhang W, Ildstad S T, Ho C. Intracellular labeling of T-cells with superparamagnetic contrast agents. Magn Reson Med 1993; 30(5):617-625.
4. Lewin M, Carlesso N, Tung C H, Tang X W, Cory D, Scadden D T, Weissleder R. Tat peptide-derivatized magnetic nanoparticles allow in vivo tracking and recovery of progenitor cells. Nat Biotechnol 2000; 18(4):410-414.
5. Hoehn M, Kustermann E, Blunk J, Wiedermann D, Trapp T, Wecker S, Focking M, Arnold H, Hescheler J, Fleischmann B K, Schwindt W, Buhrle C. Monitoring of implanted stem cell migration in vivo: A highly resolved in vivo magnetic resonance imaging investigation of experimental stroke in rat. Proc Natl Acad Sci USA 2002; 99(25):16267-16272.
6. Ahrens E T, Feili-Hariri M, Xu H, Genove G, Morel P A. Receptor-mediated endocytosis of iron-oxide particles provides efficient labeling of dendritic cells for in vivo MR imaging. Magn Reson Med 2003; 49(6):1006-1013.
7. Kircher M F, Allport J R, Graves E E, Love V, Josephson L, Lichtman A H, Weissleder R. In vivo high resolution three-dimensional imaging of antigen-specific cytotoxic T-lymphocyte trafficking to tumors. Cancer Res 2003; 63(20):6838-6846.
8. Bulte J W M, Arbab A S, Douglas T, Frank J A. Preparation of magnetically labeled cells for cell tracking by magnetic resonance imaging. Method Enzymol 2004; 386:275-299.
9. Modo M, Mellodew K, Cash D, Fraser S E, Meade T J, Price J, Williams S C R. Mapping transplanted stem cell migration after a stroke: a serial, in vivo magnetic resonance imaging study. Neuroimage 2004; 21(1):311-317.
10. Billotey C, Aspord C, Beuf O, Piaggio E, Gazeau F, Janier M F, Thivolet C. T-cell homing to the pancreas in autoimmune mouse models of diabetes: in vivo MR imaging. Radiology 2005; 236(2):579-587.
11. Moore A, Grimm J, Han B, Santamaria P. Tracking the recruitment of diabetogenic CD8+ T-cells to the pancreas in real time. Diabetes 2004; 53(6): 1459-1466.
12. Anderson S A, Shukaliak-Quandt J, Jordan E K, Arbab A S, Martin R, McFarland H, Frank J A. Magnetic resonance imaging of labeled T-cells in a mouse model of multiple sclerosis. Ann Neurol 2004; 55(5):654-659.
13. Evgenov N V, Medarova Z, Pratt J, Pantazopoulos P, Leyting S, Bonner-Weir S, Moore A. In vivo imaging of immune rejection in transplanted pancreatic islets. Diabetes 2006; 55(9):2419-2428.
14. Evgenov N V, Medarova Z, Dai G P, Bonner-Weir S, Moore A. In vivo imaging of islet transplantation. Nat Med 2006; 12(1):144-148.
15. Turvey S E, Swart E, Denis M C, Mahmood U, Benoist C, Weissleder R, Mathis D. Noninvasive imaging of pancreatic inflammation and its reversal in type 1 diabetes. J Clin Invest 2005; 115(9):2454-2461.
16. Wu Y L, Ye Q, Foley L M, Hitchens T K, Sato K, Williams J B, Ho C. In situ labeling of immune cells with iron oxide particles: An approach to detect organ rejection by cellular MRI. Proc Natl Acad Sci USA 2006; 103(6):1852-1857.
17. Shapiro E M, Sharer K, Skrtic S, Koretsky A P. In vivo detection of single cells by MRI. Magn Reson Med 2006; 55(2):242-249.
18. Ahrens E T, Flores R, Xu H, Morel P A. In vivo imaging platform for tracking immunotherapeutic cells. Nat Biotechnol 2005; 23(8):983-987.
19. You S, Chen C, Lee W H, Wu C H, Judkowski V, Pinilla C, Wilson D B, Liu C P. Detection and characterization of T cells specific for BDC2.5 T cell-stimulating peptides. J Immunol 2003; 170(8):4011-4020.
20. Ablamunits V, Quintana F, Reshef T, Elias D, Cohen I R. Acceleration of autoimmune diabetes by cyclophosphamide is associated with an enhanced IFN-gamma secretion pathway. J Autoimmun 1999; 13(4):383-392.
21. Gudbjartsson H, Patz S. The Rician distribution of noisy MRI data. Magn Reson Med 1995; 34(6):910-914.
22. Cantor J, Haskins K. Effector function of diabetogenic CD4 Th1 T cell clones: a central role for TNF-alpha. J Immunol 2005; 175(11):7738-7745.
23. Phillips J M H S, Parish N M, Fehervari Z, Haskins K, Cooke A. Nondepleting anti-CD4 has an immediate action on diabetogenic effector cells, halting their destruction of pancreatic beta cells. J Immunol 2000; 165(4):1949-1955.
24. Meyer K L, Joseph P M, Mukheiji B, Livolsi V A, Lin R. Measurement of vascular volume in experimental rat tumors by 19F magnetic resonance imaging. Invest Radiol 1993; 28(8):710-719.
25. Fishman J E, Joseph P M, Floyd T F, Mukherji B, Sloviter H A. Oxygen-sensitive 19F NMR imaging of the vascular system in vivo. Magn Reson Imaging 1987; 5(4):279-285.
26. Eidelberg D, Johnson G, Barnes D, Tofts P S, Delpy D, Plummer D, McDonald W I. 19F NMR imaging of blood oxygenation in the brain. Magn Reson Med 1988; 6(3): 344-352.
27. Wilson C A, Berkowitz B A, McCuen B W, Charles H C. Measurement of preretinal oxygen-tension in the vitrectomized human eye using F-19 magnetic resonance spectroscopy. Arch Ophthalmol-Chic 1992; 110(8):1098-1100.
28. Dardzinski B J, Sotak C H. Rapid tissue oxygen tension mapping using 19F inversion-recovery echo-planar imaging of perfluoro-15-crown-5-ether. Magn Reson Med 1994; 32(1):88-97.
29. Noth U, Morrissey S P, Deichmann R, Adolf H, Schwarzbauer C, Lutz J, Haase A. In vivo measurement of partial oxygen pressure in large vessels and in the reticuloendothelial system using fast 19F-MRI. Magn Reson Med 1995; 34(5):738-745.
30. Lutz J, Noth U, Morrissey S P, Adolf H, Deichmann R, Haase A. Measurement of oxygen tensions in the abdominal cavity and in the skeletal muscle using 19F-MRI of neat PFC droplets. Adv Exp Med Biol 1997; 428:569-572.
31. Duong T Q, Kim S G. In vivo MR measurements of regional arterial and venous blood volume fractions in intact rat brain. Magn Reson Med 2000; 43(3):393-402.
32. Xia M N, Kodibagkar V, Liu H L, Mason R P. Tumour oxygen dynamics measured simultaneously by near-infrared spectroscopy and F-19 magnetic resonance imaging in rats. Phys Med Biol 2006; 51(1):45-60.
33. Morawski A M, Winter P M, Yu X, Fuhrhop R W, Scott M J, Hockett F, Robertson J D, Gaffney P J, Lanza G M, Wickline S A. Quantitative "magnetic resonance immunohistochemistry" with ligand-targeted F-19 nanoparticles. Magn Reson Med 2004; 52(6): 1255-1262.
34. Lanza G M, Winter P M, Neubauer A M, Caruthers S D, Hockett F D, Wickline S A. 1H/19F magnetic resonance molecular imaging with perfluorocarbon nanoparticles. In: Ahrens E T, editor. In vivo cellular and molecular imaging. Volume 70. Current topics in developmental biology. San Diego: Elsevier; 2005. p 58-78.
35. Pelchen-Matthews A, Parsons I J, Marsh M. Phorbol ester-induced downregulation of CD4 is a multistep process involving dissociation from p56lck, increased association with clathrin-coated pits, and altered endosomal sorting. J Exp Med 1993; 178(4):1209-1222.
36. Phillips J M, Haskins K, Cooke A. MAdCAM-1 is needed for diabetes development mediated by the T cell clone, BDC-2.5. Immunology 2005; 116(4):525-531.
37. Pakala S V, Kurrer M O, Katz J D. T helper 2 (Th2) T cells induce acute pancreatitis and diabetes in immune-compromised nonobese diabetic (NOD) mice. J Exp Med 1997; 186(2):299-306.
38. Fabien N, Bergerot I, Maguer-Satta V, Orgiazzi J, Thivolet C. Pancreatic lymph nodes are early targets of T cells during adoptive transfer of diabetes in NOD mice. J Autoimmun 1995; 8(3):323-334.
39. Miller M J, Safrina O, Parker I, Cahalan M D. Imaging the single cell dynamics of CD4+ T cell activation by dendritic cells in lymph nodes. J Exp Med 2004; 200(7):847-856.
40. Ribeiro R M, Mohri H, Ho D D, Perelson A S. In vivo dynamics of T cell activation, proliferation, and death in HIV-1 infection: why are CD4+ but not CD8+ T cells depleted? Proc Natl Acad Sci USA 2002; 99(24):15572-15577.
41. Feili-Hariri, M., et al., Immunotherapy of NOD mice with bone marrow-derived dendritic cells. Diabetes, 1999.48: 2300-2308.
42. Pluchino, S., et al., Injection of adult neurospheres induces recovery in a chronic model of multiple sclerosis. Nature, 2003. 422(6933): p. 688-694.
43. Yeh, T. C., et al., In-vivo dynamic MRI tracking of rat T-cells labeled with superparamagnetic iron-oxide particles. Magn Reson Med, 1995. 33: 200-208.
44. Schulze, E., et al., Cellular uptake and trafficking of a prototypical magnetic iron oxide label in vitro. Invest Radiol, 1995. 30(10): 604-10.
45. Moore, A., R. Weissleder, and A. Bogdanov, Uptake of dextran-coated monocrystalline iron oxides in tumor cells and macrophages. JMRI-Journal of Magnetic Resonance Imaging, 1997. 7(6): 1140-1145.
46. Weissleder, R., et al., Magnetically labeled cells can be detected by MR imaging. JMRI-Journal of Magnetic Resonance Imaging, 1997. 7(1): 258-263.
47. Schoepf, U., et al., Intracellular magnetic labeling of lymphocytes for in vivo trafficking studies. Biotechniques, 1998. 24(4): 642-+.
48. Ye, Q., et al., In vivo detection of acute rat renal allograft rejection by MRI with USPIO particles. Kidney International, 2002. 61(3): 1124-1135.
49. Dousset, V., et al., In vivo macrophage activity imaging in the central nervous system detected by magnetic resonance. Magnetic Resonance in Medicine, 1999. 41(2): 329-333.
50. Josephson, L., et al., High-efficiency intracellular magnetic labeling with novel superparamagnetic-tat peptide conjugates. Bioconjugate Chemistry, 1999. 10(2): 186-191.
51. Dodd, C. H., et al., Normal T-cell response and in vivo magnetic resonance imaging of T cells loaded with HIV transactivator-peptide-derived superparamagnetic nanoparticles. Journal of Immunological Methods, 2001. 256 (1-2): 89-105.
52. Kanno, S., et al., Macrophage accumulation associated with rat cardiac allograft rejection detected by magnetic resonance imaging with ultrasmall superparamagnetic iron oxide particles. Circulation, 2001. 104(8): 934-938.
53. McGoron, A. J., et al., Perfluorocarbon distribution to liver, lung and spleen of emulsions of perfluorotributylamine (FTBA) in pigs and rats and perfluorooctyl bromide (PFOB) in rats and dogs by F-19 NMR-spectroscopy. Artificial Cells Blood Substitutes and Immobilization Biotechnology, 1994. 22(4): 1243-1250.
54. Noth, U., et al., Perfluoro-15-crown-5-ether labelled macrophages in adoptive transfer experimental allergic encephalomyelitis. Artificial Cells Blood Substitutes and Immobilization Biotechnology, 1997. 25(3): 243-254.
55. Girolomoni, G., et al., Establishment of a cell-line with features of early dendritic cell precursors from fetal mouse skin. European Journal of Immunology, 1995. 25(8): 2163-2169.
56. WO2005072780
57. Arbab, A. S., et al., Blood, 2004. Aug. 15; 104(4):1217-23.
58. Floris S., et al., Brain. 2004 March;127(Pt 3):616-27.
59. U.S. Pat. No. 5,958,371
60. US patent application 20020192688

EQUIVALENTS

While specific embodiments of the subject inventions are explicitly disclosed herein, the above specification is illustrative and not restrictive. Many variations of the inventions will become apparent to those skilled in the art upon review of this specification and the claims below. The full scope of the inventions should be determined by reference to the claims, along with their full scope of equivalents, and the specification, along with such variations.

We claim:
1. A method for quantifying cell number in vivo, the method comprising:
   a. administering to a subject cells that are labeled with a fluorocarbon imaging reagent, wherein at least a portion of the fluorocarbon imaging reagent was internalized into the cell;
   b. examining at least a portion of the subject by $^{19}F$ magnetic resonance imaging (MRI), thereby detecting the cells that are labeled with the fluorocarbon imaging reagent in the subject; and
   c. quantifying the number of labeled cells in a region of interest (ROI).
2. The method of claim 1, wherein the fluorocarbon imaging reagent is a perfluoropolyether.
3. The method of claim 1, wherein the fluorocarbon imaging reagent is a perfluoro-crown ether.
4. The method of claim 1, wherein the imaging reagent is a perfluoro-15-crown-5-ether.
5. The method of claim 1, wherein the fluorocarbon is a perfluorinated polyether having an average formula:

XO(Y—O)$_n$Z wherein Y is selected from the group comprising:

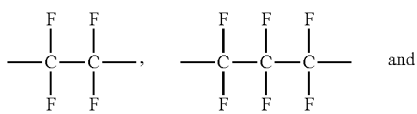

-continued

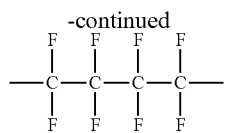

wherein n is an integer from 8 to 20; wherein X and Z are the same and are selected from the group comprising: perfluoroalkyls, perfluoroethers, fluoroalkyls terminated with fluoroacyl, carboxyl, amide or ester, methylols, acid chlorides, amides, amidines, acrylates and esters.

6. The method of claim 1, wherein the fluorocarbon imaging reagent is selected from the group comprising: a linear perfluoropolyether, a cyclic perfluoropolyether and a mixture thereof.

7. The method of claim 1, wherein prior to administration to the subject, the cells are contacted with a composition comprising the fluorocarbon imaging reagent, whereby the cells are labeled with the fluorocarbon imaging reagent.

8. The method of claim 7, wherein the composition comprising the fluorocarbon imaging reagent further comprises an uptake enhancing reagent.

9. The method of claim 8, wherein the uptake enhancing reagent comprises a compound selected from the group consisting of:
  a. cationic lipid; and
  b. cationic polypeptide.

10. The method of claim 9, wherein the cationic peptide is a protamine.

11. The method of claim 7, wherein the composition comprising the fluorocarbon imaging reagent further comprises:
  a. a surfactant; and
  b. a cationic lipid.

12. The method of claim 7, wherein the composition comprising the fluorocarbon imaging reagent further comprises Pluronic L-35.

13. The method of claim 7, wherein the fluorocarbon imaging reagent is formulated as an emulsion.

14. The method of claim 7, wherein the emulsion comprises particles having a mean diameter of between 30 and 500 nm.

15. The method of claim 1, wherein prior to administration to the subject, the cells are labeled with perfluorocarbon emulsion particles using electroporation.

16. The method of claim 1, wherein the cell is a mammalian cell.

17. The method of claim 1, wherein the cell is a cell of the immune system.

18. The method of claim 1, wherein the cell is a T cell.

19. The method of claim 1, wherein the cell is a dendritic cell.

20. The method of claim 1, wherein the cell is a stem cell.

21. The method of claim 1, further comprising collecting a $^1$H data set.

22. The method of claim 1, further comprising generating and comparing a $^{19}$F image and a $^1$H image.

23. The method of claim 1, wherein the cell is administered to the subject as part of a cellular therapeutic regimen.

24. The method of claim 1, wherein quantifying comprises using a calibrated $^{19}$F signal in the ROI.

25. The method of claim 24, wherein the cellular dose of fluorocarbon imaging reagent is calculated prior to administration of cells to the subject.

26. The method of claim 1, wherein examining comprises detecting a pre-calibrated $^{19}$F signal from which one can deduce a relationship between the $^{19}$F signal in the ROI and the representative number of $^{19}$F molecules or cell quantity.

27. The method of claim 1, wherein examining comprises detecting a contemporaneous signal in the ROI from which one can deduce a relationship between the signal and the representative number of $^{19}$F molecules or cell quantity.

28. The method of claim 1, wherein examining comprises detecting a post-calibrated $^{19}$F signal in the ROI from which one can deduce a relationship between the signal and the representative number of $^{19}$F molecules or cell quantity.

29. The method of claim 1, wherein quantifying is done by comparison to a calibrated external $^{19}$F reference during the $^{19}$F MRI scan of the subject.

30. The method of claim 29, wherein the reference is a cell free reference.

31. The method of claim 1, wherein quantifying comprises calculating ratios of the intensity of $^{19}$F signal and the volume of labeled cells in a ROI compared to a reference.

32. The method of claim 1, wherein quantifying the number of labeled cells comprises using at least one of the parameters from the group consisting of: (i) the cellular dose of labeling agent (i.e., $F_c$) measured in vitro; (ii) in vivo $^{19}$F MRI data set taken in the subject at one or more time points following labeled cell administration; (iii) the voxel volume; (iv) the in-plane voxel area (i.e., area of the image pixel); (v) the MRI data set from the $^{19}$F reference standard; (vi) the measured Johnson noise of the $^{19}$F MRI data in the subject material; (vii) the measured signal-to-noise ratio (SNR) of one or more voxels of the $^{19}$F MRI data set in the subject material; (viii) the measured SNR of one or more voxels of the $^{19}$F MRI data set from the reference standard; (ix) the $^{19}$F NMR relaxation times (T1, T2, and T2*) of the subject material; and (x) the $^{19}$F NMR relaxation times (T1, T2, and T2*) of the reference standard.

33. The method of claim 1, wherein quantifying the number of labeled cells comprises using the formula:

$$N_c = \frac{[F_R]v}{I_R} \frac{1}{F_c} \sum_{i=1}^{N_{ROI}} I_c^{(i)}$$

where: $N_c$=total number of labeled cells in the ROI; $[F_R]$=concentration of $^{19}$F in the calibrated $^{19}$F reference solution (or gel); v=voxel volume; $I_R$=mean intensity of the calibrated $^{19}$F reference taken with the MRI scan, averaged over one or more voxels; $F_c$=average $^{19}$F cellular dose of the labeling agent measured in vitro; $N_{ROI}$=number of voxels in the ROI containing labeled cells; $I_c^{(i)}$=image intensity of the $i^{th}$ voxel in the ROI containing labeled cells; i=unitless index for voxels in the ROI containing labeled cells.

* * * * *

UNITED STATES PATENT AND TRADEMARK OFFICE
CERTIFICATE OF CORRECTION

PATENT NO. : 8,263,043 B2  
APPLICATION NO. : 11/787521  
DATED : September 11, 2012  
INVENTOR(S) : Eric T. Ahrens and Mangala Srinivas Page 1 of 1

It is certified that error appears in the above-identified patent and that said Letters Patent is hereby corrected as shown below:

In the Specification

Replace Column 1, Lines 16-22 with the following:
This invention was made with United States government support under grant numbers EB003453 and EB001977 awarded by the National Institutes of Health. The U. S. government has certain rights in the invention.

Signed and Sealed this
Twenty-ninth Day of March, 2022

Drew Hirshfeld
*Performing the Functions and Duties of the*
*Under Secretary of Commerce for Intellectual Property and*
*Director of the United States Patent and Trademark Office*